US006858611B2

(12) United States Patent
Reed et al.

(10) Patent No.: US 6,858,611 B2
(45) Date of Patent: Feb. 22, 2005

(54) POTASSIUM CHANNEL INHIBITORS

(75) Inventors: Aimee Dolores Reed, Durham, NC (US); Michael Francis Gross, Durham, NC (US); Serge Beaudoin, Morrisville, NC (US)

(73) Assignee: Icagen, Inc., Durham, NC (US)

(*) Notice: Subject to any disclaimer, the term of this patent is extended or adjusted under 35 U.S.C. 154(b) by 0 days.

(21) Appl. No.: 10/390,597

(22) Filed: Mar. 19, 2003

(65) Prior Publication Data

US 2003/0236261 A1 Dec. 25, 2003

Related U.S. Application Data

(62) Division of application No. 09/910,817, filed on Jul. 24, 2001, now Pat. No. 6,566,380
(60) Provisional application No. 60/220,515, filed on Jul. 25, 2000.

(51) Int. Cl.$^7$ ................. A61K 31/4709; A61K 31/517; C07D 401/12; C07D 403/12; A61P 9/06
(52) U.S. Cl. ................. 514/248; 514/299; 514/310; 514/313; 514/243; 514/249; 514/260.1; 514/258.1; 514/357; 514/400; 514/256; 514/365; 514/397; 514/602; 546/143; 546/159; 546/160; 546/112; 546/337; 544/235; 544/253; 544/356; 544/349; 544/183; 544/335; 548/338.1; 548/204; 548/315.1; 564/84
(58) Field of Search ................. 546/143, 159, 546/160, 112; 544/235, 253, 356, 349, 183; 514/299, 310, 313, 243, 249, 260.1, 258.1, 248

(56) References Cited

U.S. PATENT DOCUMENTS

| | | | | |
|---|---|---|---|---|
| 3,953,506 A | * | 4/1976 | Spicer et al. | |
| 4,005,140 A | * | 1/1977 | Spicer et al. | |
| 4,975,453 A | * | 12/1990 | Becker et al. | |
| 5,006,512 A | * | 4/1991 | Ohnishi | |
| 5,215,985 A | * | 6/1993 | Murphy et al. | |
| 5,234,947 A | * | 8/1993 | Cherksey | |
| 5,242,947 A | * | 9/1993 | Cherksey et al. | |
| 5,310,932 A | * | 5/1994 | Atwal et al. | |
| 5,328,830 A | * | 7/1994 | Janis et al. | |
| 5,356,775 A | * | 10/1994 | Hebert et al. | |
| 5,401,758 A | * | 3/1995 | Atwal et al. | |
| 5,401,848 A | * | 3/1995 | Atwal | |
| 5,451,580 A | * | 9/1995 | Murphy et al. | |
| 5,453,421 A | * | 9/1995 | Atwal et al. | |
| 5,486,515 A | * | 1/1996 | Brown et al. | |
| 6,083,986 A | * | 7/2000 | Castle et al. | |
| 6,333,337 B1 | * | 12/2001 | Gross et al. | |
| 6,458,794 B2 | * | 10/2002 | Gross et al. | 514/256 |

FOREIGN PATENT DOCUMENTS

| | | |
|---|---|---|
| EP | 0 286 278 | 10/1988 |
| EP | 0 317 321 | 5/1989 |
| EP | 0 321 175 | 8/1989 |
| EP | 0 472 053 | 2/1992 |
| EP | 0 488 616 | 6/1992 |
| EP | 0 587 180 | 3/1994 |
| EP | 0 608 858 | 8/1994 |
| WO | 95/18617 | 7/1995 |
| WO | 95/26342 | 10/1995 |
| WO | 96/21640 | 7/1996 |
| WO | 96/36596 | 11/1996 |
| WO | 97/25982 | 7/1997 |
| WO | 97/25983 | 7/1997 |
| WO | 97/26300 | 7/1997 |
| WO | 98/04521 | 2/1998 |
| WO | 98/36749 | 8/1998 |
| WO | 99/37607 | 7/1999 |

OTHER PUBLICATIONS

Lumma et al. (1987) J. Med. Chem. 30(5): 755–758).*

Still et al, "Rapid Chromatographic Technique for Preparative Separation with Moderate Resolution," J. Org. Chem., vol. 43, No. 14, 1978, pp. 2923–2925.

Castle et al., "Characterization of 4–Aminopyridne Block of the Transient Outward K$^+$Current in Adult Rat Ventricular Myocytes," The Journal of Pharmacology and Experimental, vol. 264, No. 3, pp. 1450–1459.

Deal et al, "Molecular Physiology of Cardiac Potassium Channels," Physiological Reviews, vol. 76, No. 1, Jan. 1996, pp. 49–67.

Wang et al, "Sustained Depolarization–Induced Outward Current in Human Atrial Myocytes, Evidence for a Novel Delayed Rectified K$^+$Current Similar to Kv1.5 Cloned Channel Current," Circulation Research, vol. 73, No. 6, Dec. 1993, pp. 1061–1076.

Hamill, "Improved Patch–Clamp Techniques for High––Resolution Current Recording from Cells and Cell–Free Membrane Patches," Pflüger Archiv, (1981) 391:85–100.

Fedida et al, "Identity of a Novel Delayed Rectifier Current From Human Heart With a Cloned K$^+$Channel Current," Circulation Research, vol. 73, No. 1, Jul. 1993, pp. 210–216.

Chandy et al., "Voltage–Gated Potassium Channels are Required for Human T Lymphocyte Activation," J. Exp. Med., vol. 160, Aug. 1984, pp. 369–385.

Sanguinetti, "Modulation of Potassium Channels by Anti-arrhythmic and Antihypertensive Drugs," Hypertension, vol. 19, No. E, Mar. 1992, pp. 228–236.

Lynch et al, "Therapeutic Potential of modulating Potassium, Currents in the Diseased Myocardium," The FASEB Journal, vol. 6, Aug. 1992, p. 2952–2960.

(List continued on next page.)

Primary Examiner—Evelyn Mei Huang
(74) Attorney, Agent, or Firm—Banner & Witcoff, Ltd.

(57) ABSTRACT

Compounds which are useful as potassium channel inhibitors and which because of their slow off-rates are especially useful for the treatment of cardiac arrhythmias are described.

9 Claims, 5 Drawing Sheets

OTHER PUBLICATIONS

Colatsky et al, "Channel Specificity in Antiarrhythmic Drug Action," Circulation, vol. 82, No. 6, Dec. 1990, pp. 2235–2242.

Halliwell, "$K^+$Channels in the Central Nervous System," pp. 348–381.

Amos et al, "Differences Between Outward Currents of Human Atrial and Subepicardial Ventricular Myocytes," Journal of Physiology, 1986, 491.1, pp. 31–50.

Wang et al, "Effects of Flecanide, Quinidine, and 4–Aminopyridine on Transient Outward and Ultrarapid Delayed Rectifier Currents in Human Atrial Myocytes," The Journal of Pharmacology and Experimental Therapeutics, vol. 272, No. 1, pp. 184–196.

Lin et al. "Voltage–gated Potassium Channel Regulate Calcium–dependent Pathways Involved in Human T Lymphocyte Activation," J. Exp. Med., vol. 177, pp. 637–645.

Kaczorowki et al, "lymphocyte Ion Channels as a Target for Immunosuppression," Perspective in Drug Discovery and Design 2, 1994, pp. 233–248.

Leonard et al, "Selective Blockers of voltage–Gated $K^+$Channels Depolarize Human T Lymphocytes: Mechanism of the Antiproliferative Effect of Charybdotoxin", vol. 89, Nov. 1992, pp. 10094–10098.

Doupnik et al, "The Inward Rectifier Potassium Channel Family", Current Opinion in Neurobiology, 1995, 5:268–277.

Chandy et al, "Voltage–Gated Potassium Channel Genes", Handbook of Receptors and Channels, 1995, pp. 1–71.

Epps et al., Chemistry and Physics of Lipids, 69, 1994, pp. 137–150.

Chem Abs., vol. 104, No. 9 Abs No. 68632 (Mar. 3, 1986).

International Search Report PCT/US97/12559.

International Search Report PCTUS01/23258.

Robertson et al. J. Med. Chem. vol. 33, No. 6, 1990.

* cited by examiner

POTASSIUM CHANNEL INHIBITORS

This application is a divisional application of U.S. Ser. No. 09/910,817 filed Jul. 24, 2001, now U.S. Pat. No. 6,566,380 which application claimed the benefit under 35 U.S.C. §19(e)(1) of prior filed provisional application 60/220,515, filed Jul. 25, 2000.

BACKGROUND OF THE INVENTION

1. Field of the Invention

The present invention is broadly directed to a class of compounds useful as potassium channel inhibitors.

2. Description of Related Art

The importance of potassium channels was first recognized almost fifty years ago when Hodgkin and Huxley discovered that potassium ions contributed to the current that excited the squid giant axon. Research in the area, however, was hampered by the lack of selective, high affinity ligands for potassium channels. But the advent of recombinant DNA techniques and single cell and whole cell voltage clamp techniques has changed the slow pace of the field. Indeed, potassium channels which exhibit functional, pharmacological and tissue distribution characteristics have been cloned. These cloned potassium channels are useful targets in assays for identifying candidate compounds for the treatment of various disease states. Potassium channels have turned out to be the most diverse family of ion channels discovered to date. They modulate a number of cellular events such as muscle contraction, neuro-endocrine secretion, frequency and duration of action potentials, electrolyte homeostasis, and resting membrane potential.

Potassium channels are expressed in eukaryotic and procaryotic cells, and are elements in the control of electrical and nonelectrical cellular functions. Potassium channels have been classified according to their biophysical and pharmacological characteristics. Subclasses of these channels have been named based on amino acid sequence and functional properties. Salient among these are the voltage dependent potassium channels, for example voltage gated potassium channels (e.g., Kv1, Kv2, Kv3, Kv4). Subtypes within these subclasses have been characterized as to their putative function, pharmacology and distribution in cells and tissues (Chandy and Gutman, "Voltage-gated potassium channel genes" in Handbook of Receptors and Channels-Ligand and Voltage-gated Ion Channels, ed. R. A. North, 1995; Doupnik et al., *Curr. Opin. Neurobiol.* 5:268, 1995). For example, the Kv1 class of potassium channels is further subdivided depending on the molecular sequence of the channel, for example Kv 1.1, Kv 1.3, Kv 1.5. Functional voltage-gated K+ channels can exist as multimeric structures formed by the association of either identical or dissimilar subunits. This phenomena is thought to account for the wide diversity of K+ channels. However, subunit compositions of native K+ channels and the physiologic role that particular channels play are, in most cases, still unclear.

Membrane depolarization by Kv 1.3 inhibition has been shown to be an effective method to prevent T-cell proliferation and therefore has applications in many autoimmune conditions. Inhibition of K+ channels in the plasma membrane of human T-lymphocytes has been postulated to play a role in eliciting immunosuppressive responses by regulating intracellular Ca++ homeostasis, which has been found to be important in T-cell activation.

The Kv 1.3 voltage-gated potassium channel is found in neurons, blood cells, osteoclasts and T-lymphocytes. The Chandy and Cahalan laboratories proposed a hypothesis that blocking the Kv 1.3 channel would elicit an immunosuppressant response. (Chandy et al., *J. Exp. Med.* 160, 369, 1984; Decoursey et al., Nature, 307, 465, 1984). However, the K+ channel blockers employed in their studies were non-selective. Until research with the peptide margatoxin, a peptide found in scorpion venom, no specific inhibitor of the Kv 1.3 channel existed to test this hypothesis. Although a laboratory (Price et al, *Proc. Natl. Acad. Sci. USA*, 86, 10171, 1989) showed that charybdotoxin would block Kv 1.3 in human T cells, charybdotoxin was subsequently shown to inhibit four different K+ channels (Kv 1.3 and three distinct small conductance Ca++ activated K+ channels) in human T-lymphocytes, limiting the use of this toxin as a probe for the physiological role of Kv 1.3 (Leonard et al, *Proc. Natl. Acad. Sci. USA*, 89, 10094, 1992). Margatoxin, on the other hand, blocks only Kv 1.3 in T-cells, and has immunosuppressant activity in both in vitro and in vivo models. (Lin et al., *J. Exp. Med.*, 177, 637, 1993). The therapeutic utility of this compound, however, is limited by its potent toxicity. Recently, a class of compounds has been reported that may be an attractive alternative to the above-mentioned drugs, see for example U.S. Pat. Nos. 5,670,504; 5,631,282; 5,696,156; 5,679,705; and 5,696,156. While addressing some of the activity/toxicity problems of previous drugs, these compounds tend to be of large molecular weight and are generally produced by synthetic manipulation of a natural product, isolation of which is cumbersome and labor intensive.

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

Although the underlying pathogenesis of each of these conditions may be quite different, they have in common the appearance of a variety of auto-antibodies and self-reactive lymphocytes. Such self-reactivity may be due, in part, to a loss of the homeostatic controls under which the normal immune system operates. Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A (CsA), which was approved by the US FDA in 1983 is currently the leading drug used to prevent rejection of transplanted organs. In 1993, FK-506 (Prograf) was approved by the US FDA for the prevention of rejection in liver transplantation. CsA and FK-506 act by inhibiting the body's immune system from mobilizing its vast arsenal of natural protecting agents to reject the transplant's foreign protein. In 1994, CsA was approved by the US FDA for the treatment of severe psoriasis and has been approved by European regulatory agencies for the treatment of atopic dermatitis. Though they are effective in fighting transplant rejection, CsA and FK-506 are known to cause several undesirable side effects including nephrotoxicity, neurotoxicity, and gastrointestinal discomfort. Therefore, a selective immunosuppressant without these side effects still remains to be developed. Potassium channel inhibitors promise to be the solution to this problem.

Atrial fibrillation (AF) is the most common sustained cardiac arrhythmia in clinical practice and is likely to increase in prevalence with the aging of the population. Currently, AF affects more than 1 million Americans annually, represents over 5% of all admissions for cardiovascular diseases and causes more than 80,000 strokes each year in the United States. While AF is rarely a lethal arrhythmia, it is responsible for substantial morbidity and can lead to complications such as the development of congestive heart failure or thromboembolism. Currently available Class I and Class III antiarrhythmic drugs reduce the rate of recurrence of AF, but are of limited use because of a variety of potentially adverse side effects including ventricular proarrhythmia. Because current therapy is inadequate and fraught with side effects, there is a clear need to develop new therapeutic approaches.

Antiarrhythmic agents of Class III are drugs that cause a selective prolongation of the duration of the action potential without significant cardiac depression. Available drugs in this class are limited in number. Examples such as sotalol and amiodarone have been shown to possess interesting Class III properties (Singh B. N., Vaughan Williams E. M. "A Third Class Of Anti-Arrhythmic Action: Effects On Atrial And Ventricular Intracellular Potentials And Other Pharmacological Actions On Cardiac Muscle, of MJ 1999 and AH 3747" Br. *J Pharmacol* 1970; 39:675–689. and Singh B. N., Vaughan Williams E. M, "The Effect Of Amiodarone, A New Anti-Anginal Drug, On Cardiac Muscle", Br *J Pharmacol* 1970; 39:657–667.), but these are not selective Class III agents. Sotalol also possesses Class II effects which may cause cardiac depression and is contraindicated in certain susceptible patients. Amiodarone, also is not a selective Class III antiarrhythmic agent because it possesses multiple electrophysiological actions and is severely limited by side effects (Nademanee, K. "The Amiodarone Odessey". *J. Am. Coll. Cardiol.* 1992; 20:1063–065.) Drugs of this class are expected to be effective in preventing ventricular fibrillation. Selective class III agents, by definition, are not considered to cause myocardial depression or an induction of arrhythmias due to inhibition of conduction of the action potential as seen with Class I antiarrhythmic agents.

Class III agents increase myocardial refractoriness via a prolongation of cardiac action potential duration. Theoretically, prolongation of the cardiac action potential can be achieved by enhancing inward currents (i.e. Na+ or Ca2+ currents; hereinafter $I_{Na}$ and $I_{Ca}$, respectively) or by reducing outward repolarizing potassium (K+) currents. The delayed rectifier (IK) K+ current is the main outward current involved in the overall repolarization process during the action potential plateau, whereas the transient outward ($I_{to}$) and inward rectifier ($I_{KI}$) K+ currents are responsible for the rapid initial and terminal phases of repolarization, respectively. Cellular electrophysiologic studies have demonstrated that IK consists of two pharmacologically and kinetically distinct K+ current subtypes, IKr (rapidly activating and deactivating) and IKs (slowly activating and deactivating)(Sanguinetti and Jurkiewicz, Two Components Of Cardiac Delayed Rectifier K+ Current: Differential Sensitivity To Block By Class IH Antiarrhythmic Agents, *J Gen Physiol* 1990, 96:195–215). Class III antiarrhythmic agents currently in development, including d-sotalol, dofetilide (UK-68,798), almokalant (H234/09), E-4031 and methanesulfonamide-N-[I'-6-cyano-1,2,3,4-tetrahydro-2-naphthalenyl)-3,4-dihydro4-hydroxyspiro[2H-1-benzopyran-2,4'-piperidin]-6yl] monochloride, predominantly, if not exclusively, block IKr. Although, amiodarone is a blocker of IKs (Balser J. R. Bennett, P. B., Hondeghem, L. M. and Roden, D. M. "Suppression Of Time-Dependent Outward Current In Guinea Pig Ventricular Myocytes: Actions Of Quinidine And Amiodarone. *Circ. Res.* 1991, 69:519–529), it also blocks $I_{Na}$, and $I_{Ca}$, effects thyroid function, is a nonspecific adrenergic blocker, and acts as an inhibitor of the enzyme phospholipase (Nademanee, K. "The Amiodarone Odessey". *J. Am. Coll. Cardiol.* 1992; 20:1063–1065). Therefore, its method of treating arrhythmia is uncertain. Most Class III agents that are known to be in development predominantly block IKr.

Reentrant excitation (reentry) has been shown to be a prominent mechanism underlying supraventricular arrhythmias in man. Reentrant excitation requires a critical balance between slow conduction velocity and sufficiently brief refractory periods to allow for the initiation and maintenance of multiple reentry circuits to coexist simultaneously and sustain AF. Increasing myocardial refractoriness by prolonging action potential duration (APD), prevents and/or terminates reentrant arrhythmias. Most selective Class III antiarrhythmic agents currently in development, such as d-sotalol and dofetilide predominantly, if not exclusively, block IKr, the rapidly activating component of IK found both in atrium and ventricle in man.

Since these IKr blockers increase APD and refractoriness both in atria and ventricle without affecting conduction per se, theoretically they represent potential useful agents for the treatment of arrhythmias like AF. These agents have a liability in that they have an enhanced risk of proarrhythmia at slow heart rates. For example, torsades de points has been observed when these compounds are utilized (Roden, D. M. "Current Status of Class III Antiarrhythmic Drug Therapy", *Am J. Cardiol*, 1993; 72:44B–49B). This exaggerated effect at slow heart rates has been termed "reverse frequency-dependence", and is in contrast to frequency-independent or frequency-dependent actions (Hondeghem, L. M. "Development of Class III Antiarrhythmic Agents" *J. Cadiovasc. Cardiol.* 20 (Suppl. 2):S17–S22).

The slowly activating component of the delayed rectifier (IKs) potentially overcomes some of the limitations of IKr blockers associated with ventricular arrhythmias. Because of its slow activation kinetics however, the role of IKs in atrial repolarization may be limited due to the relatively short APD of the atrium. Consequently, although IKs blockers may provide distinct advantage in the case of ventricular arrhythmias, their ability to affect SVT is considered to be minimal.

The ultra-rapidly activating delayed rectifier K+ current ($I_{kur}$) is believed to represent the native counterpart to a cloned potassium channel designated Kv1.5 and, while present in human atrium, it appears to be absent in human ventricle. Furthermore, because of its rapidity of activation and limited slow inactivation, $I_{kur}$ is believed to contribute significantly to repolarization in human atrium. Consequently, a specific blocker of $I_{kur}$, that is a compound which blocks Kv 1.5, would overcome the shortcoming of other compounds by prolonging refractoriness by retarding repolarization in the human atrium without causing the delays in ventricular repolarization that underlie arrhythmogenic after depolarizations and acquired long QT syndrome observed during treatment with current Class III drugs.

In intact human atrial myocytes an ultra-rapidly activating delayed rectifier K+ current $I_{kur}$ which is also known as the sustained outward current, $I_{sus}$ or $I_{so}$, has been identified and this current has properties and kinetics identical to those expressed by the human K+ channel clone (hKvI.5, HK2) when isolated from human heart and stably expressed in human (HEK-293) cell lines. (Wang, Fermini and Natel, 1993, Circ Res 73:1061–1076; Fedida et al., 1993, Circ Res 73:210–216; Snyders, Tamkun and Bennet, 1993, J Gen Physiol 101:513–543) and originally cloned from rat brain (Swanson et al., 10, Neuron 4:929–939). Although various antiarrythmic agents are now available on the market, those having both satisfactory efficacy and a high margin of safety have not been obtained. For example, antiarrythmic agents of Class I according to the classification scheme of Vaughan-Williams ("Classification Of Antiarrhythmic Drugs" In: Cardiac Arrhythrnias, edited by: E. Sandoe, E. Flensted-Jensen, K. Olesen; Sweden, Astra, Sodertalje, pp449–472, 1981) which cause a selective inhibition of the maximum velocity of the upstroke of the action potential (max) are inadequate for preventing ventricular fibrillation. In addition, they have problems regarding safety, namely, they cause a depression of myocardial contractility and have a tendency to induce arrhythmias due to an inhibition of impulse conduction. Beta-adrenoceptor blockers and calcium antagonists which belong to Class II and IV, respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

The present invention is directed to compounds which have some surprising properties in in vitro testing making them particularly useful as inhibitors of potassium channel function.

It is an object of the present invention, therefore, to provide compounds which are useful for the treatment of diseases in mammals, including humans, and especially for the management of diseases which can be treated by inhibiting cell membrane potassium channels.

Another object of the invention is to provide a method of treating diseases in mammals, including humans, which respond to the inhibition of potassium channel function, which method comprises administering to a mammal in need thereof a compound of the invention.

DETAILED DESCRIPTION OF THE INVENTION

Figure 1:
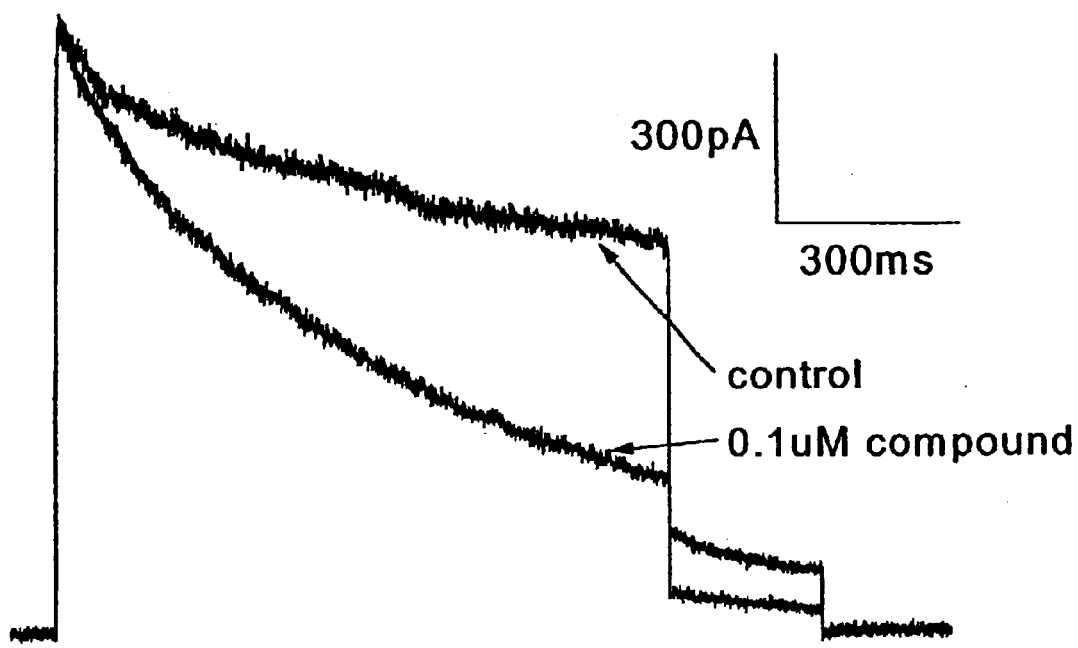
FIG. 1 shows the typical result of eliciting Kv1.5 currents with 1 s voltage steps to 0 mV (from a holding potential of −80 mV) before (control) and 2 min after application of 0.1 $\mu$M of a compound of the prior art. Note that the compound of the prior art exerts no blocking activity until the channel is activated (i.e. no block is apparent at the beginning of the pulse). Block develops following channel activation.

This invention describes compounds and their utility as inhibitors of potassium channel function. The invention is particularly directed to compounds that inhibit potassium channels which could serve as targets for the treatment of cardiac arrhythmias (i.e., $I_{Kur}$, Kv 1.5) especially those occurring in the atria (e.g., atrial flutter and atrial fibrillation) (Wang et al., Circ. Res. 73:1061, 1993; Fedida et al., Circ. Res. 73:210, 1993; Wang et al., J. Pharmacol. Exp. Ther. 272:184, 1995). The present invention also provides a method for treating diseases which respond to the inhibition of potassium channel function. These include, but are not limited to cardiac arrhythmias, cell proliferative disorders including cancer, disorders of the auditory system, central nervous system mediated motor dysfunction and disorders of pulmonary, vascular and visceral smooth muscle contractility.

The invention is particularly based on our discovery that the compounds of the following formula are inhibitors of potassium channel function and are thus useful for inhibiting potassium transport across cellular membranes and for treating cardiac arrhythmias. In particular, these compounds have demonstrated activity against human potassium channels.

Thus, this aspect of the present invention concerns such methods and such compounds having potassium channel inhibitory activity of the following formula and pharmaceutically acceptable salts, esters, amides, complexes, chelates, hydrates, stereoisomers, crystalline or amorphous forms, metabolites, metabolic precursors or prodrugs thereof:

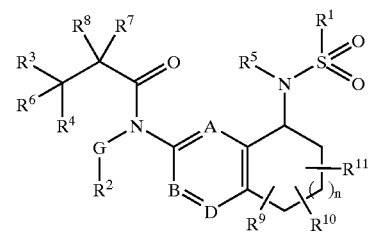

wherein
$R^1$, $R^2$ and $R^3$ are independently selected from the group consisting of aryl, heteroaryl and heterocyclo;
$R^4$ is selected from the group consisting of alkyl, hydroxy, alkoxy, carbocycloalkyl and amino;
$R^5$ and $R^6$ are independently selected from the group consisting of hydrogen and alkyl;
$R^7$ is selected from the group consisting of hydrogen, alkyl, hydroxy, alkoxy and amino;
$R^8$ is selected from the group consisting of hydrogen and alkyl;
$R^9$, $R^{10}$ and $R^{11}$ are independently selected from the group consisting of hydrogen, alkyl and halo;

G is selected from the group consisting of a direct bond and a lower alkylene;

A, B and D are independently selected from the group consisting of a substituted carbon atom, a nitrogen atom, or N-oxide, wherein at least one of A, B, and D is a substituted carbon atom and at most only one of A, B, and D is N-oxide; and n is 1 or 2.

In another aspect, the present invention concerns such methods and such compounds having potassium channel inhibitory activity of the previous formula, and pharmaceutically acceptable salts, esters, amides, complexes, chelates, hydrates, stereoisomers, crystalline or amorphous forms, metabolites, metabolic precursors or prodrugs thereof, wherein A, B and D are —CH—. Such compounds have the formula:

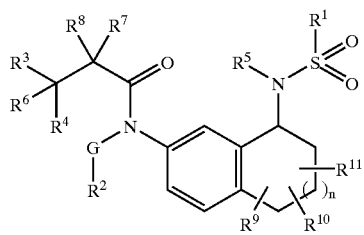

In still another aspect, the present invention concerns such methods and such compounds having potassium channel inhibitory activity and pharmaceutically acceptable salts, esters, amides, complexes, chelates, hydrates, stereoisomers, crystalline or amorphous forms, metabolites, metabolic precursors or prodrugs thereof of the formula:

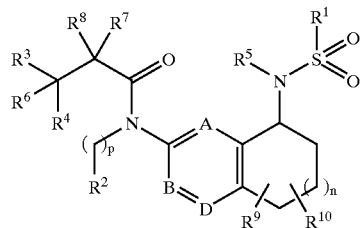

wherein p is 0, 1, 2, or 3 and all of the other variables have the same meaning as noted hereinabove.

In yet another aspect, the present invention concerns such methods and such compounds of the previous formula having potassium channel inhibitory activity and pharmaceutically acceptable salts, esters, amides, complexes, chelates, hydrates, stereoisomers, crystalline or amorphous forms, metabolites, metabolic precursors or prodrugs thereof, wherein A, B and D are —CH—. Such compounds have the formula:

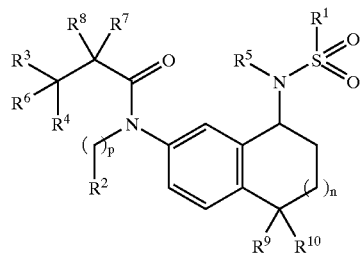

Also preferred are compounds of all the previous formulae wherein $R^9$, $R^{10}$ and $R^{11}$ are each hydrogen.

Preferred subgroups of compounds for practicing such methods includes any of the compound groups as mentioned above, including their pharmaceutically acceptable salts, esters, amides, complexes, chelates, hydrates, stereoisomers, crystalline or amorphous forms, metabolites, metabolic precursors or prodrugs, further defined by having $R^1$ being selected from the group consisting of aryl (preferably phenyl) and heteroaryl; $R^4$ being selected from the group consisting of alkyl (preferably methyl) and alkoxy (preferably methoxy), $R^6$ and $R^8$ being hydrogen and optionally $R^7$ being hydrogen.

Yet another preferred subgroup of compounds for practicing such methods are the above-mentioned compounds, including their pharmaceutically acceptable salts, esters, amides, complexes, chelates, hydrates, stereoisomers, crystalline or amorphous forms, metabolites, metabolic precursors or prodrugs, further defined by having p be 1 and optionally $R^7$ being hydrogen.

A particularly preferred subgroup of compounds for practicing such methods includes compounds (stereoisomers) represented by the following formulae, and their pharmaceutically acceptable salts, esters, amides, complexes, chelates, hydrates, crystalline or amorphous forms, metabolites, metabolic precursors or prodrugs thereof:

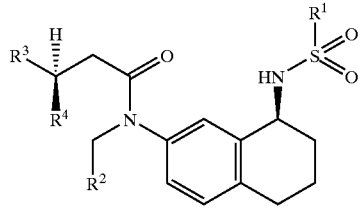

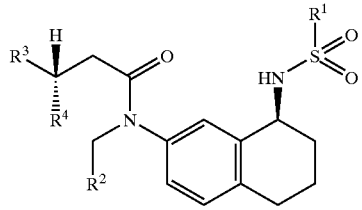

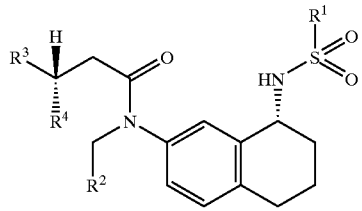

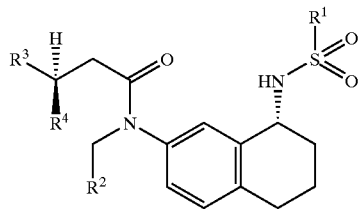

Where $R^1$ is selected from the group consisting of aryl (preferably phenyl) and heteroaryl; $R^2$ is selected from the group consisting of heteroaryl and heterocyclo; $R^3$ is selected from the group consisting of aryl, heteroaryl and heterocyclo; and $R^4$ is selected from the group consisting of lower alkyl, preferably methyl, and alkoxy, preferably methoxy.

Particularly preferred compounds are those of the previously identified formulae, and their pharmaceutically acceptable salts, esters, amides, complexes, chelates, hydrates, crystalline or amorphous forms, metabolites, metabolic precursors or prodrugs thereof, wherein $R^2$ is selected from the group consisting of imidazoyl and pyridyl; $R^3$ is selected from the group consisting of aryl, preferably phenyl, and heteroaryl, preferably thieyl and thiazoyl; and $R^4$ is lower alkyl, preferably methyl.

The term "alkyl" as used alone or in combination in any of the formulae herein refers to an optionally substituted, straight or branched chain saturated hydrocarbon group containing from one to ten carbon atoms. Preferably, the alkyl group is a "$C_{1-5}$ alkyl," alternatively referred to as "lower alkyl," which refer to such groups containing from one to five carbon atoms, such as methyl, ethyl, n-propyl, isopropyl, n-butyl, isobutyl, sec-butyl, tert-butyl and the like. As used throughout the specification and claims the terms "alkyl" and "lower alkyl" also are intended to embrace "haloalkyl." The term "optionally substituted" as it refers to "alkyl" herein indicates that the alkyl group also may be substituted at one or more, usually only one, substitutable position by one or more groups independently selected from halo (preferably fluoro), alkoxy (haloalkoxy), aryloxy, amino, hydroxy, nitro, cyano, thiol, alkylthio, aryl, heteroaryl, heterocyclo and carbocyloalkyl.

The related term "alkylene" as used alone or in combination in any of the formulae herein, refers to an optionally substituted straight or branched chain saturated divalent hydrocarbon group containing from one to ten carbon atoms. Preferably, the alkylene group is a "$C_{1-6}$ alkylene" or "lower alkylene" which refer to such groups containing from one to six carbon atoms, such as methylene, ethylene, n-propylene, isopropylene, n-butylene, isobutylene, sec-butylene, tert-butylene and the like. The term "optionally substituted" as it refers to "alkylene" herein indicates that the alkylene group also may be substituted at one or more, usually only one, substitutable position by one or more groups independently selected from alkyl, halo and aryl.

The term "alkoxy" as used alone or in combination in any of the formulae herein refers to a straight or branched chain alkyl group covalently bonded to the parent structure through an —O— linkage containing from one to ten carbon atoms and the terms "$C_{1-6}$ alkoxy" and "lower alkoxy" refer to such groups containing from one to six carbon atoms, such as methoxy, ethoxy, propoxy, isopropoxy, butoxy, t-butoxy, trifluoromethoxy and the like.

The term "alkoxyalkyl" refers to an alkyl group substituted with an alkoxy group.

The term "haloalkyl" is a substituted alkyl, preferably a substituted lower alkyl, substituted with one or more halogen atoms, and preferably is a $C_1$ to $C_4$ alkyl substituted with one to three halogen atoms. One preferred example of a haloalkyl is trifluoromethyl.

The term "alkanoyl" as used alone or in combination in any of the formulae herein refers to an acyl radical derived from an alkanecarboxylic acid, particularly a lower alkanecarboxylic acid, and includes such examples as acetyl, propionyl, butyryl, valeryl, and 4-methylvaleryl.

The term "aminocarbonyl" means an amino-substituted carbonyl (carboxamide) wherein the amino group can be a primary, secondary (mono-substituted amino) or tertiary amino (di-substituted amino) group preferably having as a substituent(s) a lower alkyl, or an aryl.

The term "carbocycloalkyl" in any of the formulae herein refers to an optionally substituted, stable, saturated or partially unsaturated monocyclic, bridged monocyclic, bicyclic, and spiro ring hydrocarbons of 3 to 15 carbon atoms such as cyclopropyl, cyclobutyl, cyclopentyl, cyclohexyl, cycloheptyl, bicyclohexyl, bicyclooctyl, bicyclononyl, spirononyl and spirodecyl. The term "optionally substituted" as it refers to "carbocycloalkyl" herein indicates that the carbocycloalkyl group may be substituted at one or more substitutable ring positions by one or more groups independently selected from alkyl (preferably lower alkyl), aralkyl, alkoxy (preferably lower alkoxy), nitro, cyano, halo (preferably fluoro), haloalkyl (preferably trifluoromethyl), alkanoyl, aminocarbonyl, monoalkylaminocarbonyl, dialkylaminocarbonyl, alkoxyalkyl (preferably a lower alkoxy[lower]alkyl), alkoxycarbonyl (preferably a lower alkoxycarbonyl), alkylcarbonyloxy (preferably a lower alkylcarbonyloxy), alkenyl, heterocyclo, heteroaryl, amino (preferably a lower alkylamino, or a di[lower]alkylamino), carbocycloalkyl, thiol, alkylthio, arylthio, aryloxy, arylsulfonylamino, alkylsulfonylamino, arylcarbonylamino, alkylcarbonylamino, hydroxy, haloalkoxy and aryl (preferably phenyl), said aryl being optionally substituted by halo (preferably fluoro), lower alkyl (prfeferably methyl) and lower alkoxy groups (preferably methoxy).

The term "heterocyclo" as used in any of the formulae herein refers to optionally substituted stable, saturated, or partially unsaturated, monocyclic, bridged monocyclic, bicyclic, and spiro ring systems containing carbon atoms and other atoms selected from nitrogen, sulfur and/or oxygen. Preferably, a heterocyclo is an optionally substituted 5 or 6-membered monocyclic ring or an optionally substituted 8–11-membered bicyclic ring which consists of carbon atoms and contains one, two, or three heteroatoms selected from nitrogen, oxygen and/or sulfur. The term "optionally substituted" as it refers to "heterocyclo" herein indicates that the heterocyclo group may be substituted at one or more substitutable ring positions by one or more groups independently selected from alkyl (preferably lower alkyl), aralkyl, alkoxy (preferably lower alkoxy), nitro, cyano, halo (preferably fluoro), haloalkyl (preferably trifluoromethyl), alkanoyl, aminocarbonyl, monoalkylaminocarbonyl, dialkylaminocarbonyl, alkoxyalkyl (preferably a lower alkoxy[lower]alkyl), alkoxycarbonyl (preferably a lower alkoxycarbonyl), alkylcarbonyloxy (preferably a lower alkylcarbonyloxy), alkenyl, heterocyclo, heteroaryl, amino (preferably a lower alkylamino, or a di[lower]alkylamino), carbocycloalkyl, thiol, alkylthio, arylthio, aryloxy, arylsulfonylamino, alkylsulfonylamino, arylcarbonylamino, alkylcarbonylamino, hydroxy, haloalkoxy and aryl (preferably phenyl), said aryl being optionally substituted by halo (preferably fluoro), lower alkyl (preferably methyl) and lower alkoxy (preferably methoxy) groups. The heterocyclo group may be attached to the parent structure through a carbon atom or through any heteroatom of the heterocyclo that results in a stable structure. Examples of such heterocyclo groups are:

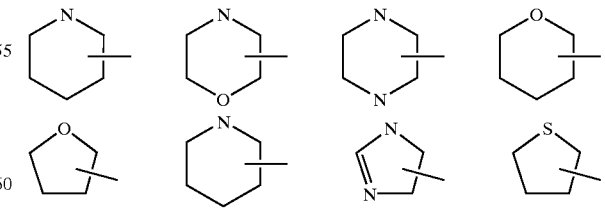

The term "heteroaryl" as used in any of the formulae herein refers to an optionally substituted stable, aromatic monocyclic or bicyclic ring system containing carbon atoms and other atoms selected from nitrogen, sulfur and/or oxygen. Preferably, a heteroaryl is an optionally substituted 5 or 6-membered monocyclic ring (optionally benzofused) or an 8–11 membered bicyclic ring which consists of carbon atoms and contains one, two, or three heteroatoms selected from nitrogen, oxygen and/or sulfur. The term "optionally substituted" as it refers to "heteroaryl" herein indicates that the heteroaryl group may be substituted at one or more substitutable ring positions by one or more groups independently selected from alkyl (preferably lower alkyl), aralkyl, alkoxy (preferably lower alkoxy), nitro, cyano, halo (preferably fluoro), haloalkyl (preferably trifluoromethyl), alkanoyl, aminocarbonyl, monoalkylaminocarbonyl, dialkylaminocarbonyl, alkoxyalkyl (preferably a lower alkoxy[lower]alkyl), alkoxycarbonyl (preferably a lower alkoxycarbonyl), alkylcarbonyloxy (preferably a lower alkylcarbonyloxy), alkenyl, heterocyclo, heteroaryl, amino (preferably a lower alkylamino, or a di[lower]alkylamino), carbocycloalkyl, thiol, alkylthio, arylthio, aryloxy, arylsulfonylamino, alkylsulfonylamino, arylcarbonylamino, alkylcarbonylamino, hydroxy, haloalkoxy and aryl (preferably phenyl), said aryl being optionally substituted by halo (preferably fluoro), lower alkyl (preferably methyl) and lower alkoxy (preferably methoxy) groups. Examples of such heteroaryl groups are:

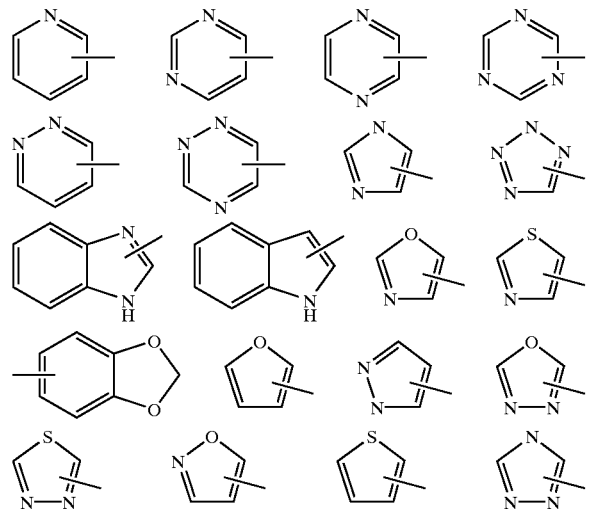

Imidazolyls and pyridyls are preferred. Several examples of imidazolyls are:

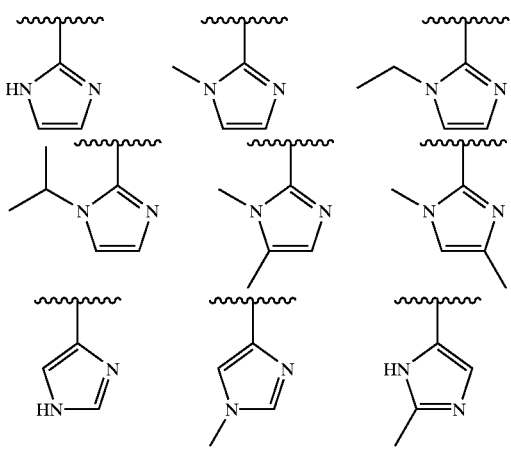

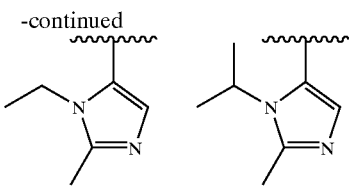

Several examples of pyridyls are:

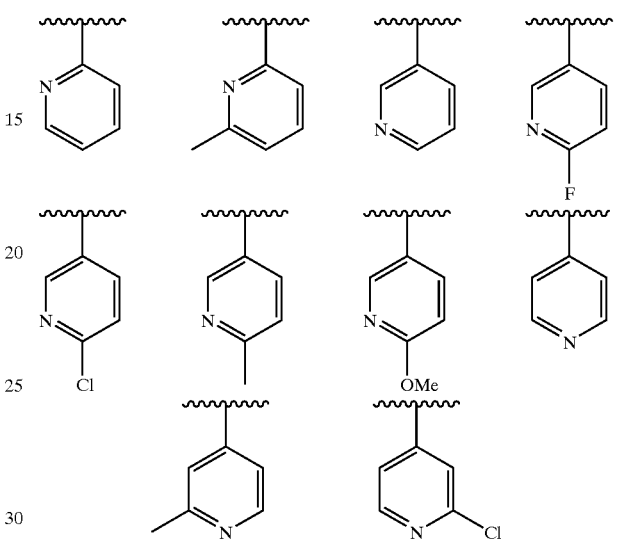

The heteroaryl group may be attached to the parent structure through a carbon atom or through any heteroatom of the heteroaryl that results in a stable structure.

The term "heteroaralkyl" as used herein refers to a lower alkyl as defined above in which one hydrogen atom is replaced by an optionally substituted heteroaryl radical as defined above. The term "optionally substituted" as it refers to "heteroaralkyl" herein indicates that the heteroaryl group may be substituted at one or more substitutable ring positions by one or more groups independently selected from alkyl (preferably lower alkyl), aralkyl, alkoxy (preferably lower alkoxy), nitro, cyano, halo (preferably fluoro), haloalkyl (preferably trifluoromethyl), alkanoyl, aminocarbonyl, monoalkylaminocarbonyl, dialkylaminocarbonyl, alkoxyalkyl (preferably a lower alkoxy[lower]alkyl), alkoxycarbonyl (preferably a lower alkoxycarbonyl), alkylcarbonyloxy (preferably a lower alkylcarbonyloxy), alkenyl, heterocyclo, heteroaryl, amino (preferably a lower alkylamino, or a di[lower]alkylamino), carbocycloalkyl, thiol, alkylthio, arylthio, aryloxy, arylsulfonylamino, alkylsulfonylamino, arylcarbonylamino, alkylcarbonylamino, hydroxy, haloalkoxy and aryl (preferably phenyl), said aryl being optionally substituted by halo (preferably fluoro), lower alkyl (preferably methyl) and lower alkoxy (preferably methoxy) groups. Examples of such heteroaralkyl groups are 2-pyridylmethyl, 3-pyridylmethyl, 4-pyridylmethyl, 3-pyridylethyl and 4-pyrimidinylmethyl.

The terms "halo" and "halogen" as used in any of the formulae herein to identify substituent moieties, represent fluorine, chlorine, bromine or iodine, preferably chlorine or fluorine, and more preferably fluorine.

The term "aryl" when used alone or in combination in any of the formulae herein refers both to an unsubstituted or an optionally substituted monocyclic or bicyclic aromatic hydrocarbon ring system. Preferred are optionally substituted phenyl or naphthyl groups. The aryl group may optionally be substituted at one or more substitutable ring positions by one or more groups independently selected from alkyl (preferably lower alkyl, and more preferably methyl), aralkyl, alkoxy (preferably lower alkoxy and more preferably methoxy), nitro, cyano, halo (preferably fluoro), haloalkyl (preferably trifluoromethyl), alkanoyl, aminocarbonyl, monoalkylaminocarbonyl, dialkylaminocarbonyl, alkoxyalkyl (preferably a lower alkoxy[lower]alkyl), alkoxycarbonyl (preferably a lower alkoxycarbonyl), alkylcarbonyloxy (preferably a lower alkylcarbonyloxy), alkenyl, heterocyclo, heteroaryl, amino (preferably a lower alkylamino, or a di[lower]alkylamino), carbocycloalkyl, thiol, alkylthio, arylthio, aryloxy, arylsulfonylamino, alkylsulfonylamino, arylcarbonylamino, alkylcarbonylamino, hydroxy, haloalkoxy and aryl (preferably phenyl), said aryl being optionally substituted by halo, lower alkyl and lower alkoxy groups. Preferably, the aryl group is phenyl optionally substituted with up to four and usually with one or two groups, preferably selected from $C_{1-6}$ alkyl, $C_{1-6}$ alkoxy, as well as cyano, trifluoromethyl and halo.

The term "aralkyl" alone or in combination refers to a lower alkyl radical as defined above in which one hydrogen atom is replaced by an aryl radical as defined above, and includes benzyl, and 2-phenylethyl. The aralkyl group may optionally be substituted at one or more substitutable ring positions by one or more groups independently selected from alkyl (preferably lower alkyl), aralkyl, alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "alkoxycarbonyl" alone or in combination means a radical of the formula —C(O)-alkoxy, in which alkoxy is as defined above.

The term "alkylcarbonyloxy" alone or in combination means a radical of the formula —O—C(O)-alkyl, in which alkyl is as defined above.

The term "alkenyl" means a two to seven carbon, straight or branched hydrocarbon containing one or more double bonds, preferably one or two double bonds. Examples of alkenyl include ethenylene, propenylene, 1,3-butadienyl, and 1,3,5-hexatrienyl.

The term "amino" refers to both unsubstituted amino (NH$_2$), as well as mono-substituted amino groups of the formula NHZ' and di-substituted amino groups of the formula NZ'Z", wherein Z' and Z" are independently selected from the group consisting of alkyl (preferably lower alkyl and more preferably methyl), carbocycloalkyl, aryl, heteroaryl and heterocyclo, or Z' and Z" taken together with the nitrogen atom to which they are attached form a heterocyclic ring. Preferred aminos are the unsubstituted amino and aminos substituted with one or two alkyl substituents, preferably lower alkyl substituents and more preferably methyls.

The term "thiol" means —SH.

The term "alkylthio" is a thiol group having the hydrogen replaced with an alkyl group as hereinabove defined.

The term "arylthio" is a thiol group having the hydrogen replaced with an aryl group as hereinabove defined.

The term "aryloxy" refers to an aryl group as hereinabove defined bonded to the parent structure through an —O— linkage.

The term "arylsulfonylamino" refers to the structure —(NH)—(SO$_2$)-Aryl, with the aryl group as hereinabove defined.

The term "alkylsulfonylamino" refers to the structure —NH)—(SO$_2$)-Alkyl, with the alkyl group as hereinabove defined.

The term "arylcarbonylamino" refers to the structure —NH)—(CO)-Aryl, with the aryl group as hereinabove defined.

The term "alkylcarbonylamino" refers to the structure —(NH)—(CO)-Alkyl, with the alkyl group as hereinabove defined.

The term "hydroxy" means —OH.

The term "haloalkoxy" is a haloalkyl bonded to the parent structure through an —O— linkage.

The specific chemical nature of the optionally substituted heterocyclo, heteroaryl and aryl groups for the terminal moieties $R^1$, $R^2$ and $R^3$ in the prior identified potassium channel inhibitor compounds is not narrowly critical and, as noted above, a wide variety of substituent groups are contemplated. Preferably, the optional substituents for the heterocyclo, heteroaryl, and aryl groups are selected such that the total number of carbon and hetero (oxygen, nitrogen and sulfur) atoms comprising the optionally substituted heterocyclos, heteroaryls and aryls is no more than about 25, preferably no more than about 15.

The phrase "substituted carbon atom" used in connection with the variables A, B and D of the general formulae above means a ring carbon substituted with hydrogen, alkyl, halo, nitro, cyano, or amino.

The term "treating" as used herein, describes the management and care of a patient afflicted with a condition, disease or disorder for which the administration of a compound of the present invention alters the action or activity of a potassium channel to prevent the onset of symptoms or complications associated with the condition, disease or disorder, to alleviate the symptoms or complications caused by the condition, disease or disorder, or to eliminate the condition, disease or disorder altogether.

It is recognized that there may be one or more chiral centers in the compounds falling within the scope of the present invention and thus such compounds will exist as various stereoisomeric forms Applicants intend to include all the various stereoisomers within the scope of the invention, referred to herein as the "pharmaceutically acceptable stereoisomers". Thus, this invention is intended to include cis and trans isomers, the enantiomers and the diastereoisomers of the compounds. Though the compounds may be prepared as racemates and can conveniently be used as such, individual optical isomers and diastereoisomers also can be isolated or preferentially synthesized by known techniques if desired. Such individual optical isomers and mixtures thereof (racemates and diastereoisomers) are intended to be included within the scope of the present invention.

The present invention also encompasses the pharmaceutically acceptable esters, amides, complexes, chelates, hydrates, crystalline or amorphous forms, metabolites, metabolic precursors or prodrugs of the compounds described above. Pharmaceutically acceptable esters and amides can be prepared by reacting, respectively, a hydroxy or amino functional group with a pharmaceutically acceptable organic acid, such as identified below. A prodrug is a drug which has been chemically modified and may be biologically inactive at its site of action, but which is degraded or modified by one or more enzymatic or other in vivo processes to the parent bioactive form. Generally, a prodrug has a different pharmacokinetic profile than the parent drug such that, for example, it is more easily absorbed across the mucosal epithelium, it has better salt formation or solubility and/or it has better systemic stability (e.g., an increased plasma half-life).

Those skilled in the art recognize that chemical modifications of a parent drug to yield a prodrug may include: (1) terminal ester or amide derivatives which are susceptible to being cleaved by esterases or lipases; (2) terminal peptides which may be recognized by specific or nonspecific proteases; or (3) a derivative that causes the prodrug to accumulate at a site of action through membrane selection, and combinations of the above techniques. Conventional procedures for the selection and preparation of prodrug derivatives are described in H. Bundgaard, *Design of Prodrugs*, (1985). Those skilled in the art are well-versed in the preparation of prodrugs and are well-aware of its meaning.

The compounds of the present invention can be used in their neat form or in the form of pharmaceutically-acceptable salts derived from inorganic or organic acids. In the practice of the present invention, compounds of the present invention in their neat form generally will have a molecular weight of 800 or below, usually a molecular weight of 600 or below. Examples of acids which may be employed to form pharmaceutically acceptable acid addition salts of compounds of the present invention include such inorganic acids as hydrochloric acid, sulphuric acid and phosphoric acid and such organic acids as maleic acid, succinic acid and citric acid. These salts thus include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide hydroiodide, 2-hydroxy-ethanesulfonate, lactate, maleate, methanesulfonate, nicotinate, 2-naphthalenesulfonate, palmoate, pectinate, persulfate, 3-phenylpropionate, picrate, pivalate, propionate, succinate, tartrate, thiocyanate, p-toluenesulfonate and undecanoate.

Also, the basic nitrogen-containing groups can be quaternized with such agents as lower alkyl halides, such as methyl, ethyl, propyl, and butyl chlorides, bromides and iodides; dialkyl sulfates, like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil soluble or dispersible products are thereby generally obtained.

The pharmaceutically acceptable salts of the compounds of the present invention also can exist as various solvates, such as with water, methanol, ethanol, dimethylformamide, ethyl acetate and the like. Mixtures of such solvates also can be prepared. Such solvates are within the scope of the present invention.

The pharmacological profile of the potassium channel inhibitory activity of the compounds of the present invention can be readily assessed by those skilled in the art using routine experimentation, such as the procedures and techniques illustrated in the examples which follow. Assays for assessing the activity of particular compounds may employ cells stably transfected to express a specific potassium channel, as well as native mammalian cells. In particular, cells stably transfected to express a specific potassium channel, which have been treated with a voltage dependent fluorescent dye, such as bis-(1,3-dibutylbarbituric acid) trimethine oxonol, can be used to gauge the inhibitory activity of potassium channel inhibitor compounds, possibly in comparison to known inhibitors. Alternatively, such cells can be primed with a detectible species, such as $^{86}$Rb, and then challenged with a particular compound, under conditions otherwise suitable for activating the potassium channel, to assess the potassium inhibitory activity of the compound. The potassium channel inhibitory activity of a compound also can be determined using isolated mammalian cells and the whole cell configuration of the known patch clamp technique (Hamill et al., *Pflugers Archiv* 391:85, 1981). These and other known techniques can be readily employed by those skilled in the art to assess the activity level of the potassium channel inhibitor compounds of the present invention.

The compounds of the present invention may be administered by a variety of routes including orally, parenterally, sublingually, intranasally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intracardiac injection, or infusion techniques. Topical administration may also involve the use of transdermal administration such as transdermal patches or iontophoresis devices.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,2-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and perfuming agents.

The compounds of the present invention can also be administered in the form of liposomes. As is known in the art, liposomes are generally derived from phospholipids or other lipid substances. Liposomes are formed as mono- or multi-lamellar hydrated liquid crystals that are dispersed in an aqueous medium. Any non-toxic physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33, et seq.

To select preferred compounds from less preferred compounds, one uses by example the in vitro assays detailed under the sub-heading BioAssays hereafter. Typically, a preferred compound will produce half maximal inhibition of the steady-state current at a concentration ranging from about 1 nM to about 1 $\mu$M along with a potentially physiologically significant amount of peak current inhibition at the same concentration in electrophysiolgial studies (see Table 3). One of ordinary skill will recognize that the final and optimum dose and regimen will be determined empirically for any given drug.

Total daily dose administered to a host in single or divided doses may be an amount, for example, from 0.001 to 100 mg of active ingredient per kg body weight on a daily basis and more usually 0.01 to 10 mg/kg/day. Dosage unit compositions may contain such amounts of submultiples thereof to make up the daily dose. It is anticipated that a therapeutically effective serum concentration of active ingredient will be 10 nM to 10 $\mu$M (5 ng/ml to 5 $\mu$g/ml).

The amount of active ingredient that may be combined with carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, and diet of the patient, the time of administration, the route of administration, the rate of excretion, whether a drug combination is used, and the severity of the particular disease.

The present inventors have identified compounds that are open channel blockers of human Kv1.5 potassium channels and exhibit surprising peak current inhibitory activity. As shown in FIG. 1, compounds that are open channel blockers of human Kv1.5 potassium channels exert little or no blocking activity until the channel is activated. Following channel activation, block develops until steady-state inhibition is achieved. The time taken for steady-state inhibition to be achieved is a function of the compound "on-rate." The data represented by FIG. 1 is characteristic of prior art compounds, such as those described in WO 99/37607.

Figure 2:
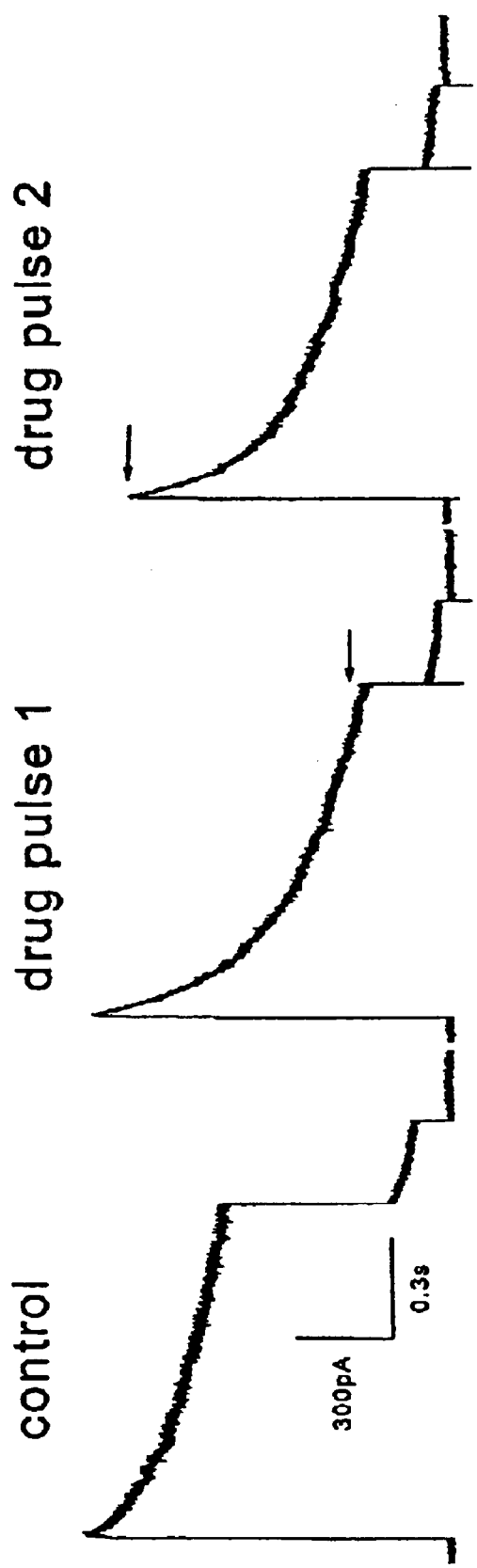
FIG. 2 shows the typical result of eliciting Kv1.5 currents with 1 s voltage steps to 0 mV (from a holding potential of −80 mV) before (control) and 2 min after application of 0.1 $\mu$M of a prior art compound, such as those described in WO 99/37607 (drug pulse 1). Drug pulse 2 was recorded 10 s after drug pulse 1, in the continued presence of 0.1 $\mu$M of the prior art compound. Note that for such compounds, peak current in the presence of drug is similar to peak current under control conditions.

Following channel closure, such compounds dissociate from the channel at a rate determined by the compound "off-rate." If the compound off-rate is rapid, as is characteristic of certain prior art compounds, significant recovery from block will occur during the interpulse interval (i.e. when the channel is closed) and the magnitude of the initial current elicited by a subsequent depolarization (see arrow, drug pulse 2, FIG. 2) will be large relative to the current at the end of the preceding pulse (see arrow drug pulse 1, FIG. 2). For these compounds, peak current in the presence of the compound is similar to peak current under control conditions (FIG. 2).

Figure 3:
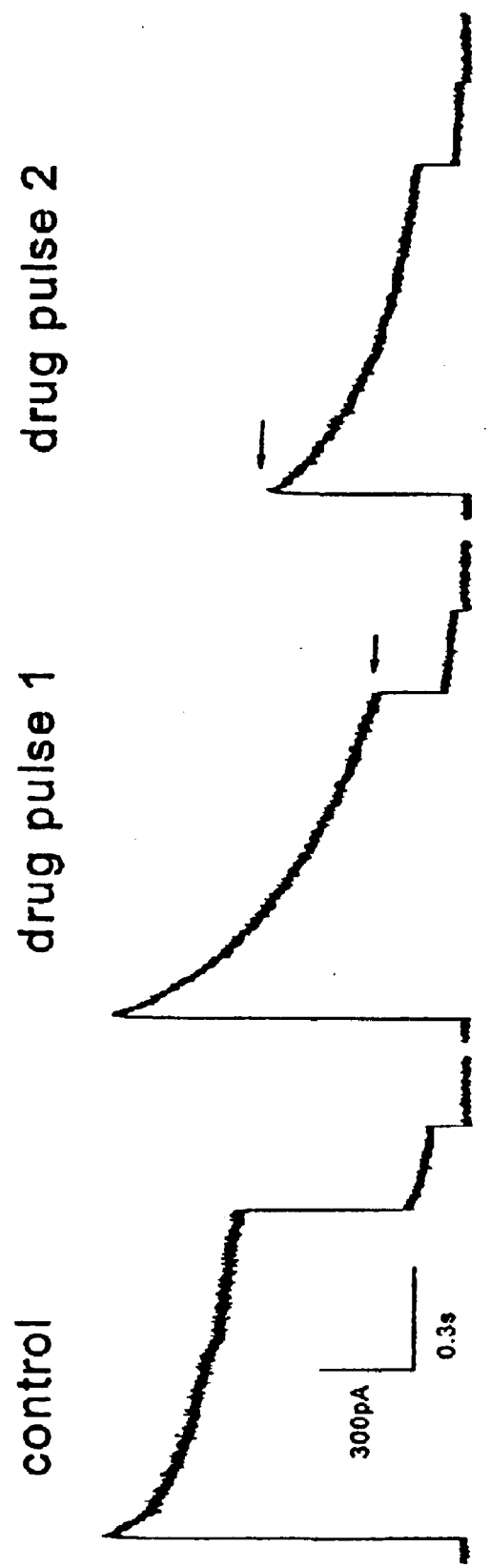
FIG. 3 shows the typical result of eliciting Kv1.5 currents with 1 s voltage steps to 0 mV(from a holding potential of −80 mV) before (control) and 2 min after application of 0.1 $\mu$M of a compound representative of the present invention (drug pulse 1). Drug pulse 2 was recorded 10 s after drug pulse 1. In the continued presence of 0.1 $\mu$M of the compound, the system exhibits peak current inhibition.
Figure 4:
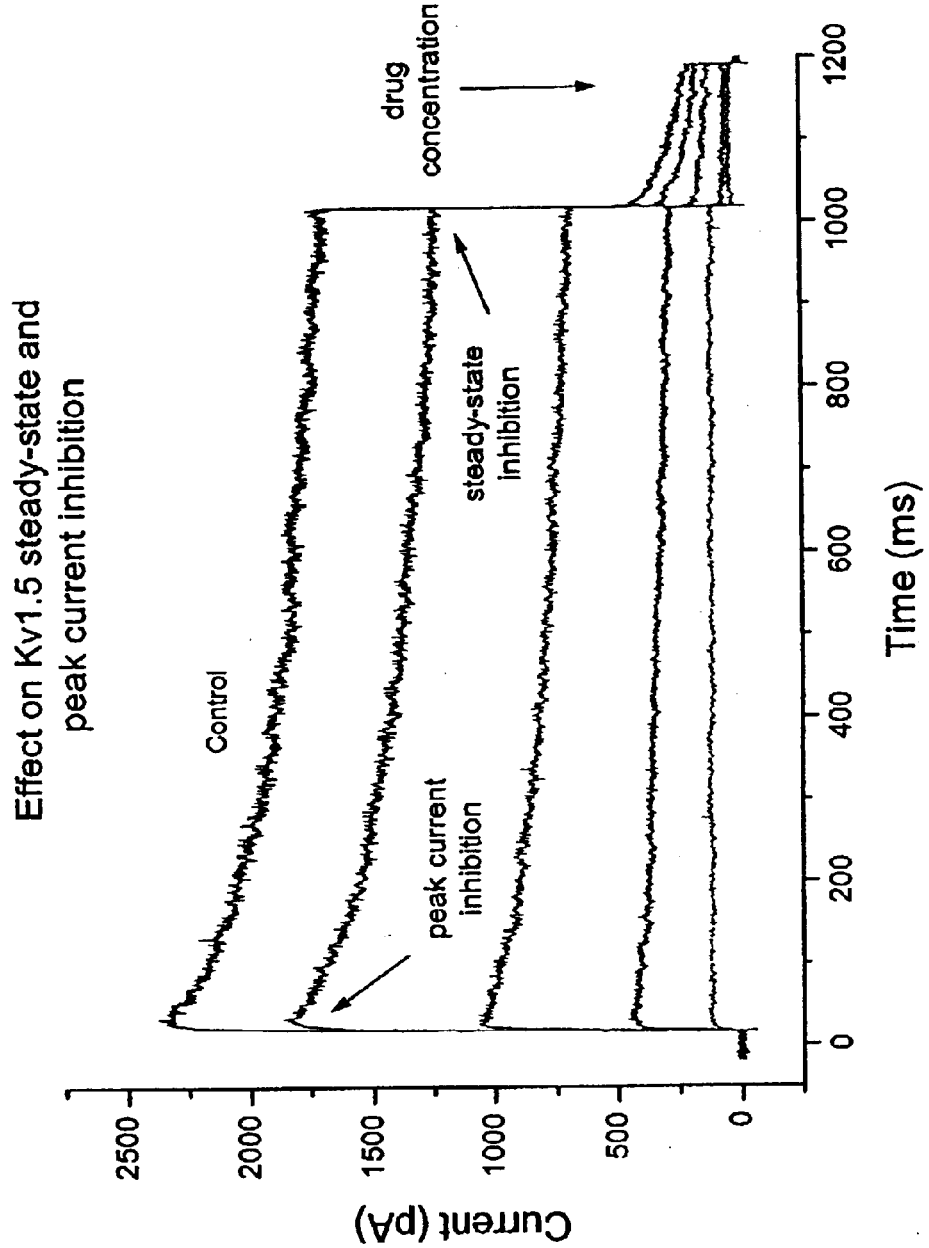
FIG. 4 shows hKv1.5 currents that were recorded using the whole-cell voltage clamp technique.
Figure 5:
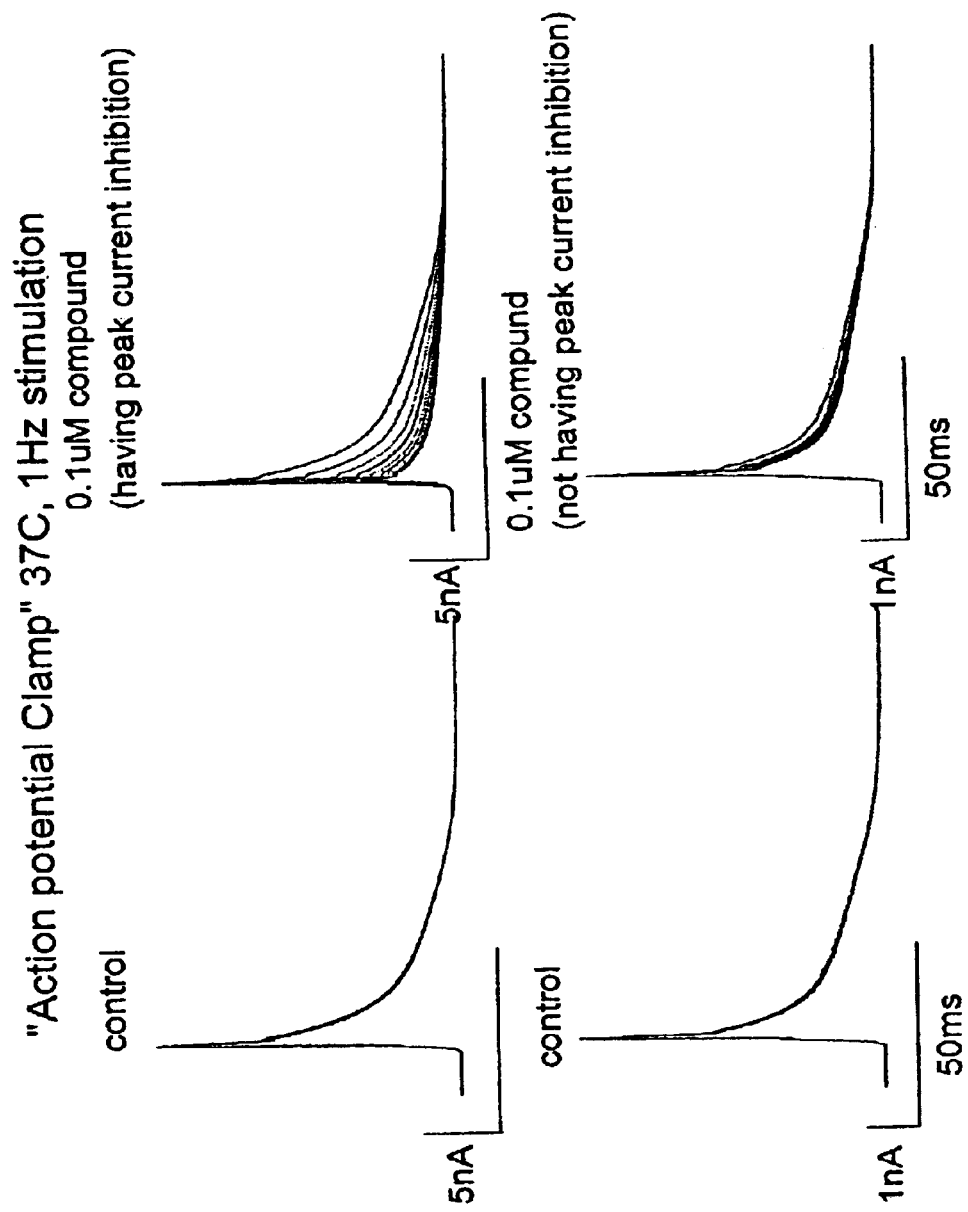
FIG. 5 shows the Kv1.5 currents elicited using a human action potential waveform as the voltage command in whole-cell voltage-clamp experiments with CHO cells stably expressing hKv1.5

For compounds with slow off-rates however, such as those characteristic of the present invention, little recovery from block occurs during the interpulse interval, and the magnitude of the peak current elicited by a subsequent depolarization (see arrow, drug pulse 2, FIG. 3) will be similar to the current at the end of the preceding pulse (see arrow drug pulse 1, FIG. 3). For these compounds, peak current in the presence of the compound is very much smaller than the peak current under control conditions (FIG. 3), i.e., these compounds exhibit peak current inhibition. The property of peak current inhibition characteristic of the compounds of the present invention was entirely unexpected. FIG. 4 illustrates the unexpected property of peak current inhibition at increasing compound concentrations. Blockers with slow off-rates produce optimal Kv1.5 block under physiological conditions (FIG. 5). Blockers with slow off-rates also prolong human atrial action potential duration under physiological conditions.

Representative Compounds

Table 1 illustrates individually selected compounds of the present invention, each of which is embraced by one or more of the previously identified formulae (in the following structures an open-ended bond represents a methyl group):

TABLE 1

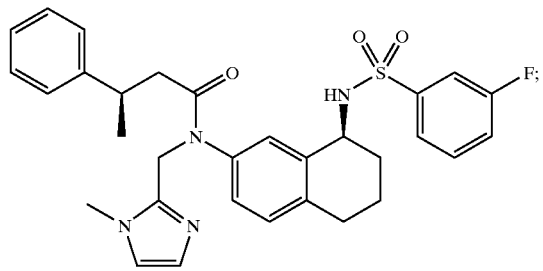

(1)

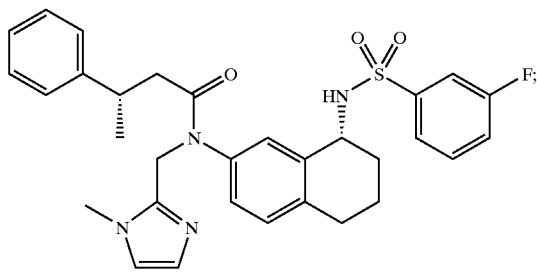

(2)

TABLE 1-continued
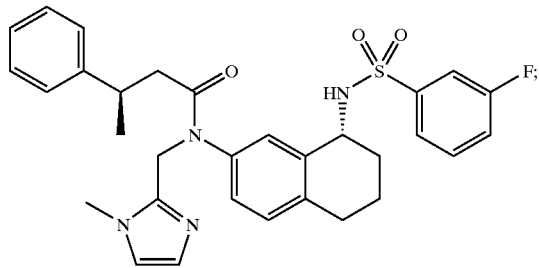
(3)
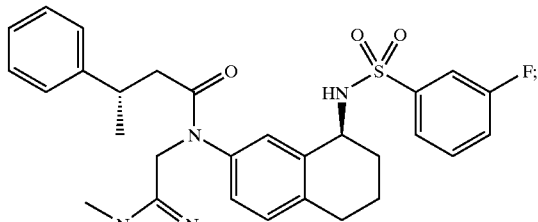
(4)
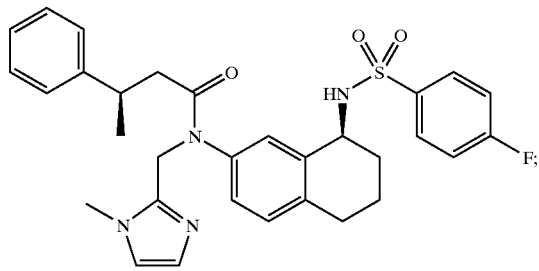
(5)
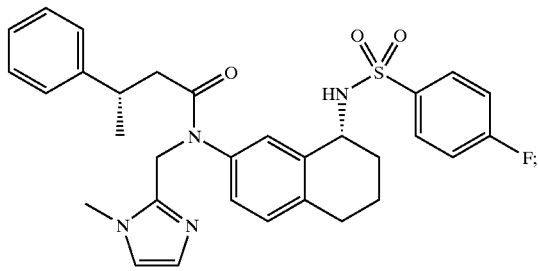
(6)
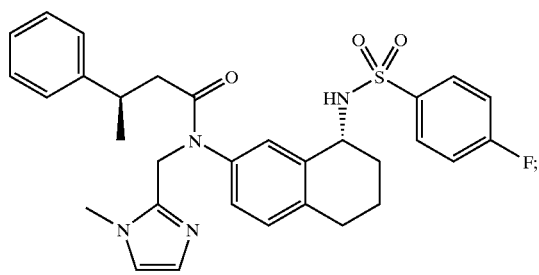
(7)
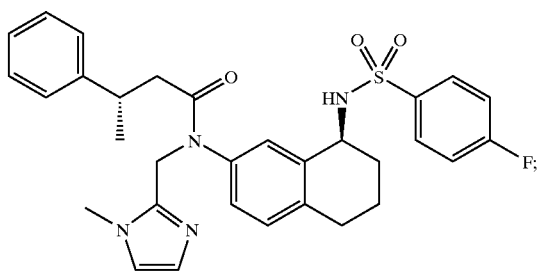
(8)
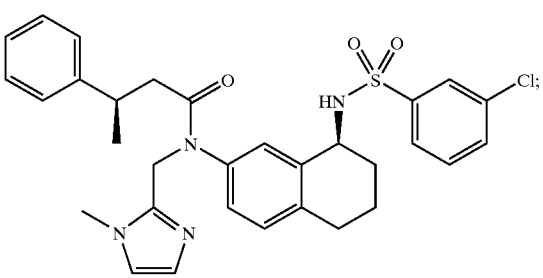
(9)
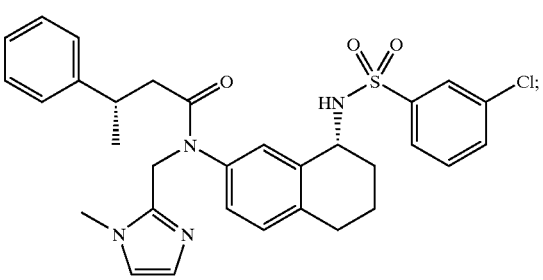
(10)
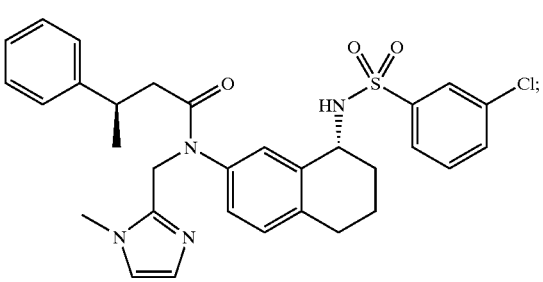
(11)
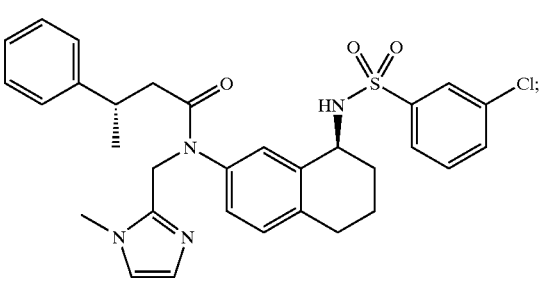
(12)

TABLE 1-continued
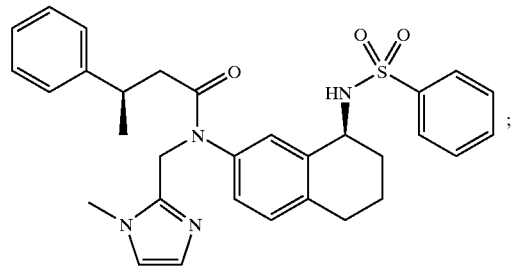
(13)
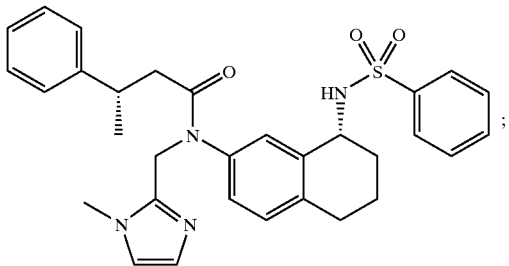
(14)
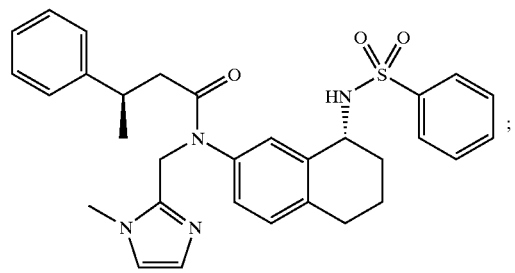
(15)
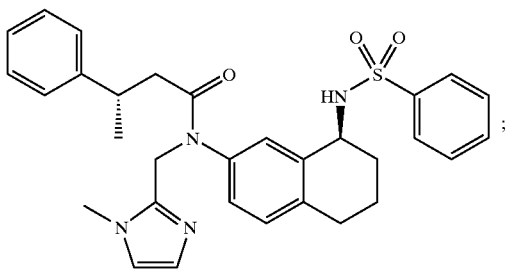
(16)
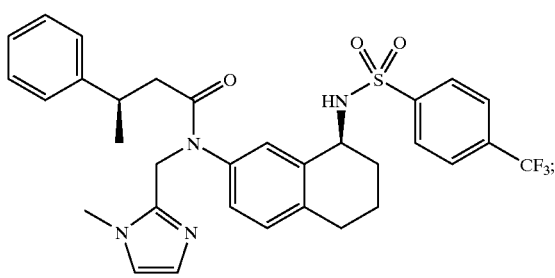
(17)
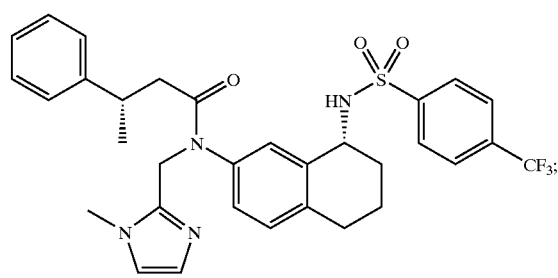
(18)
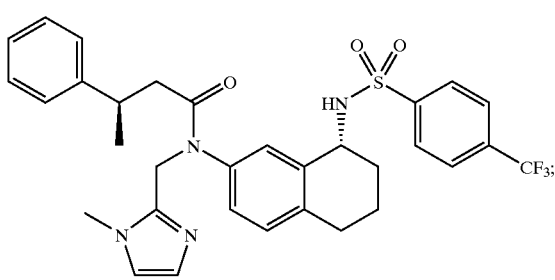
(19)
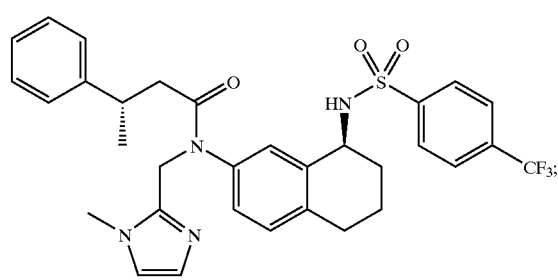
(20)
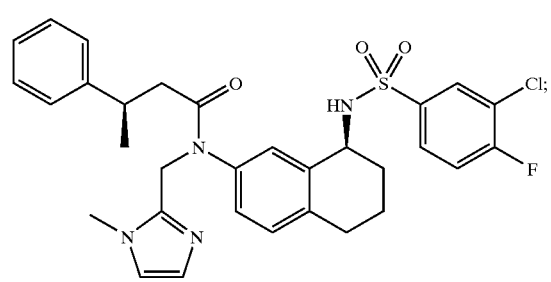
(21)
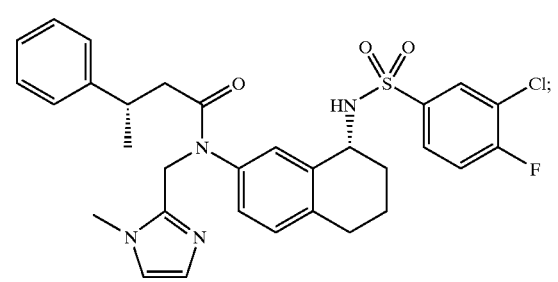
(22)

TABLE 1-continued
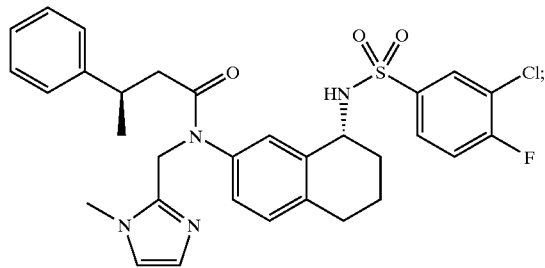
(23)
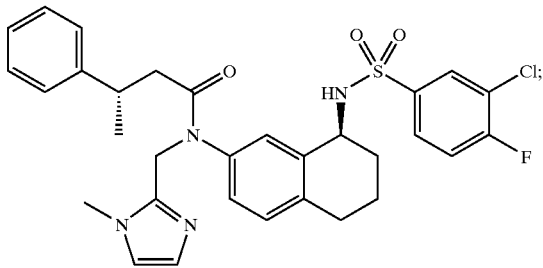
(24)
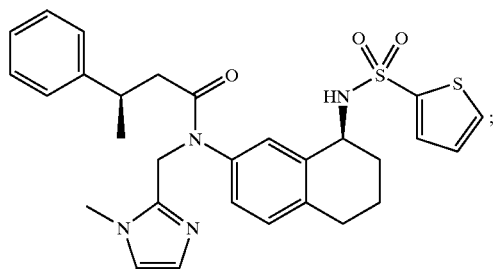
(25)
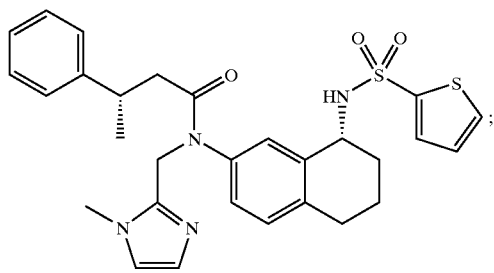
(26)
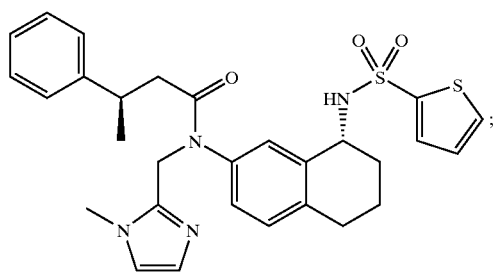
(27)
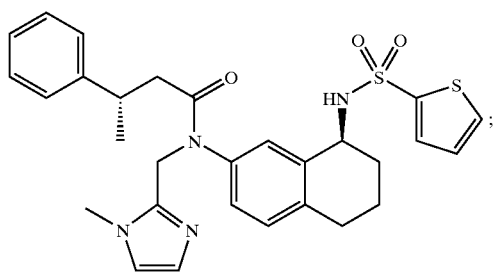
(28)
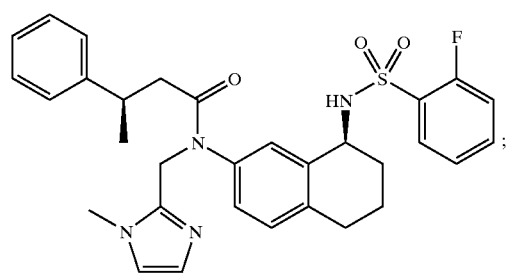
(29)
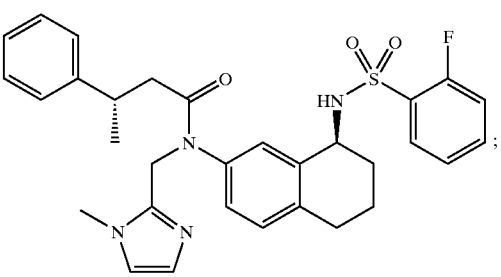
(30)
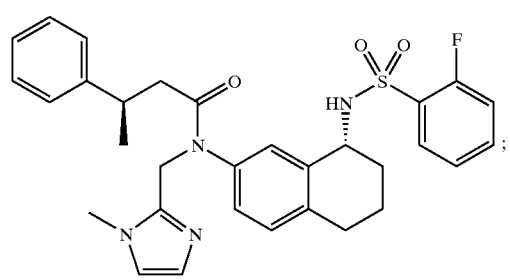
(31)
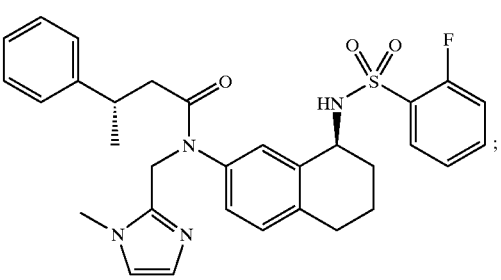
(32)

TABLE 1-continued
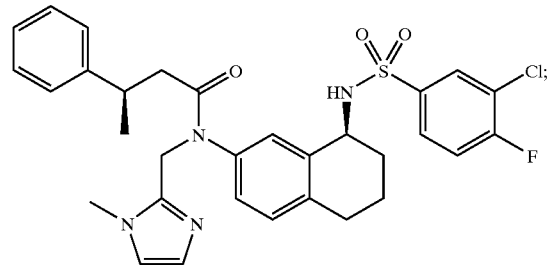
(33)
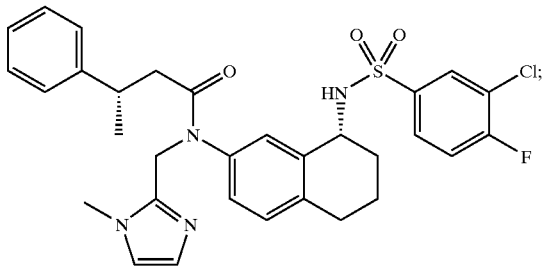
(34)
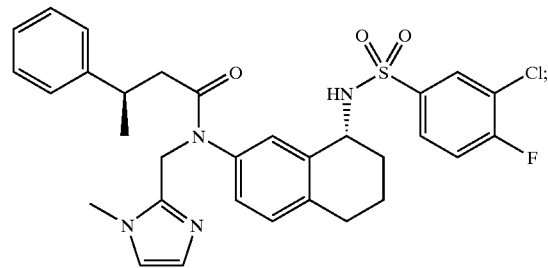
(35)
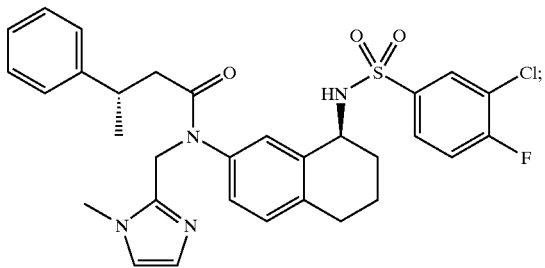
(36)
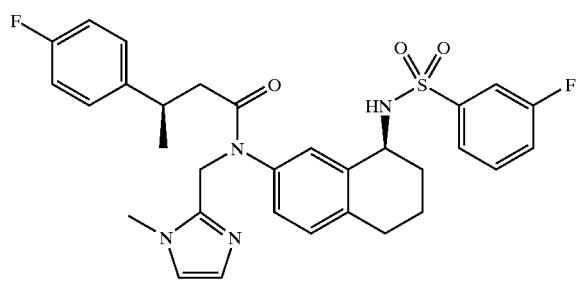
(37)
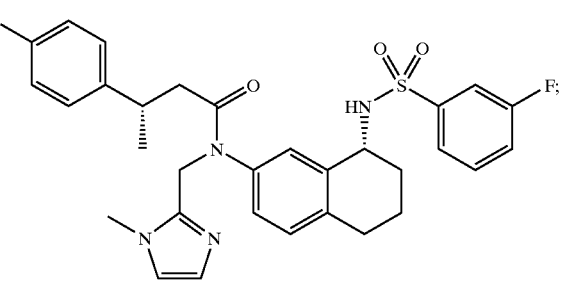
(38)
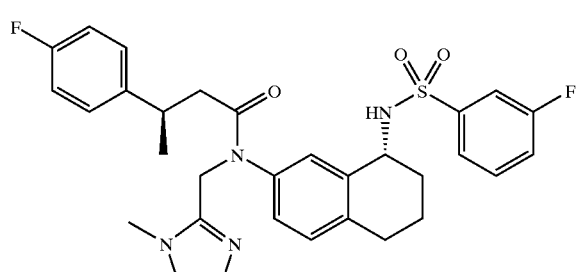
(39)
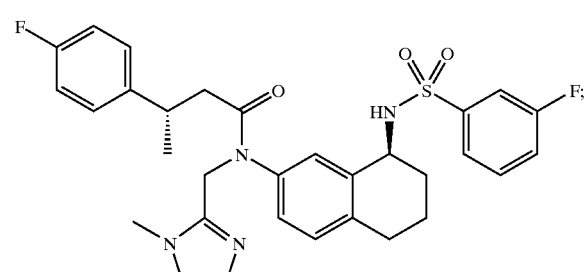
(40)
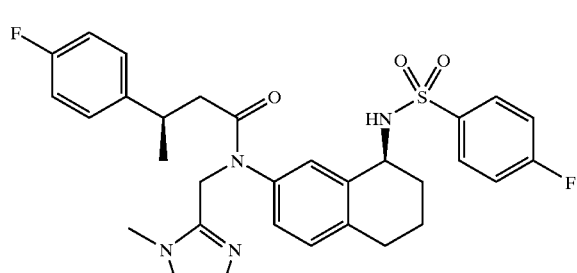
(41)
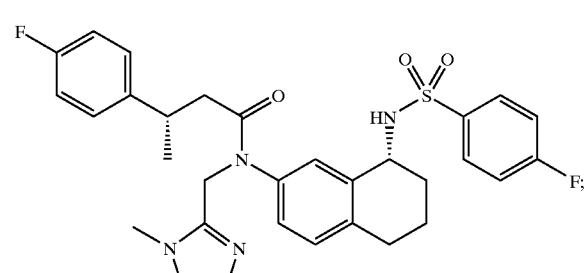
(42)

TABLE 1-continued
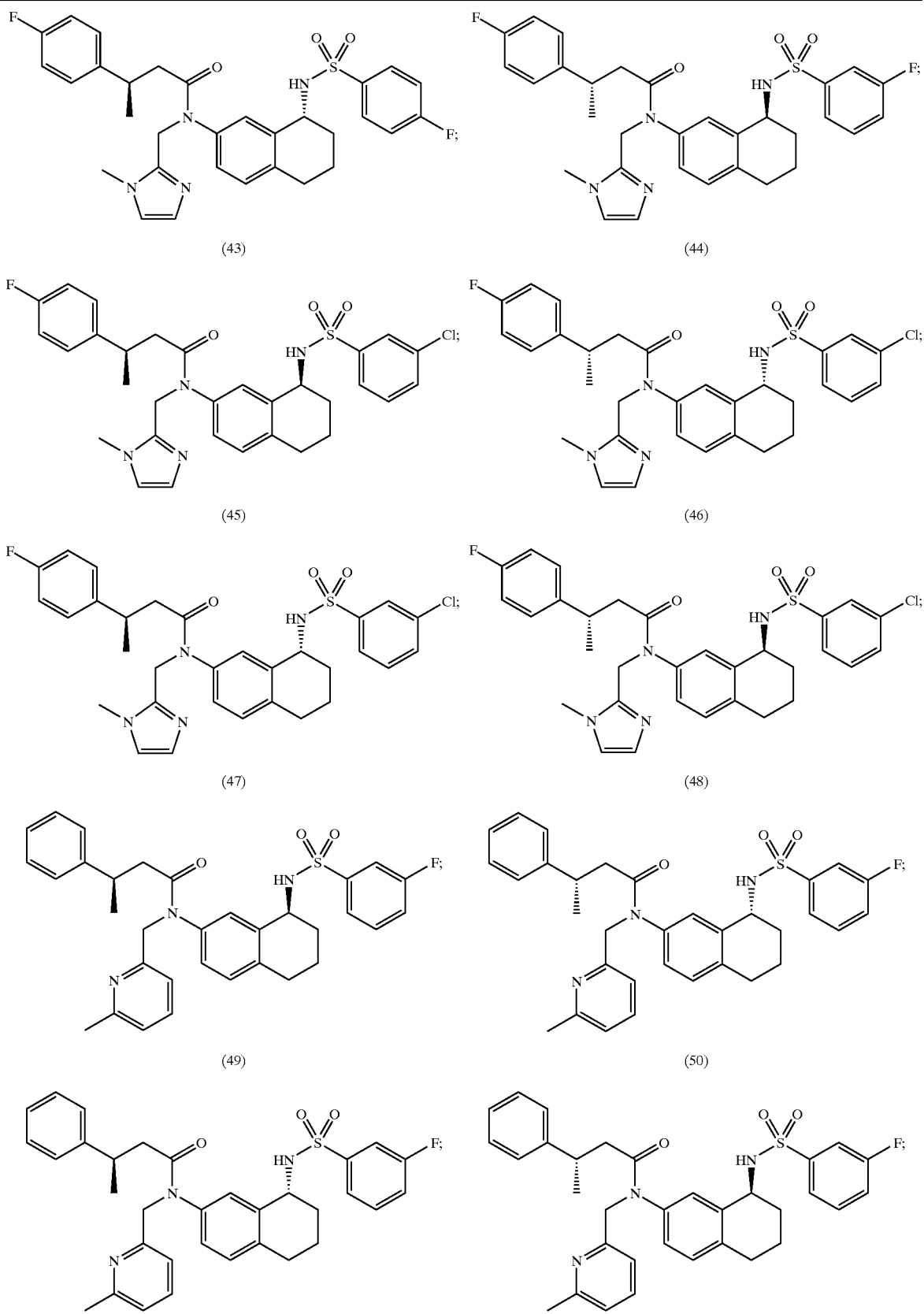

TABLE 1-continued
(51)
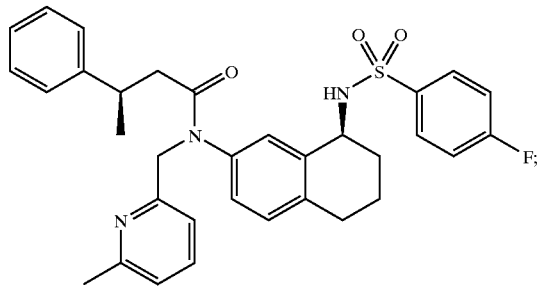
(52)
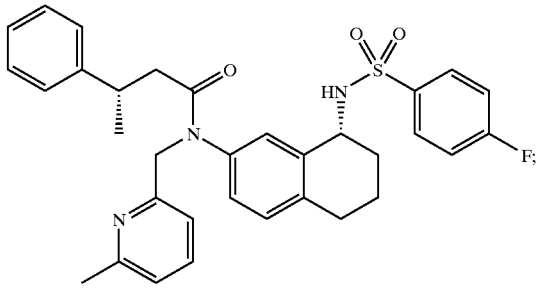
(53)
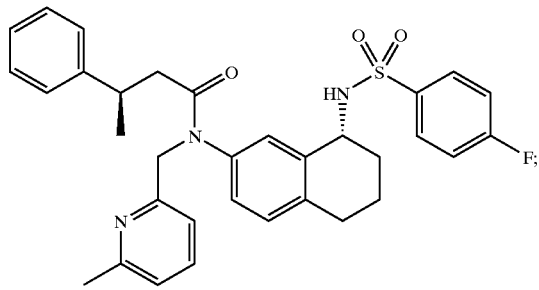
(54)
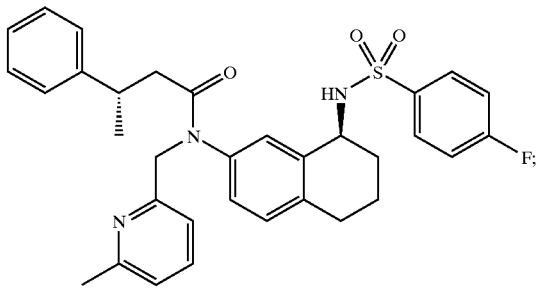
(55)
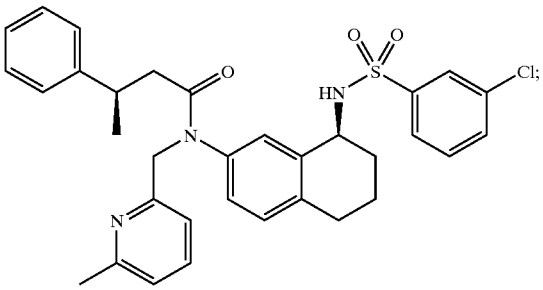
(56)
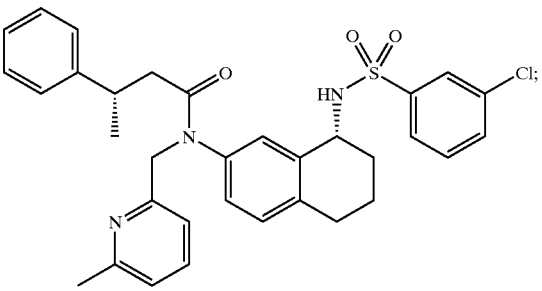
(57)
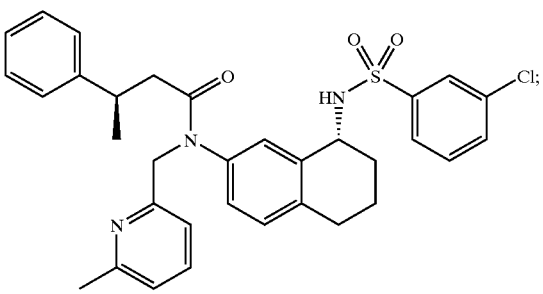
(58)
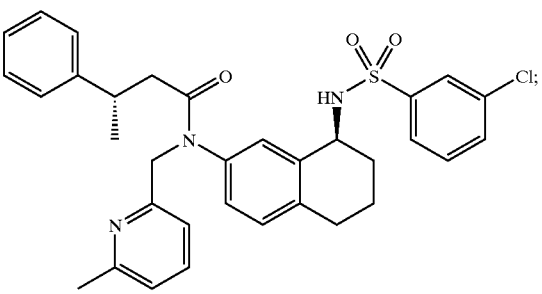
(59)
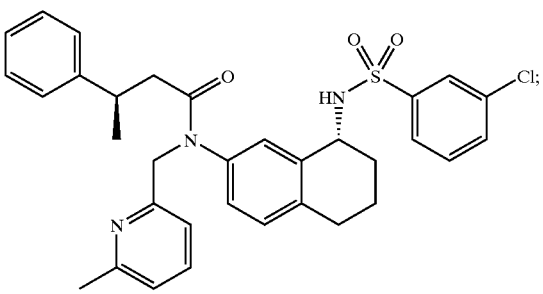
(60)
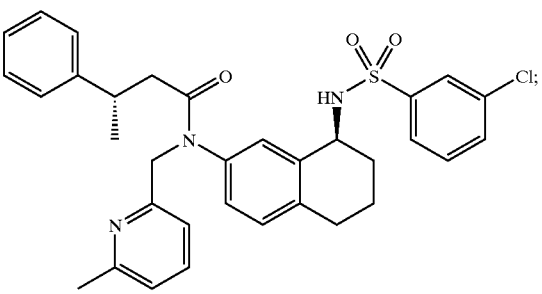

TABLE 1-continued
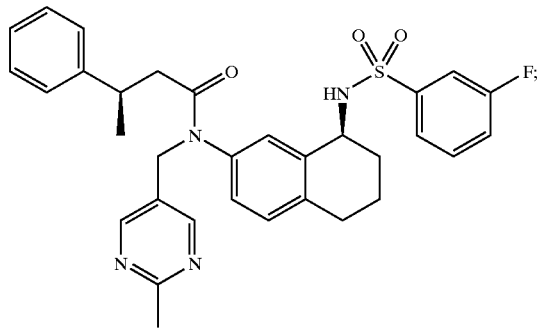
(61)
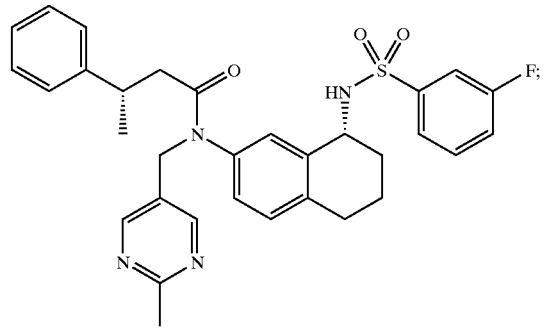
(62)
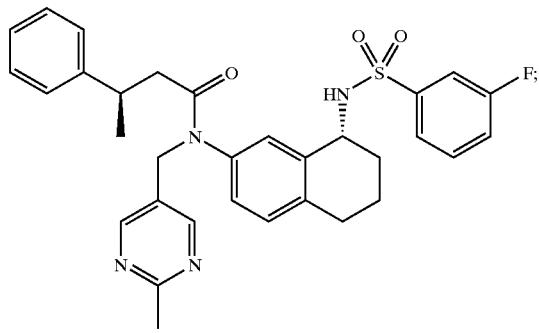
(63)
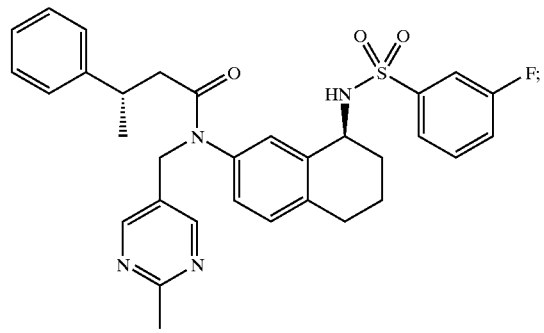
(64)
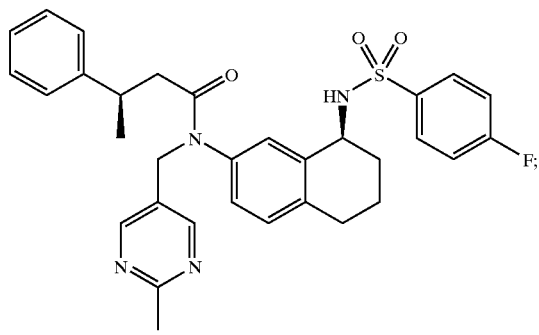
(65)
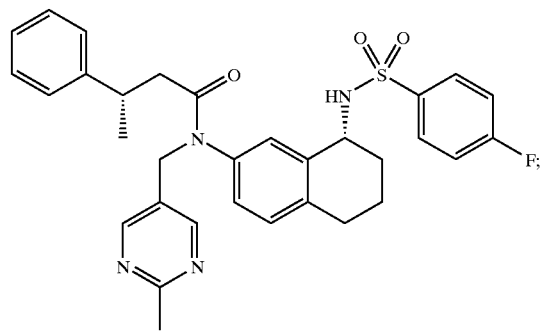
(66)
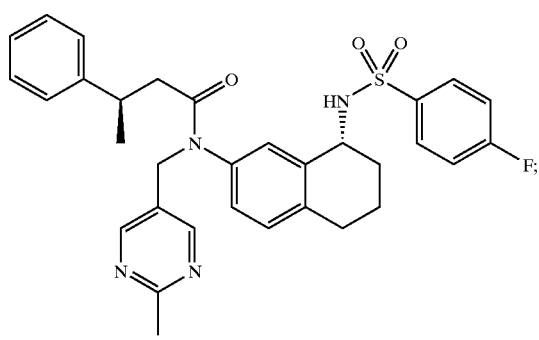
(67)
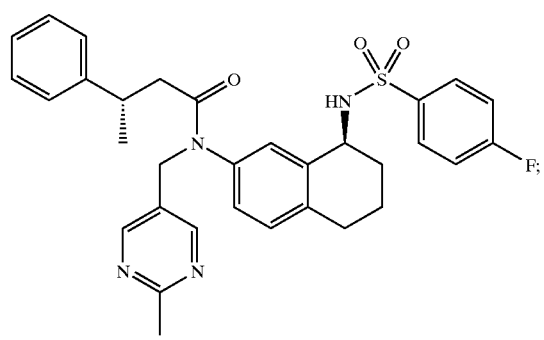
(68)

TABLE 1-continued
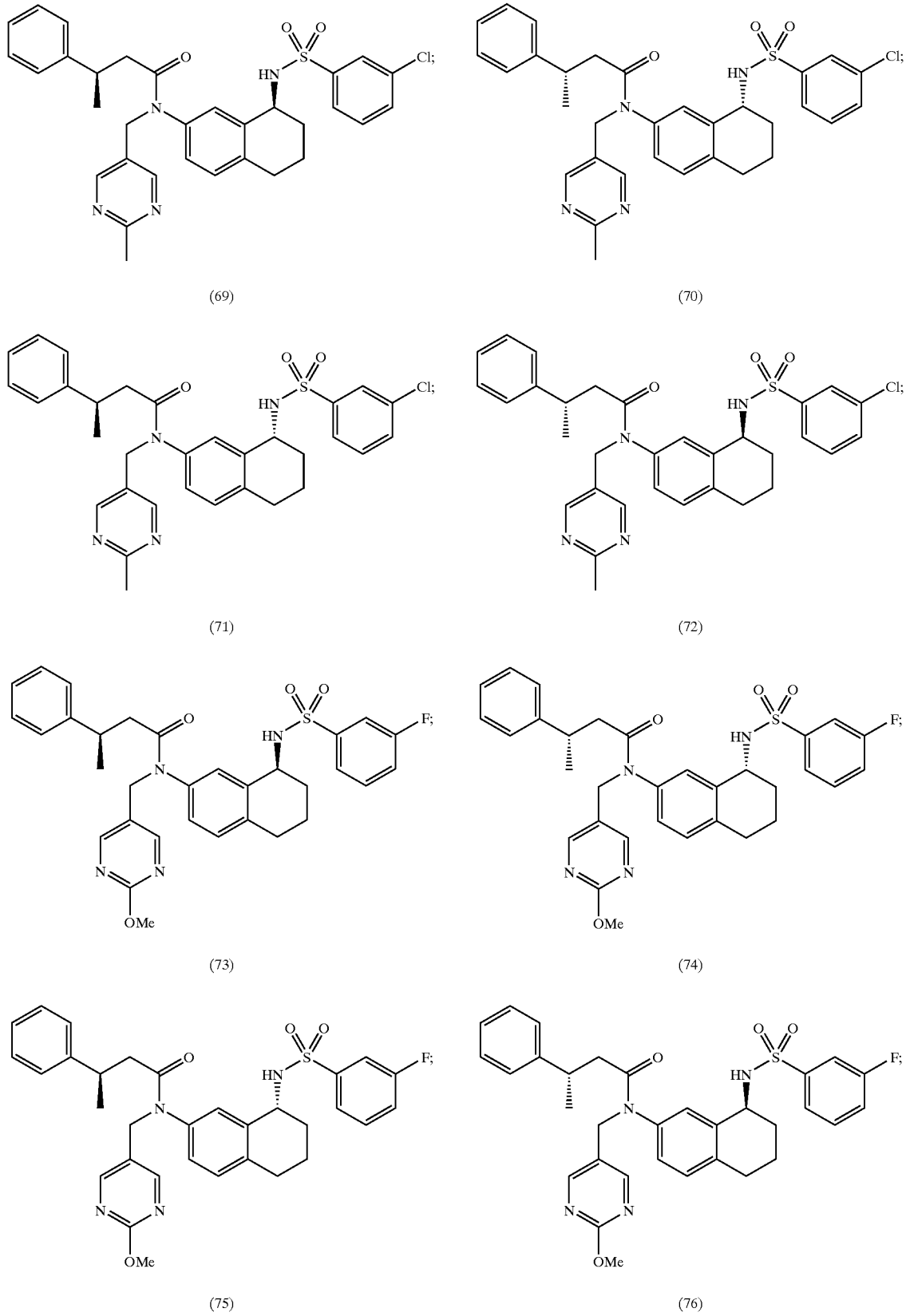

TABLE 1-continued
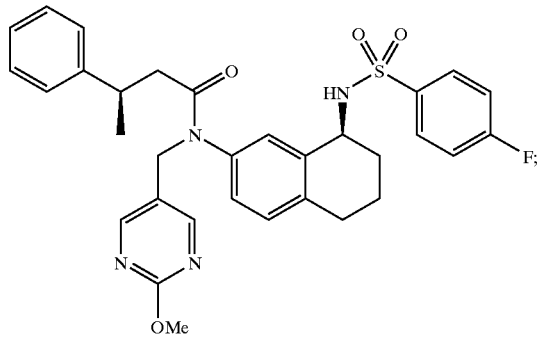
(77)
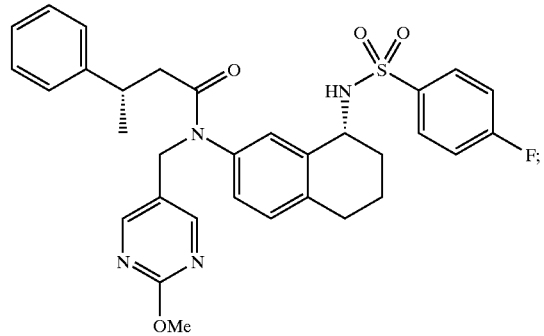
(78)
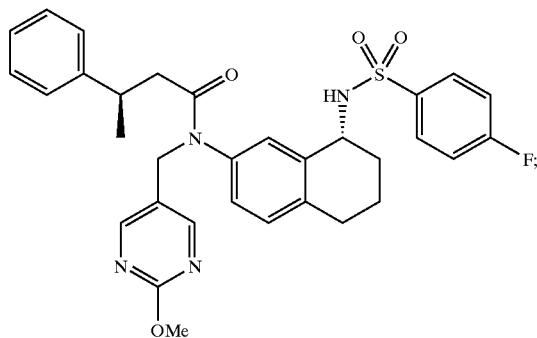
(79)
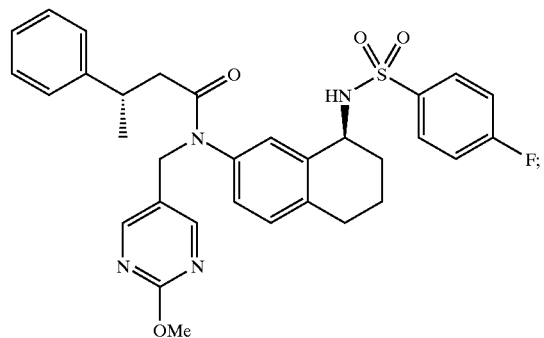
(80)
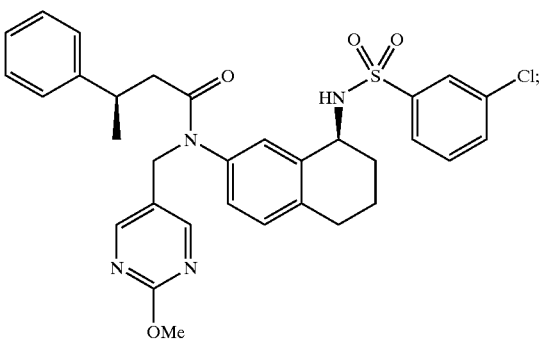
(81)
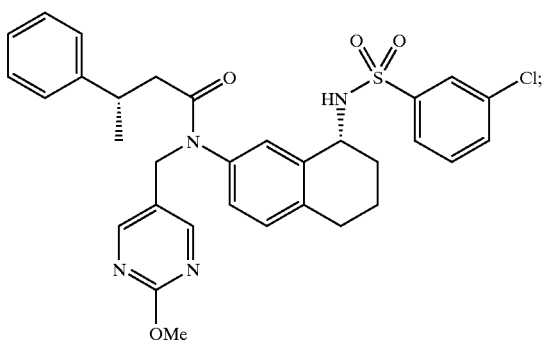
(82)
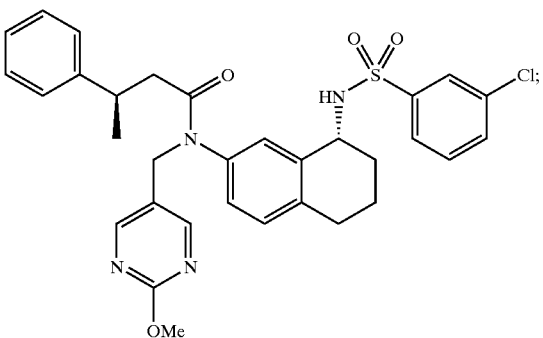
(83)
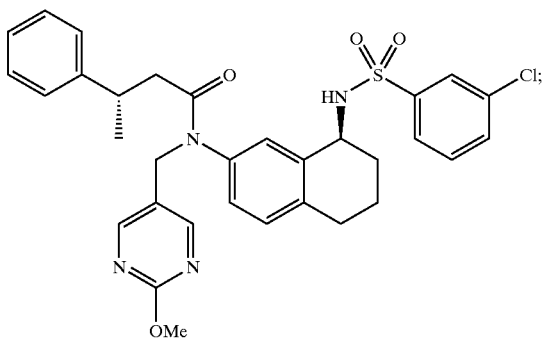
(84)

TABLE 1-continued
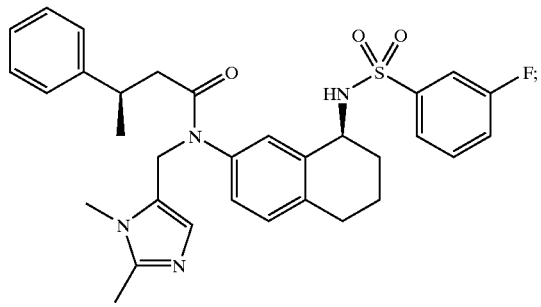
(85)
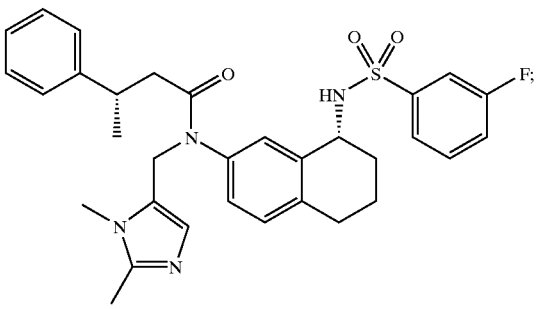
(86)
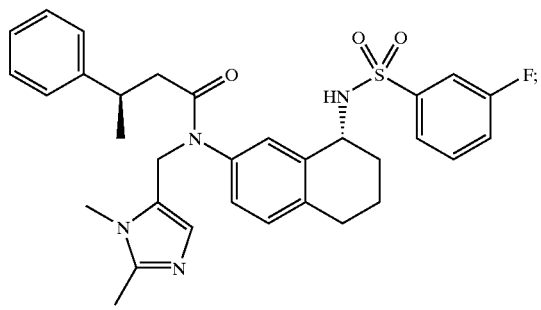
(87)
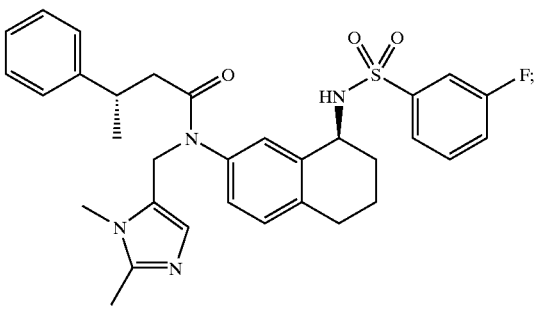
(88)
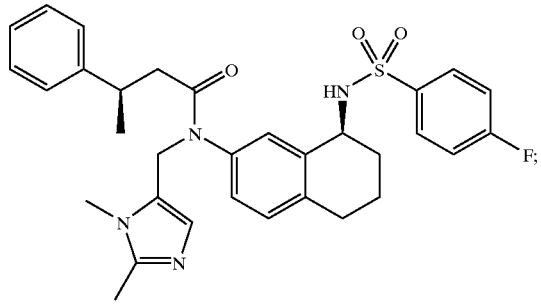
(89)
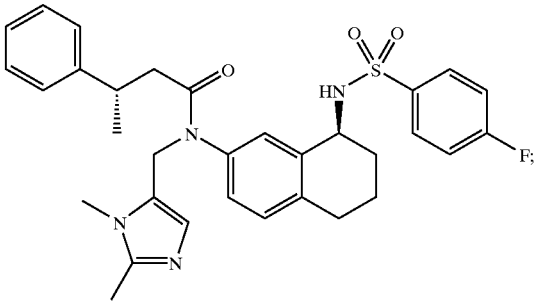
(90)
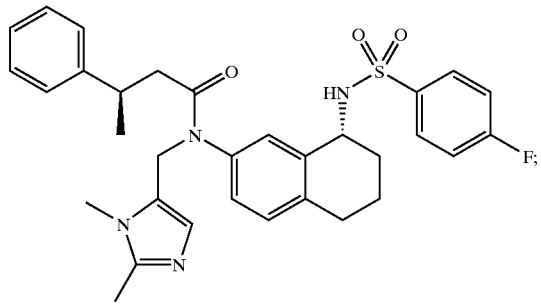
(91)
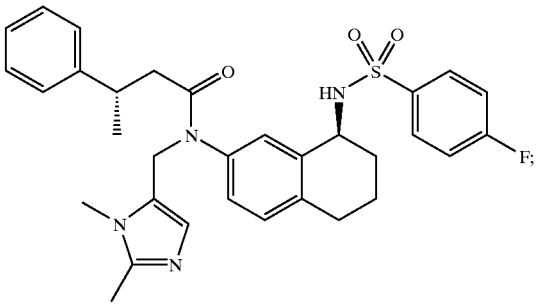
(92)

TABLE 1-continued
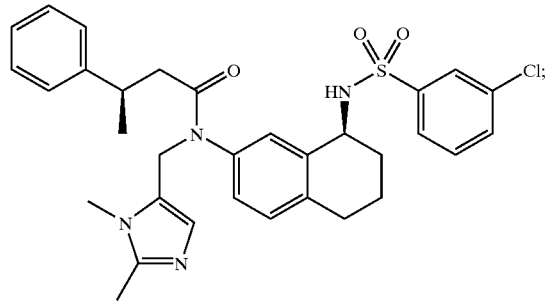
(93)
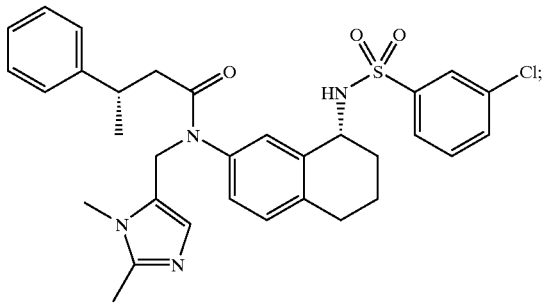
(94)
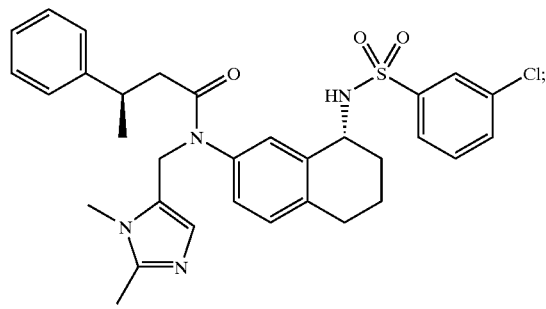
(95)
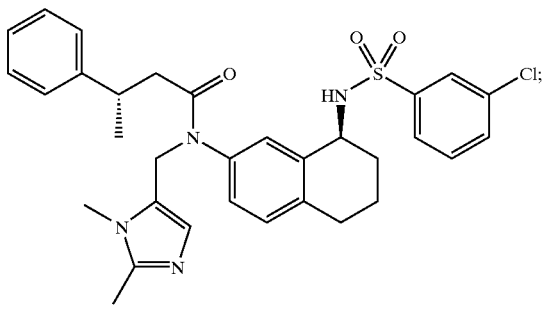
(96)
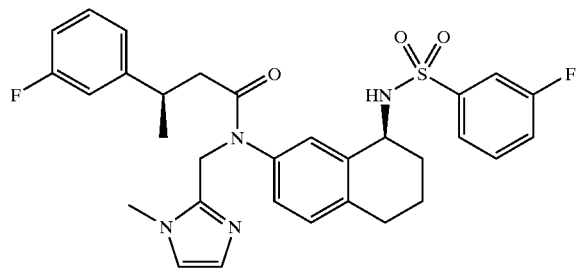
(97)
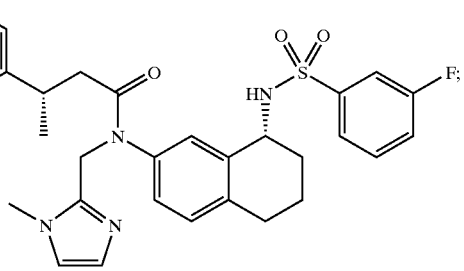
(98)
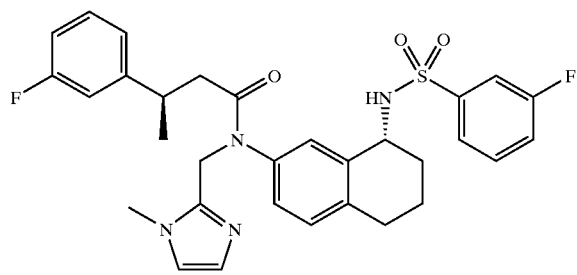
(99)
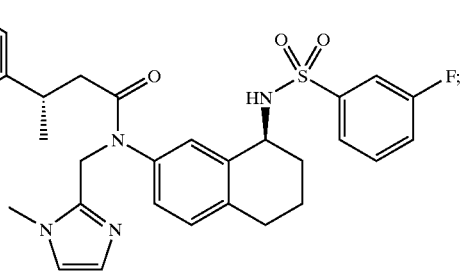
(100)
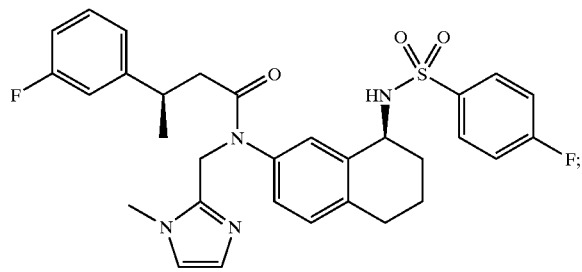
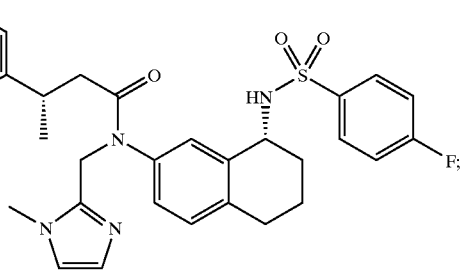

TABLE 1-continued
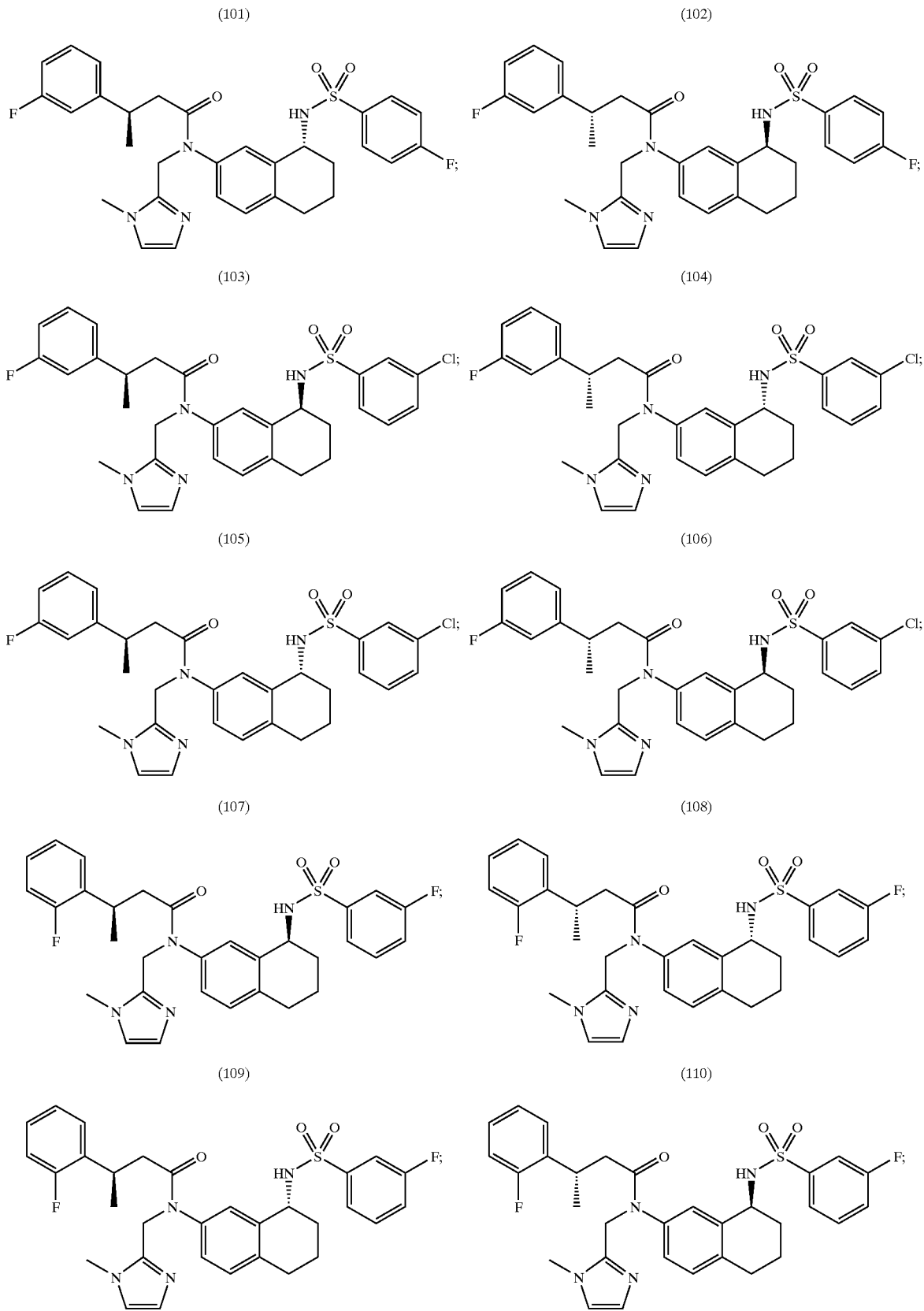

TABLE 1-continued
(111)
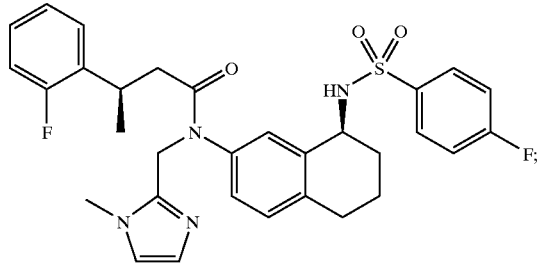
(112)
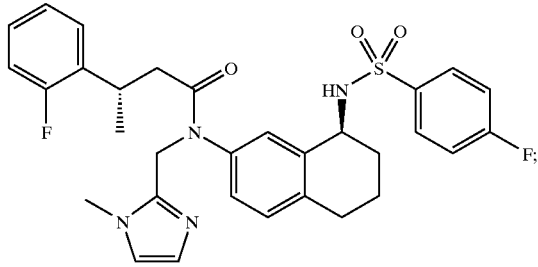
(113)
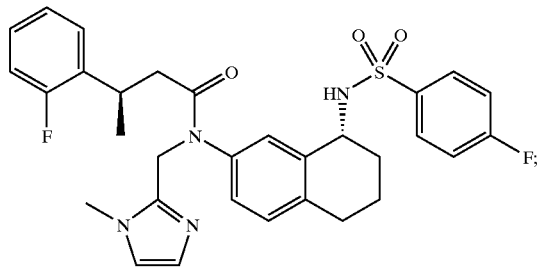
(114)
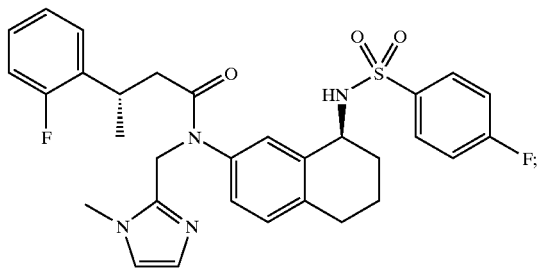
(115)
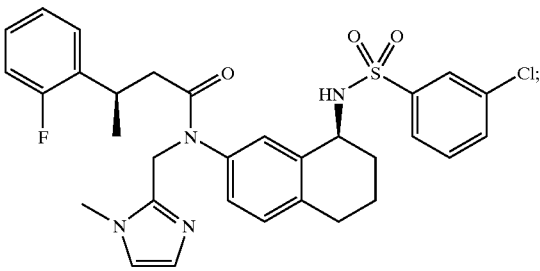
(116)
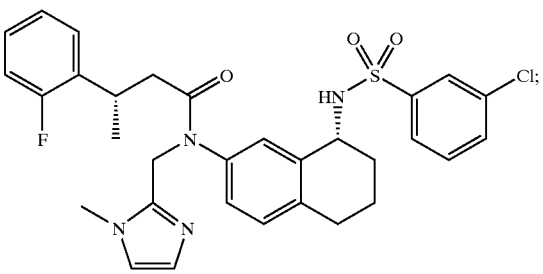
(117)
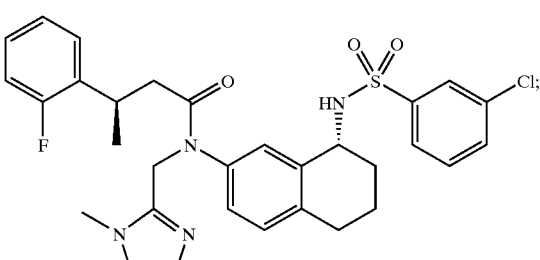
(118)
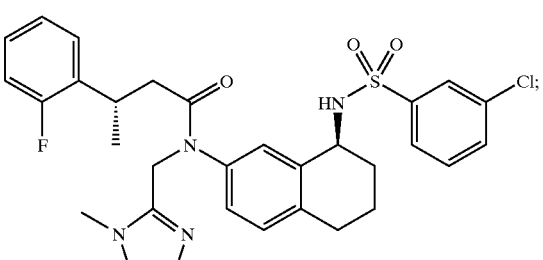
(119)
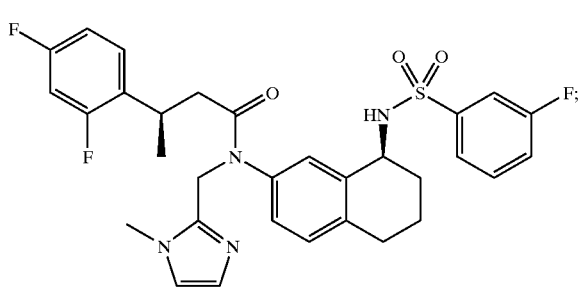
(120)
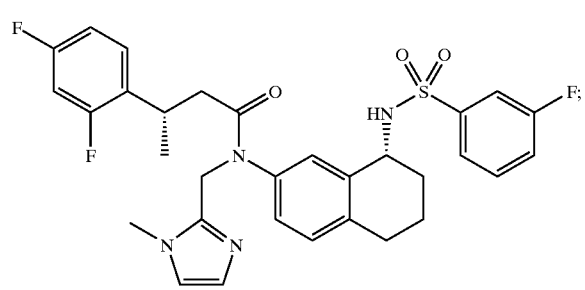

TABLE 1-continued
(121)
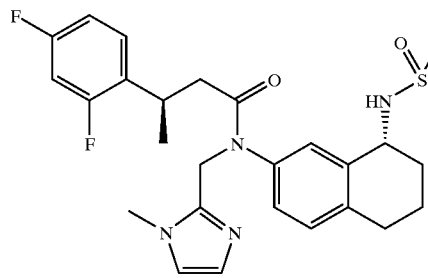
(122)
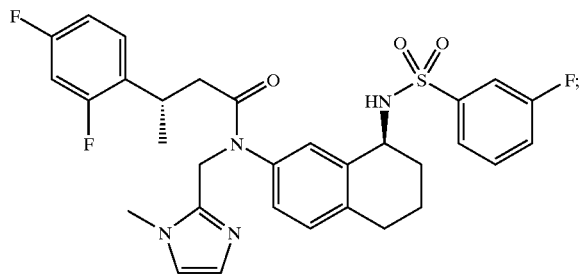
(123)
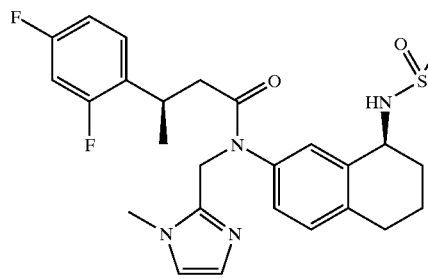
(124)
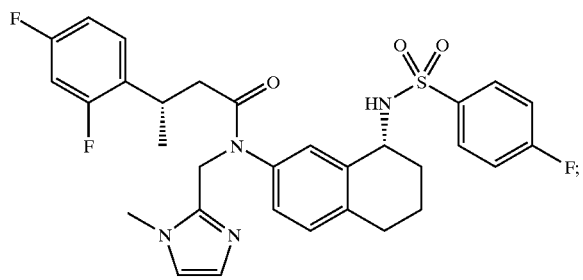
(125)
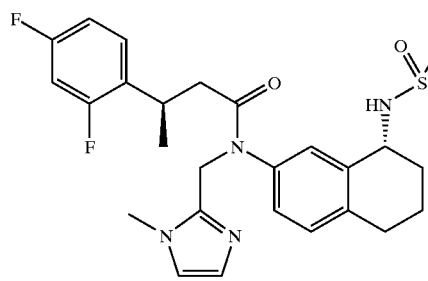
(126)
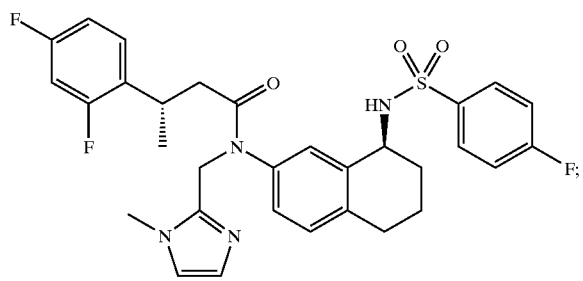
(127)
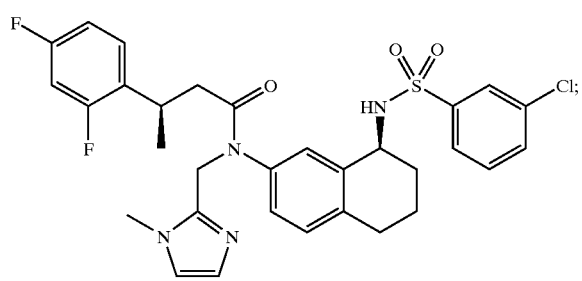
(128)
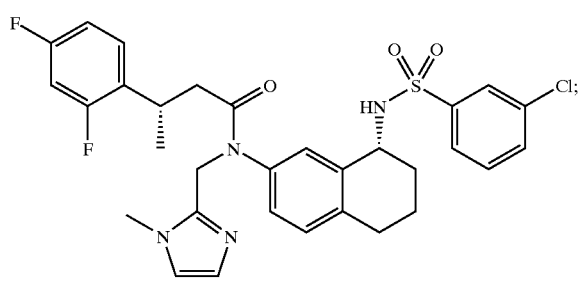
(129)
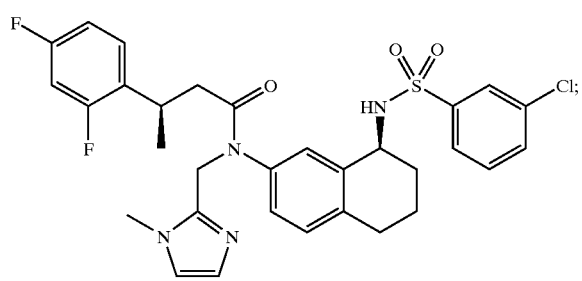
(130)
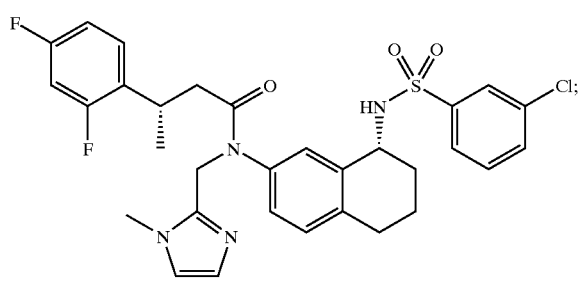

TABLE 1-continued
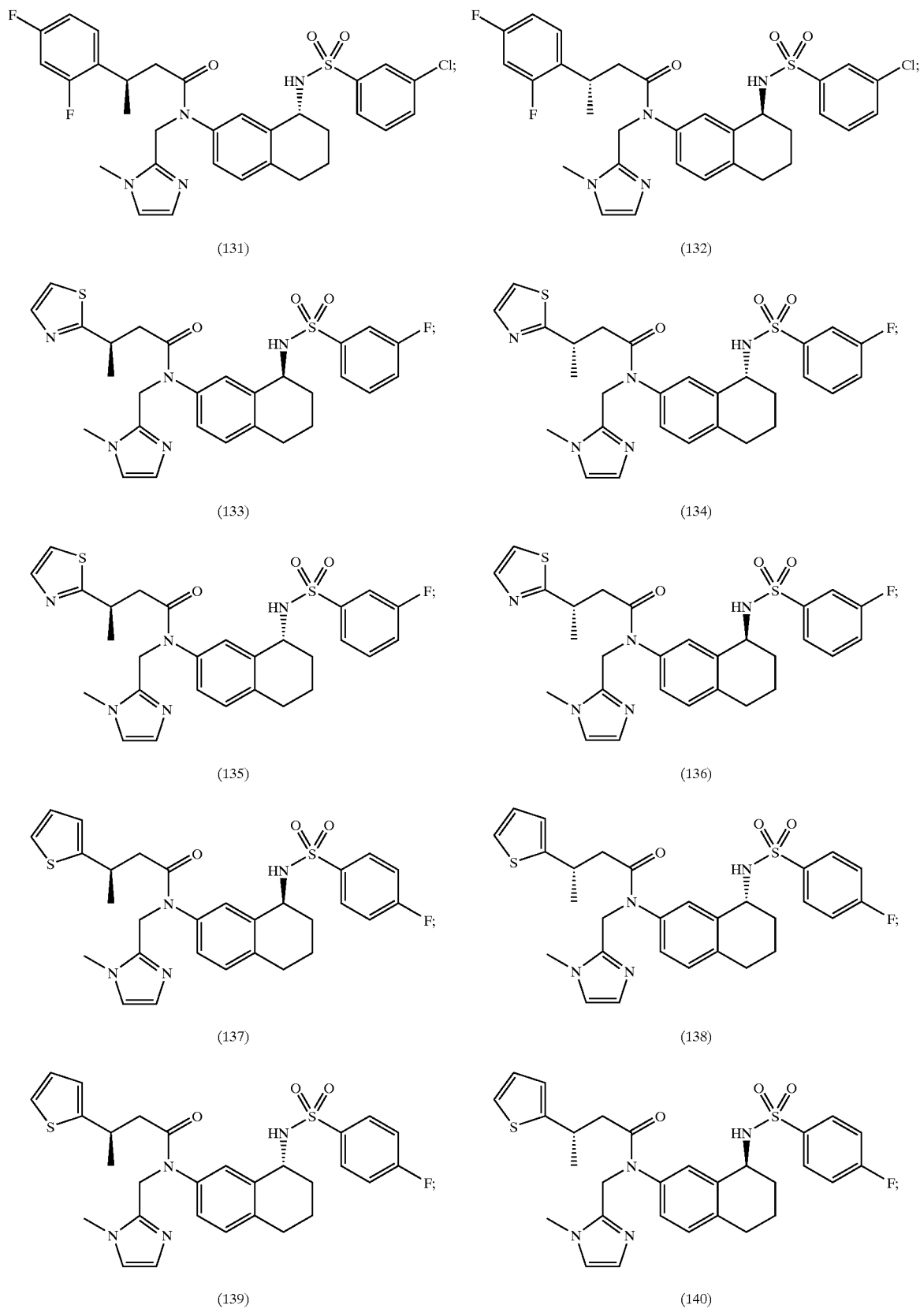

TABLE 1-continued
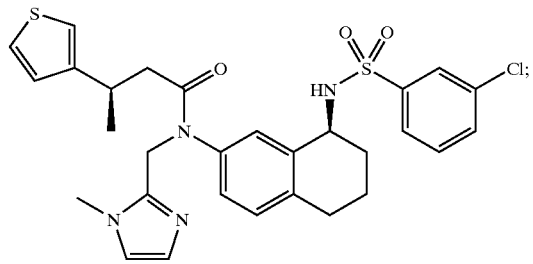
(141)
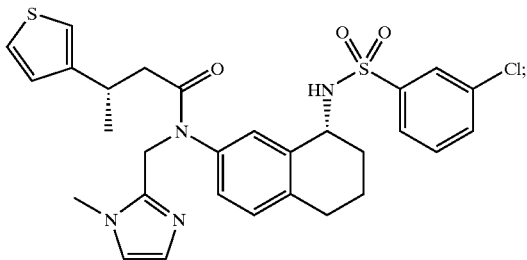
(142)
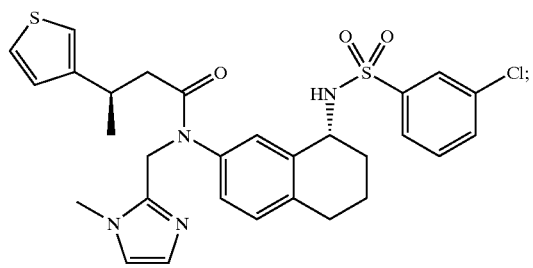
(143)
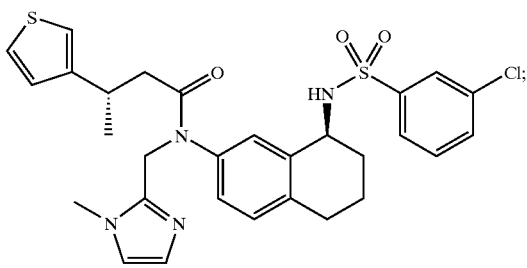
(144)
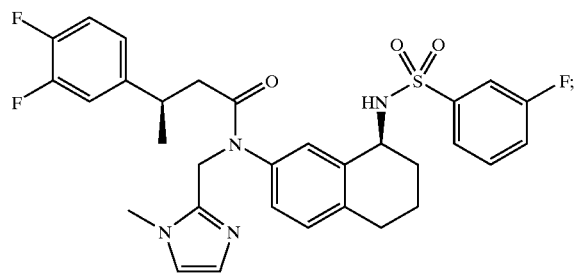
(145)
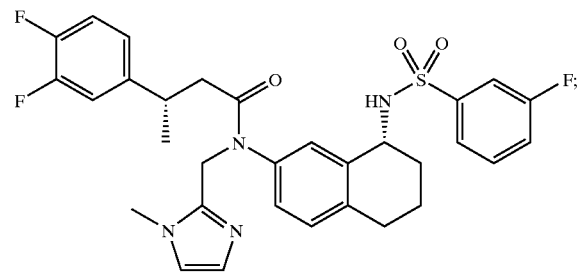
(146)
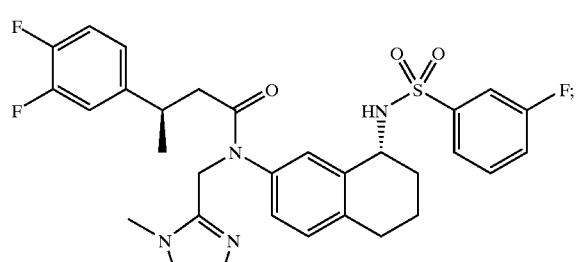
(147)
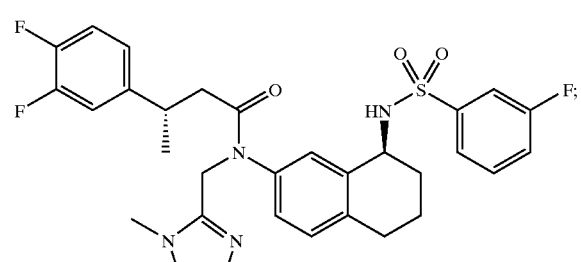
(148)
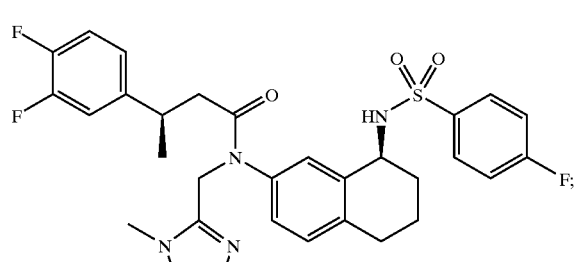
(149)
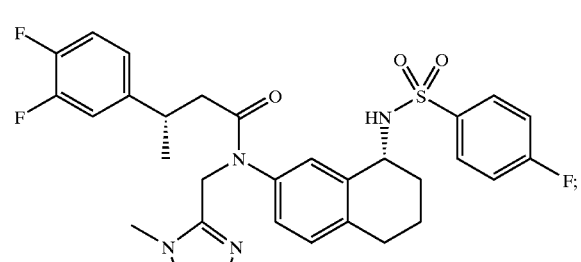
(150)

TABLE 1-continued
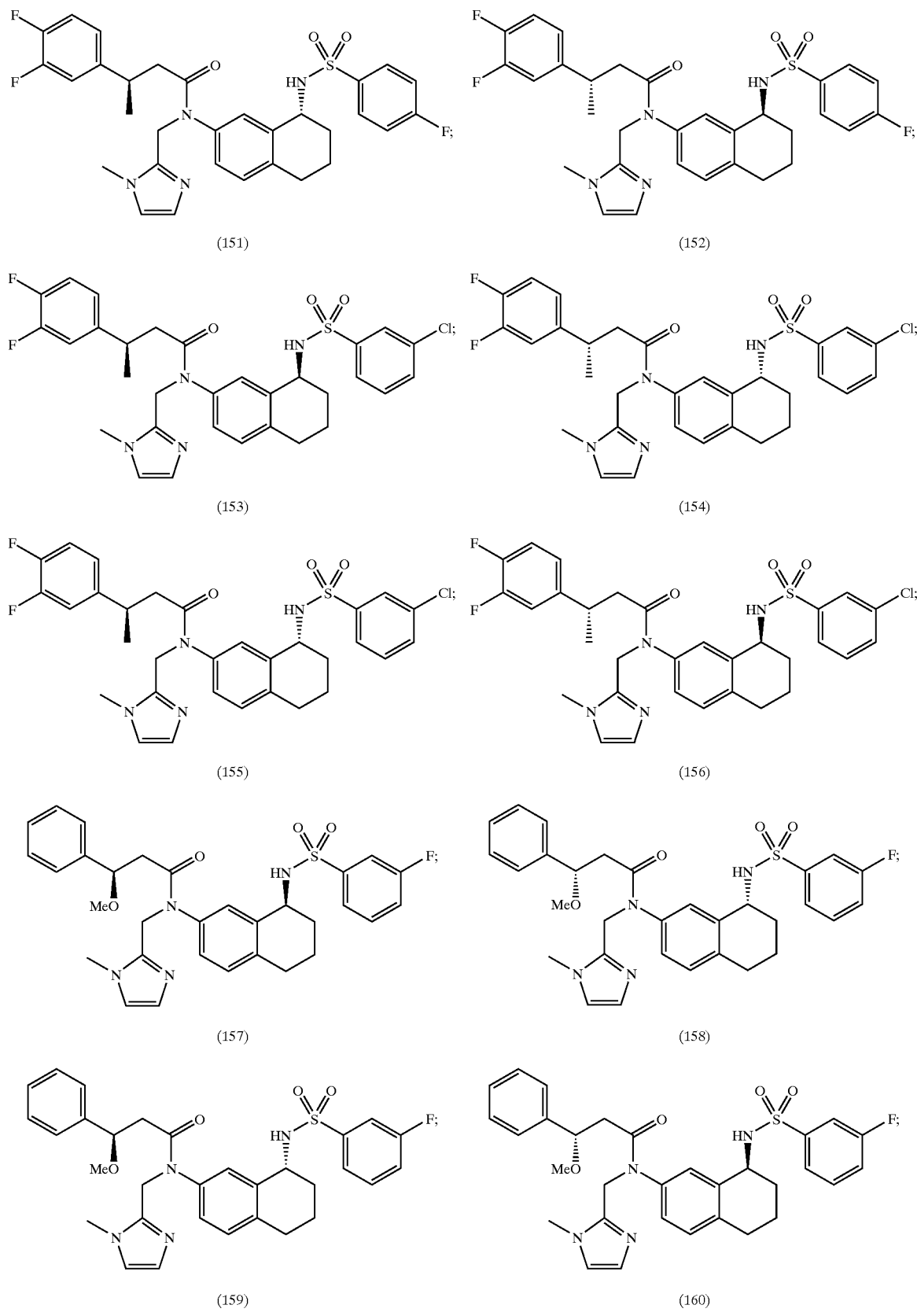

TABLE 1-continued
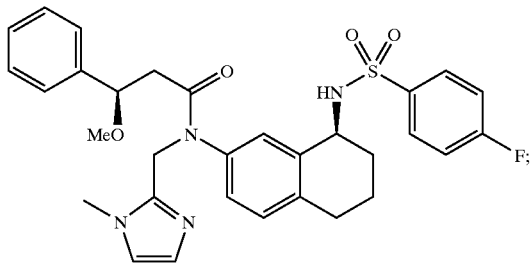
(161)
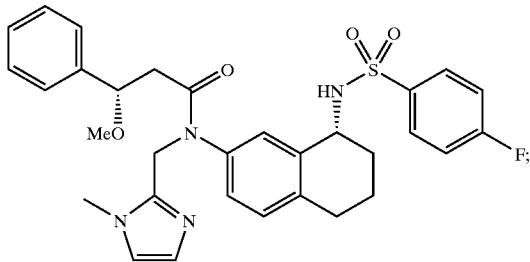
(162)
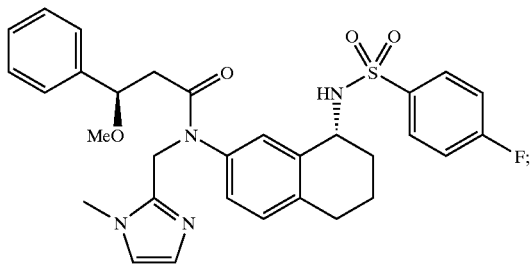
(163)
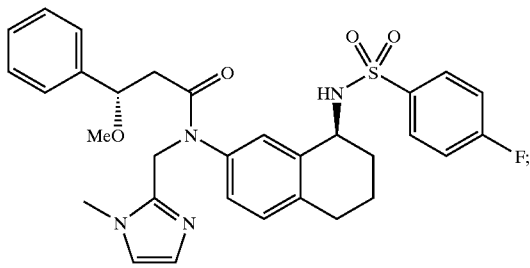
(164)
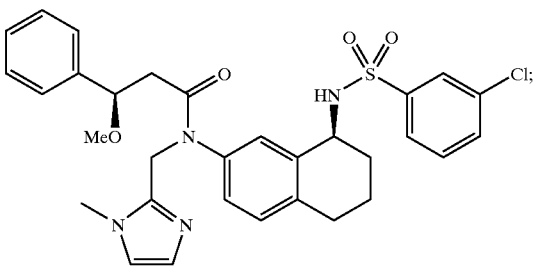
(165)
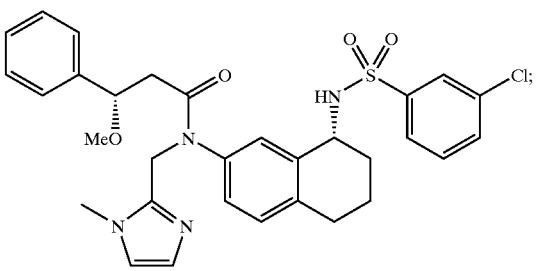
(166)
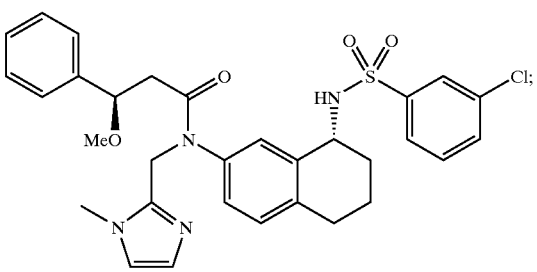
(167)
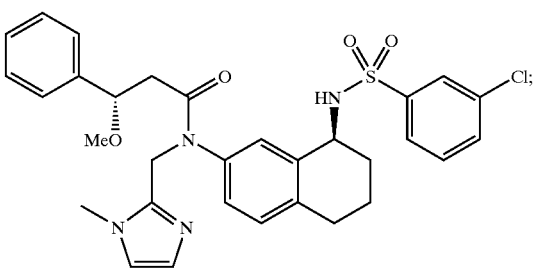
(168)
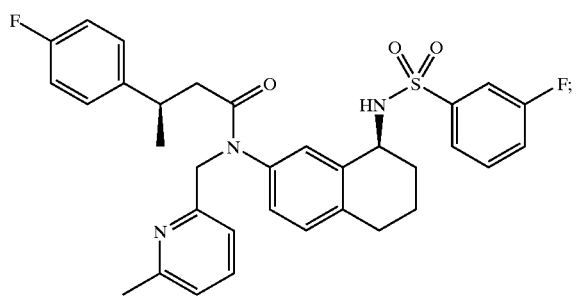
(169)
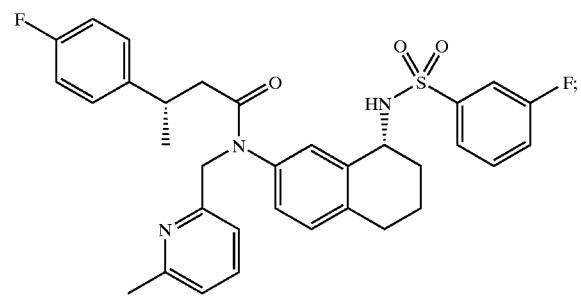
(170)

TABLE 1-continued
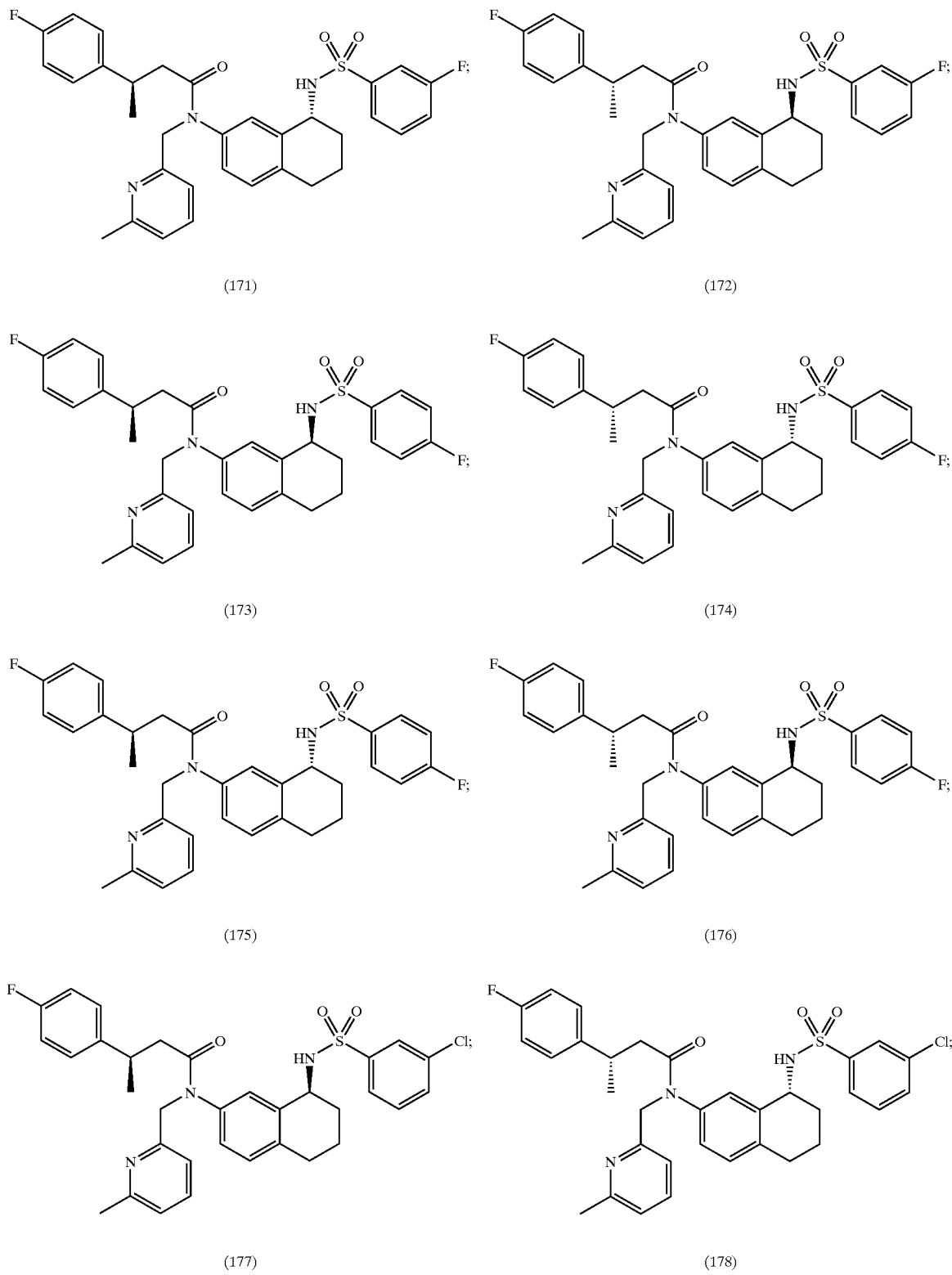

TABLE 1-continued
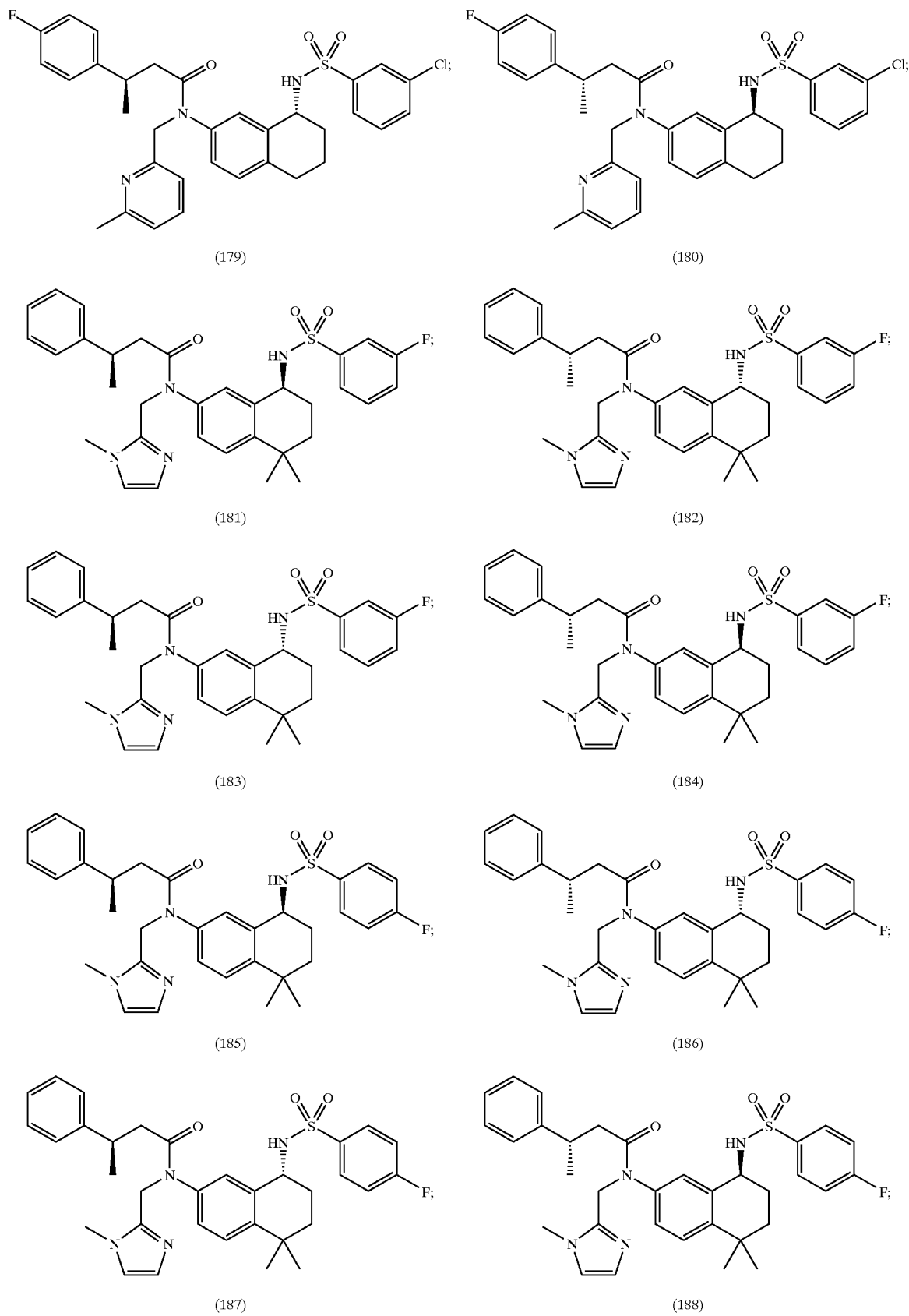

TABLE 1-continued
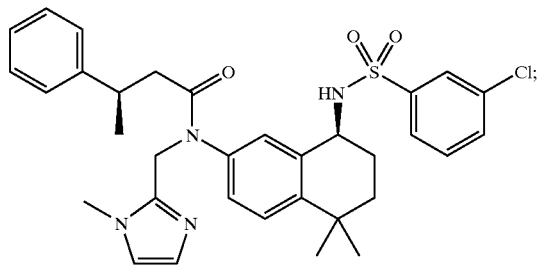
(189)
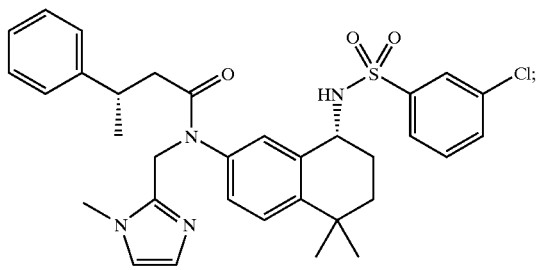
(190)
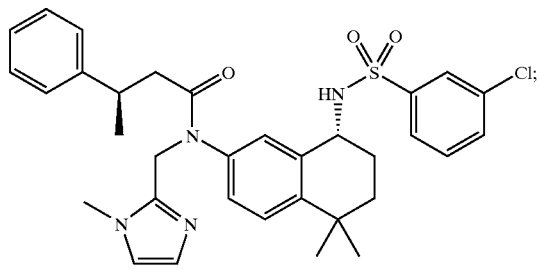
(191)
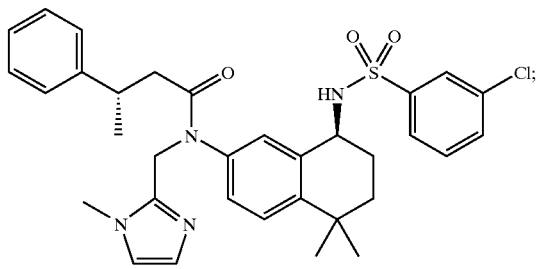
(192)
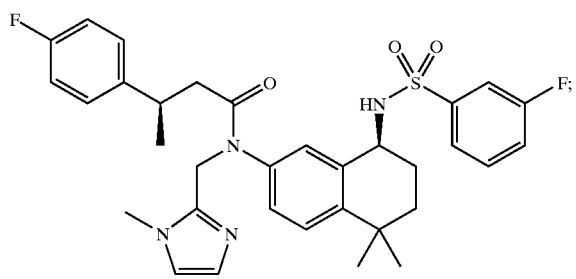
(193)
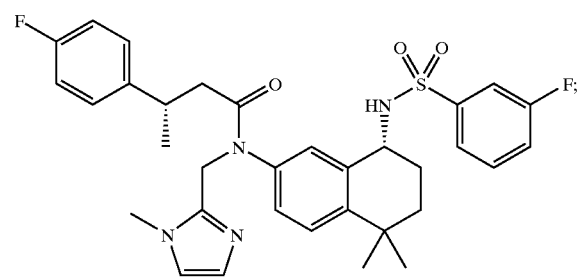
(194)
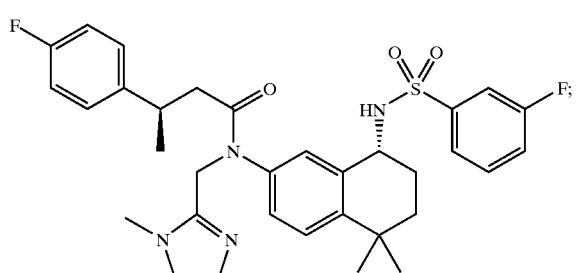
(195)
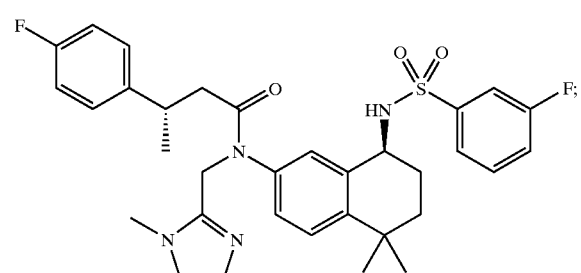
(196)
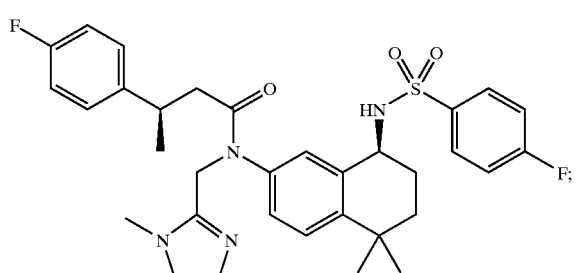
(197)
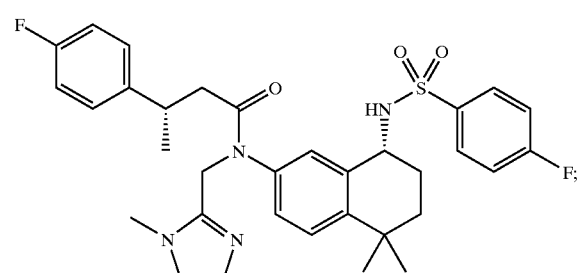
(198)

TABLE 1-continued
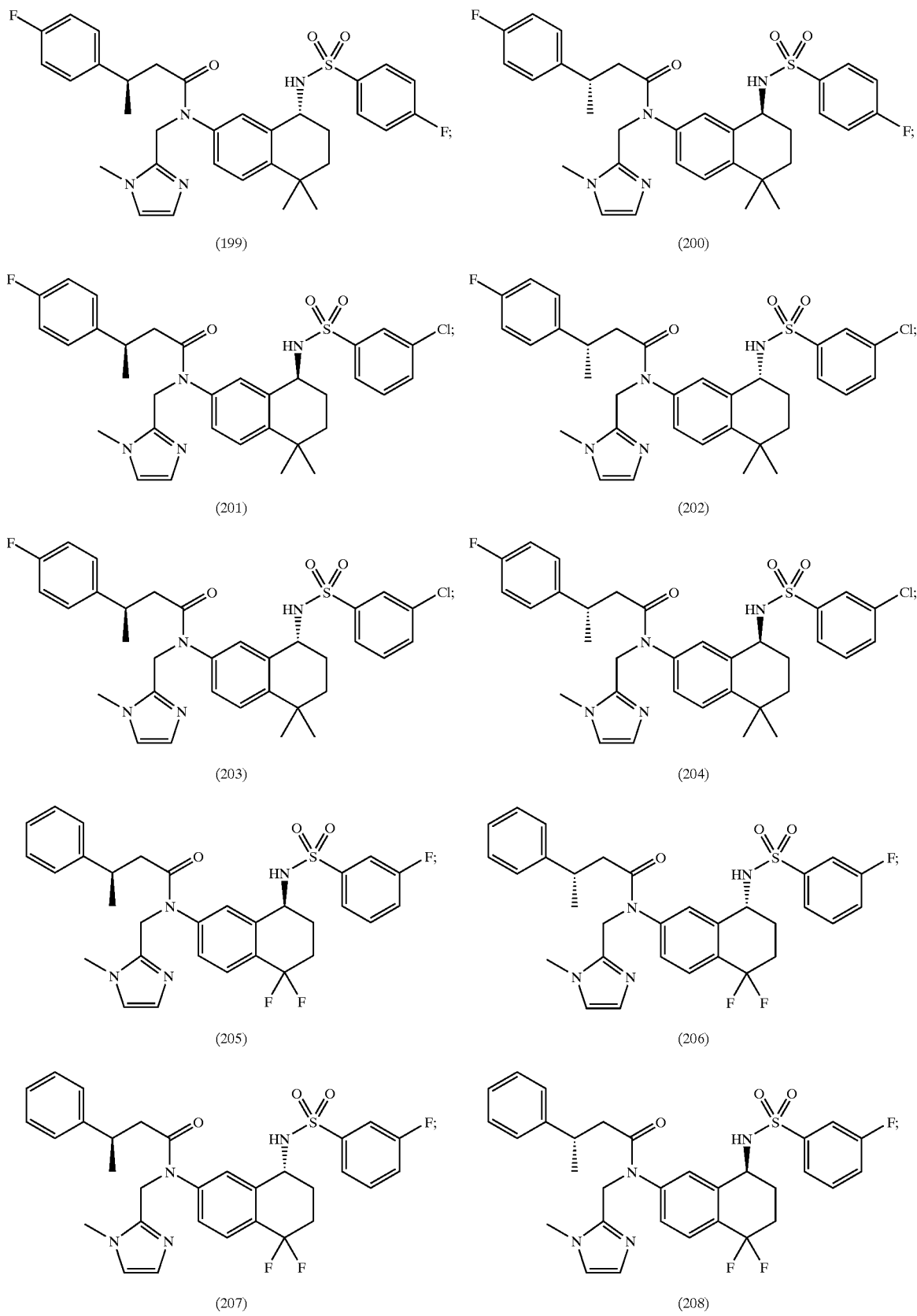

TABLE 1-continued
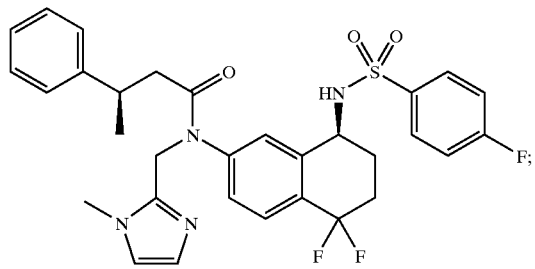
(209)
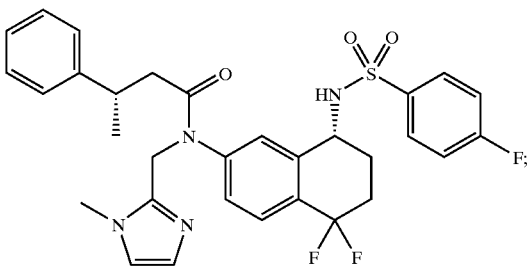
(210)
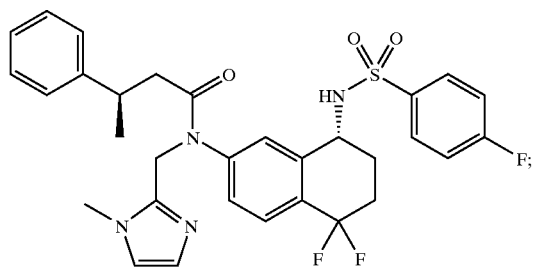
(211)
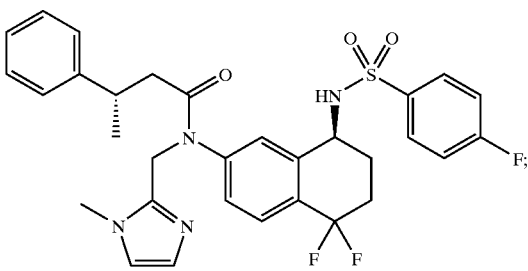
(212)
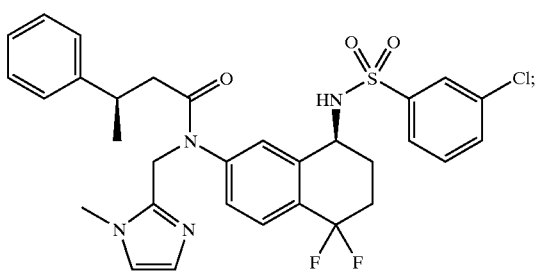
(213)
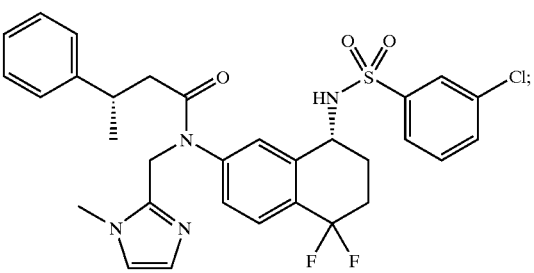
(214)
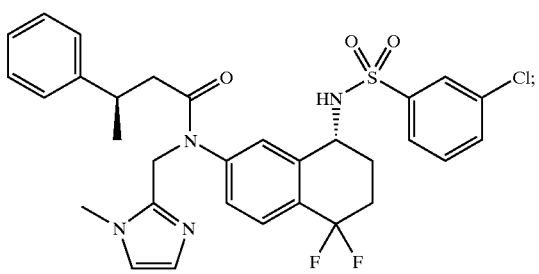
(215)
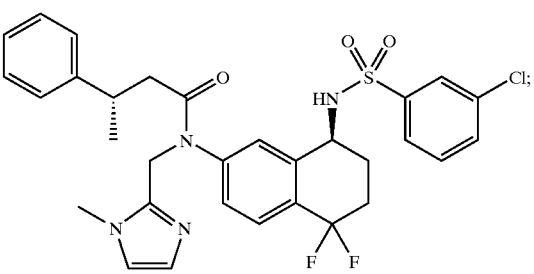
(216)
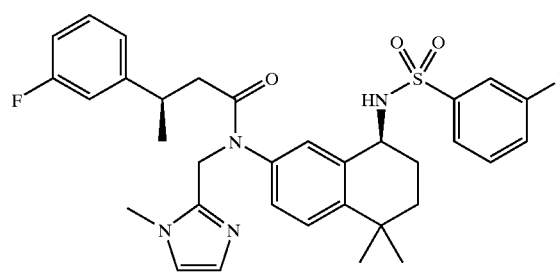
(217)
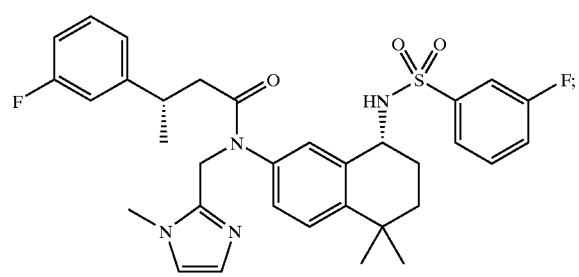
(218)

TABLE 1-continued
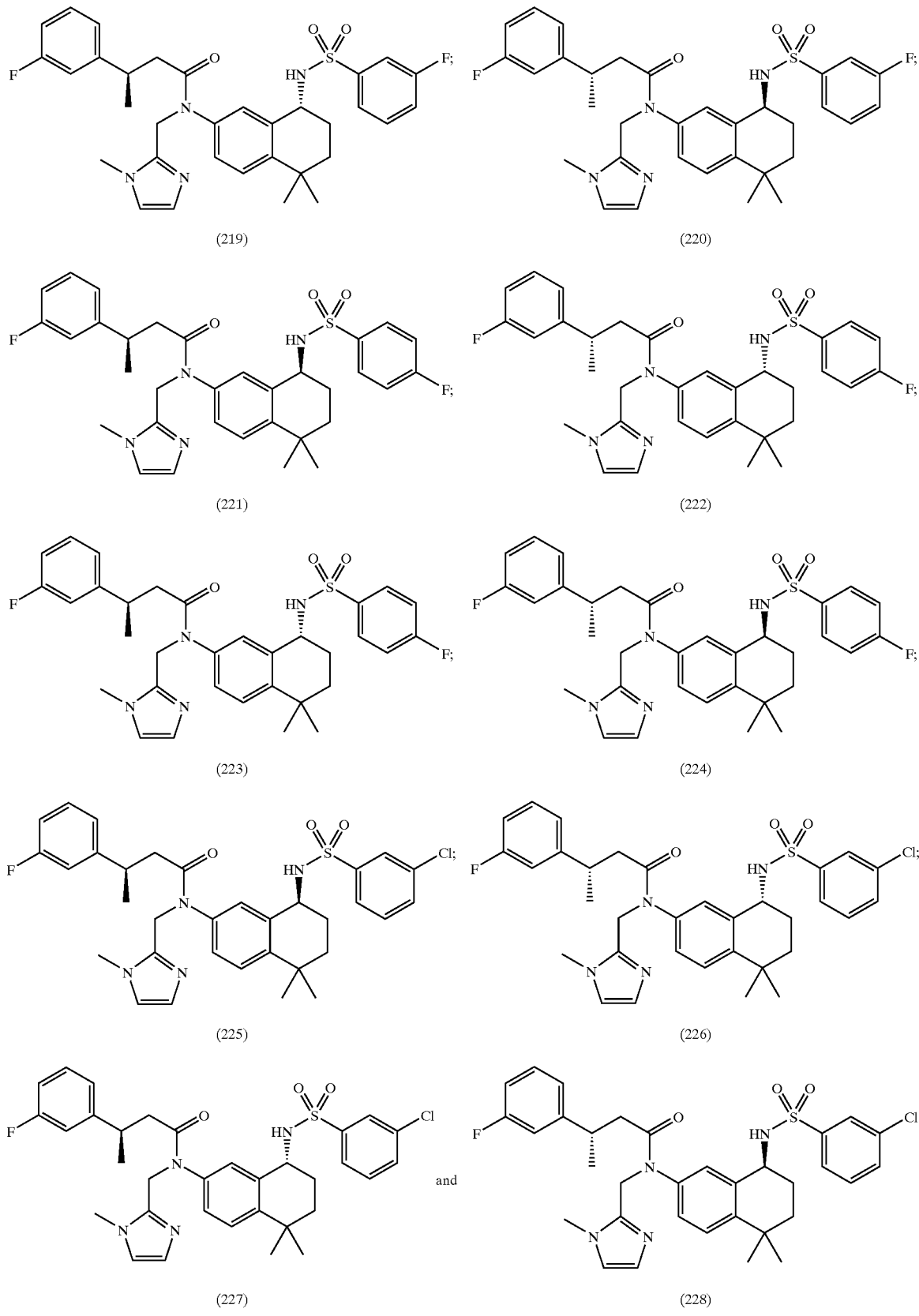

TABLE 1-continued
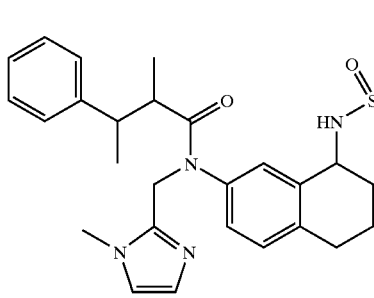
(229)
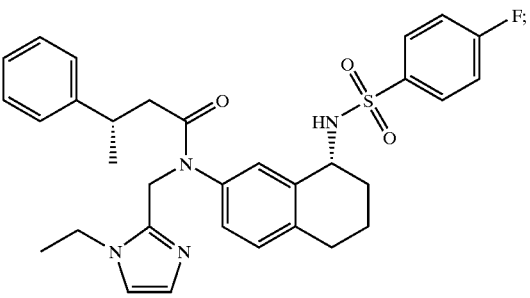
(230)
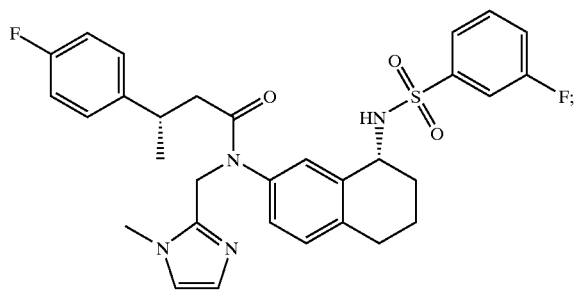
(231)
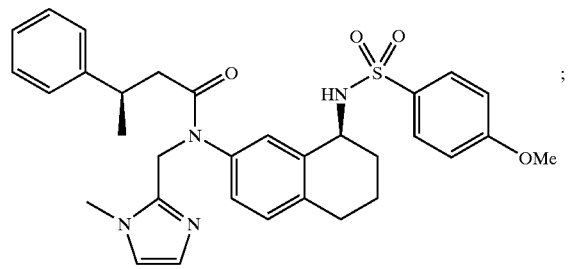
(232)
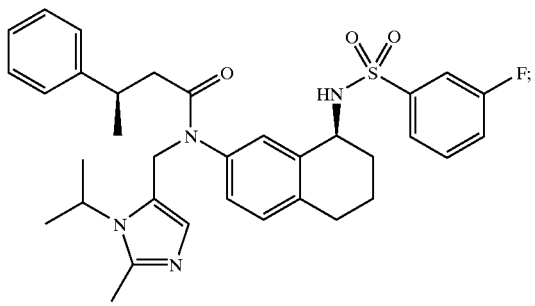
(233)
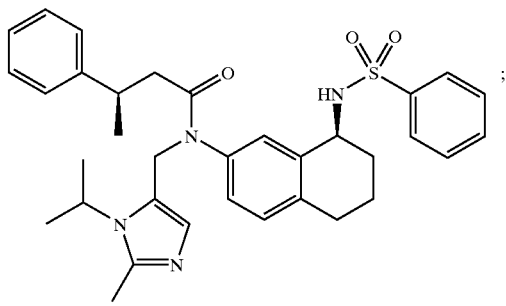
(234)
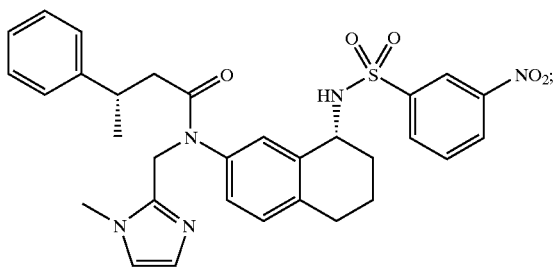
(235)
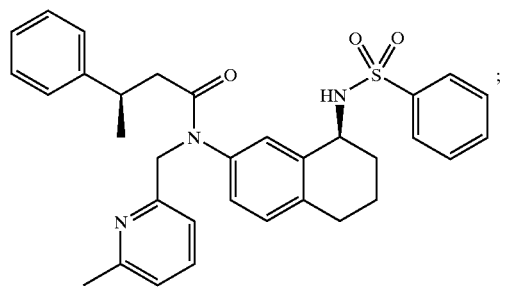
(236)

TABLE 1-continued

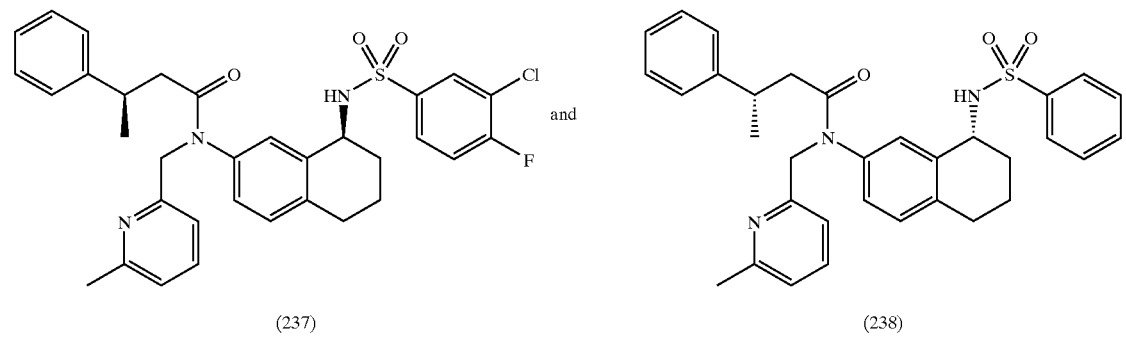

(237) and (238)

Those skilled in the art will appreciate that compounds embraced by the previous general formulae of the present invention and including the specific structures illustrated above, can be made using a variety of processes. Several processes suitable for making such compounds are set out below. In one process the compounds of following formula (with $R^5$ being either hydrogen or alkyl) may be prepared starting from intermediate 7 (see below). In another process, the compounds of the following formula may be prepared starting from intermediate 15 (see below). Those skilled in the art will appreciate that the techniques illustrated for the preparation of compounds of the following formulae may also be used for the preparation of other compounds falling within the scope of the present invention:

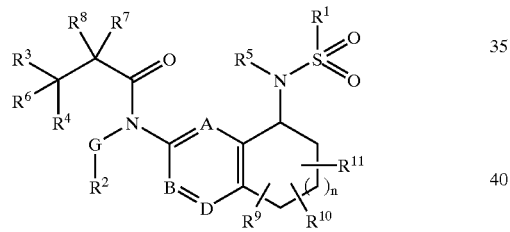

It will be recognized by those skilled in the art that there are at least two and often more than two chiral centers in the compounds falling within the scope of the present invention and thus such compounds will exist as various stereroisomeric forms. Applicants intend to include all of the various stereoisomers within the scope of the invention.

Substitutent groups are chosen in such a fashion so as to produce stable compounds as will be understood by those skilled in the art.

Compounds of previous formula can be prepared by using the sequence of steps outlined in General Schemes 1 to 7 set out below.

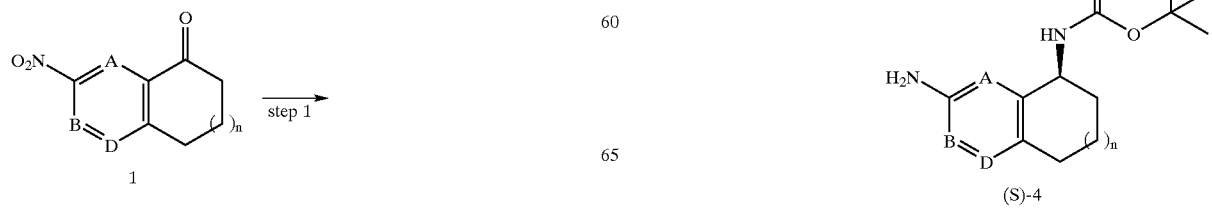

Referring to General Scheme 1, chiral intermediates (R)-4 and (S)-4 may be prepared starting from the keto compound 1 which in step 1 is made to undergo a reductive amination by reacting compound 1 with ammonium acetate in the presence of a reducing agent such as sodium cyanoborohydride in an organic solvent such as methanol preferably at an elevated temperature to form the amino compound 2.

The amino functionality of compound 2 is then protected in step 2 with a suitable nitrogen protecting group such as the tert-butyl (Boc) carbamate group to give compound 3. One skilled in the art will recognize that there are other possible amino protecting groups as discussed in "Protective Groups in Organic Synthesis", T. W. Green and P. G. M. Wuts (1999).

The nitro group of compound 3 may be reduced in step 3 using a suitable reducing agent such as tin (II) chloride dihydrate in an organic solvent such as ethanol preferably at an elevated temperature to form the aniline compound 4. Alternatively, compound 3 may be treated in step 3 with a reducing agent such as sodium borohydride in the presence of a catalytic amount of nickel chloride preferably at 0° C. in an organic solvent such as methanol or tetrahydrofuran to form the aniline compound 4.

Compound 4 may be subjected to chiral chromatographic resolution in step 4 using HPLC methods on a preparative scale to provide the individual enanatiomer compound (R)-4 and the individual compound (S)-4. Suitable preparative chromatography conditions for the chiral chromatographic resolution of compounds of formula 4 where A, B, and D are CH include the use of a Chiralpak AD column (Daicel Chemical Industries, LTD.) using a solvent mixture such as hexane/isopropyl alcohol/diethylamine as the eluent.

General Scheme 2

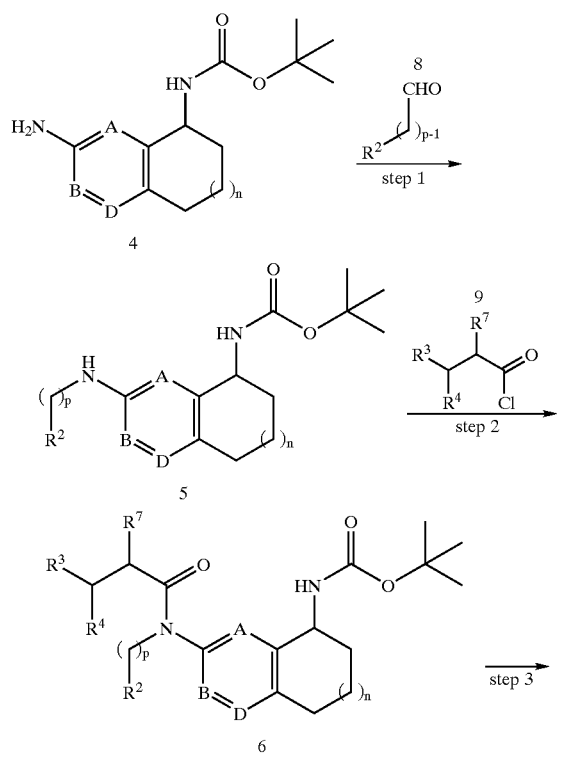

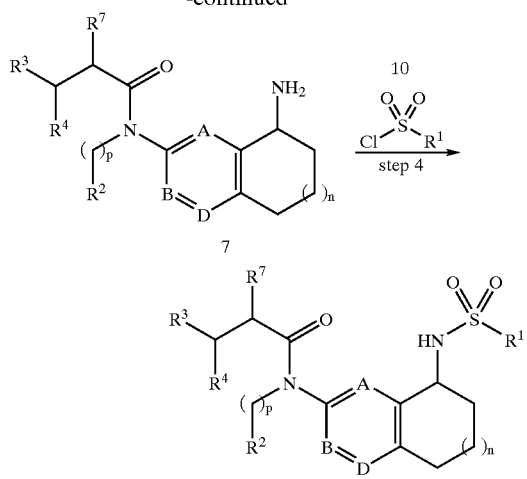

Referring to General Scheme 2, compounds of the previous general formula may be prepared starting with the aniline compound 4 which is made to undergo a reductive alkylation in step 1 by reacting compound 4 with an aldehyde of formula 8 preferably at elevated temperature to form an imine intermediate (not shown) which is subsequently reduced using sodium borohydride to form the substituted aniline compound 5. This two-step reaction sequence is preferably carried out in an organic solvent such as methanol. One skilled in the art will appreciate that subjecting either compound (R)-4 or compound (S)-4 to a similar reaction sequence as described above for compound 4 may provide compounds of the present invention in the form of a single stereoisomer.

Compound 5 is treated with an acid chloride of formula 9 in step 2 in the presence of a base such as triethylamine or pyridine in an organic solvent such as methylene chloride or tetrahydrofuran to form the amide compound 6. One skilled in the art will recognize that an acid chloride of formula 9 may be conveniently prepared starting from the corresponding carboxylic acid by methods well know in the literature.

Deprotection of compound 6 in step 3 is accomplished using standard techniques well know in the literature such as dilute HCl or trifluoroacetic acid to give the amino compound 7.

Compound 7 may be directly made to undergo a sulfonylation in step 4 by reacting compound 7 with a sulfonylating agent of general formula 10 in the presence of a base such as triethylamine or pyridine in an organic solvent such as methylene chloride or tetrahydrofuran to form sulfonylated compounds of the previously noted general formula.

General Scheme 1

Referring to General Scheme 3, compounds of the previous general formula where $R^5$ may be prepared starting from compound 7 which is which is made to undergo an alkylation in step 1 to form substituted compound 11. One skilled in the art will recognize that there are a variety of methods to alkylate an amino group known in the literature.

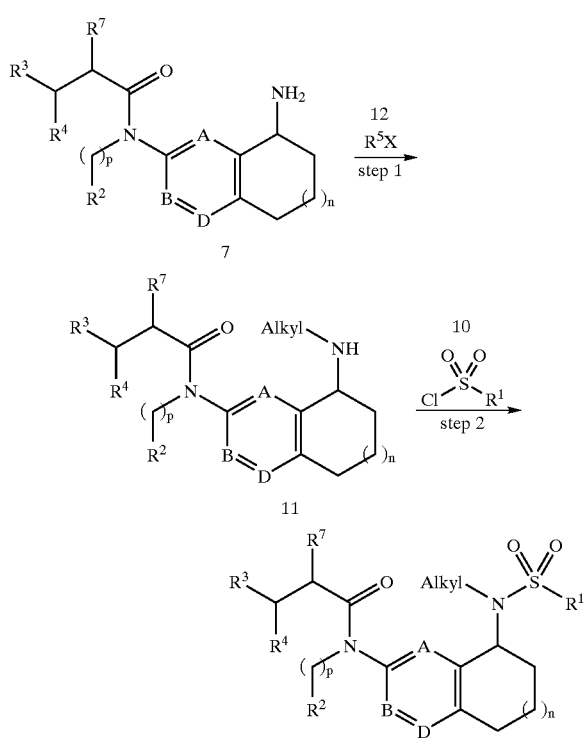

Compound 11 may be reacted with a sulfonylating agent of formula 10 in step 2 in the presence of a base such as triethylamine or pyridine in an organic solvent such as methylene chloride or tetrahydrofuran to form sulfonylated compounds where $R^5$ is alkyl.

General Scheme 4

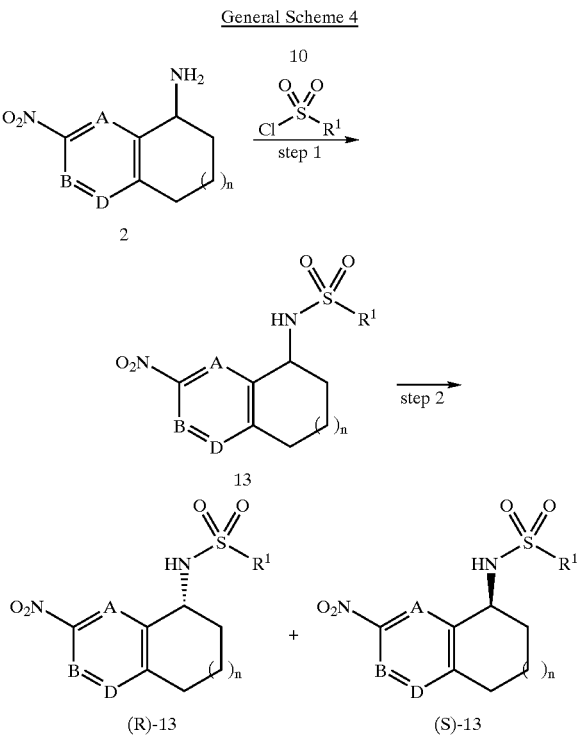

Referring to General Scheme 4, chiral intermediates (R)-13 and (S)-13 may be prepared starting from the amino compound 2 which in step 1 is made to undergo a sulfonylation by reacting compound 2 with a sulfonylating agent of formula 10 in an organic solvent such as methylene chloride or tetrahydrofuran to form the sulfonylated compound 13.

Compound 13 may be subjected to chiral chromatographic resolution in step 2 using HPLC methods on a preparative scale to provide the individual enantiomer compound (R)-13 and the individual enantiomer compound (S)-13. Suitable preparative chromatography conditions for the chiral chromatographic resolution of compounds of formula 13 where A, B, and D are CH and $R^1$ is aryl include the use of a Chiralpak AS column (Daicel Chemical Industries, LTD.) using a solvent such as methanol as the eluent.

General Scheme 5

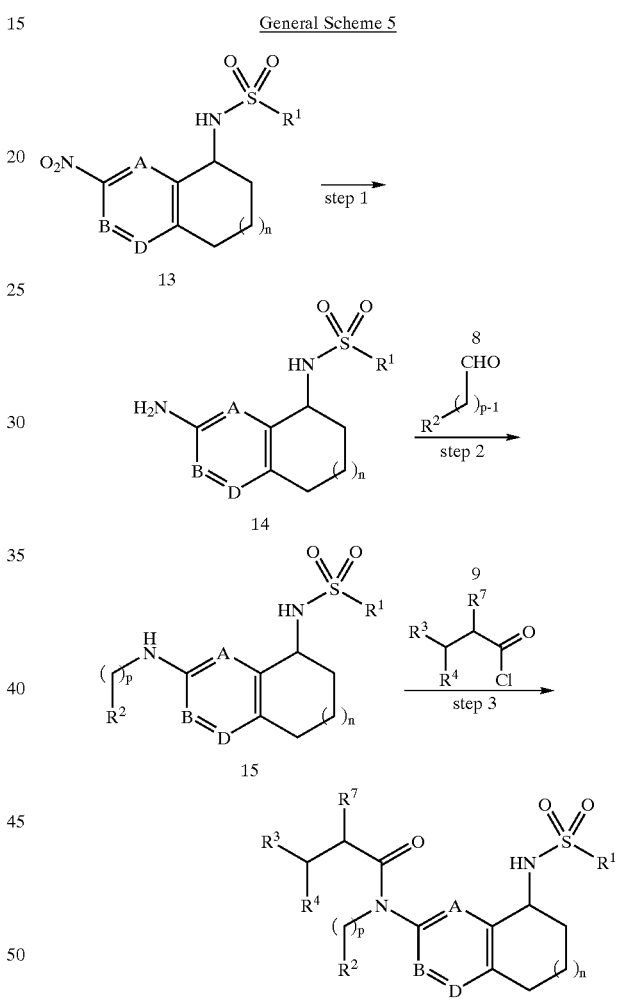

Referring to General Scheme 5, compounds of the previous general formula may be prepared starting from nitro compound 13 which in step 1 is reduced using a suitable reducing agent such as tin (II) chloride dihydrate in an organic solvent such as ethanol preferably at an elevated temperature to form the aniline compound 14. Alternatively, compound 13 may be treated in step 1 with a reducing agent such as sodium borohydride in the presence of a catalytic amount of nickel chloride preferably at 0° C. in an organic solvent such as methanol or tetrahydrofuran to form the aniline compound 14. One skilled in the art will appreciate that subjecting either compound (R)-13 or compound (S)-13 to a similar reaction sequence as described above for compound 13 may provide compounds of the present invention in the form of a single stereoisomer.

The aniline compound 14 which is made to undergo a reductive alkylation in step 2 by reacting compound 14 with an aldehyde of formula 8 preferably at elevated temperature to form an imine intermediate (not shown) which is subsequently reduced using sodium borohydride to form the substituted aniline compound 15. This two-step reaction sequence is preferably carried out in an organic solvent such as methanol.

Compound 15 is treated with an acid chloride of formula 9 in step 3 in the presence of a base such as triethylamine or pyridine in an organic solvent such as methylene chloride or tetrahydrofuran to form compounds of the previous general formula where $R^5$ is hydrogen. One skilled in the art will recognize that an acid chloride of formula 9 may be conveniently prepared starting from the corresponding carboxylic acid by methods well known in the literature.

General Scheme 6

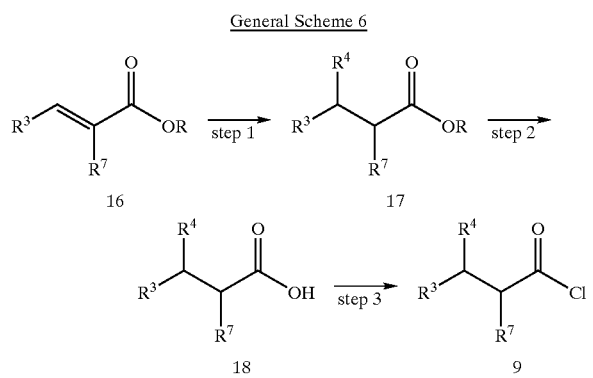

Referring to General Scheme 6, acid chloride compounds of formula 9 may be prepared starting from α,β-unsaturated ester 16 which is made to undergo a 1,4-conjugate addition in step 1 to form the β-substituted ester 17 (where $R^7$ is hydrogen) or α,β-disubstituted ester 17 (where $R^7$ is not hydrogen) Suitable reaction conditions include the use of organometallic reagents such as $(R^4)_2CuLi$ (where $R^4$ is alkyl) in an organic solvent such as diethyl ether at temperatures ranging from −78° C. to 0° C. Asymmetric conjugate additions of organometallic reagents to chiral α,β-unsaturated esters (where R is a chiral auxiliary such as a chiral cyclic diol) may used to provide optically active compounds of formula 17 as described in Fang et al. *Tetrahedron Asymmetry*, 1991, 2, 389–398 and elsewhere in the literature. β-Substituted or α,β-disubstituted ester 17 is saponified in step 2 using aqueous sodium hydroxide to form the carboxylic acid 18. Carboxylic acid 18 may be converted to acid chloride 9 in step 3 by treating with oxalyl chloride in the presence of a catalytic amount of dimethyl formamide in an organic solvent such as tetrahydrofuran or dichloromethane and by other methods well known in the literature. Alternatively, optically enriched β-branched carboxylic acids of formula 18 may be prepared as described by Hruby et al. *J. Org. Chem.* 1993, 58, 766–770 via asymmetric 1,4-addition of organocuprates to chiral α,β-unsaturated N-acyl-4-phenyl-2-oxazolidinones or by Beak et al. *J. Org. Chem.* 1996, 61, 4542–4554 via β-lithiation of β-aryl secondary amides followed by reaction with electrophiles. Other methods to produce optically enriched β-branched carboxylic acids of formula 18 include the use resolution techniques well known by those skilled in the art.

General Scheme 7

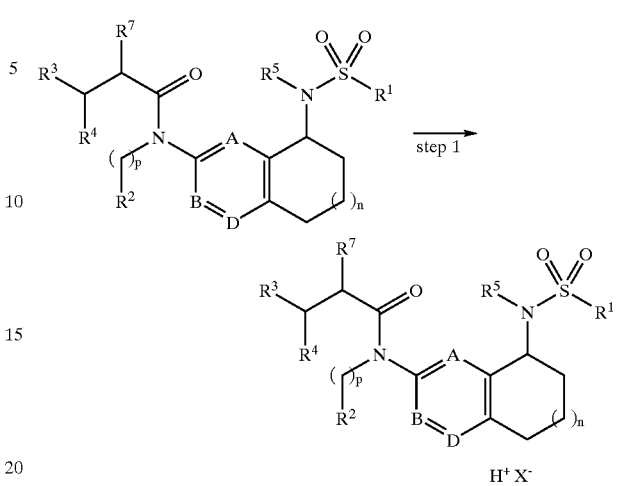

Referring to General Scheme 7, compounds of the present invention that have basic sites (e.g., a basic heteroaryl, a basic heterocyclo, or a basic amino group (such as imidazolyl or pyridyl)) may be treated in step 1 with an acid such as hydrochloric acid under anhydrous conditions to form a pharmaceutical salt. Preferably, the $R^2$ group is the basic moiety. Salt formulation provides a means of altering the physicochemical characteristics (such as aqueous solubility) of the parent compound as described by Berge et al. *J. Pharm. Sci.* 1977, 66, 1–19 and Gould *International Journal of Pharmaceutics* 1986, 33, 201–217.

The present invention is explained in greater detail in the Examples which follow. These examples are intended as illustrative of the invention, and are not to be taken as limiting thereof. Unless otherwise indicated, all references to parts and percentages are based on weight and all temperatures are expressed in degrees Celsius. The scope of the invention is not construed as merely consisting of the following examples.

EXAMPLES

Unless otherwise specified, all solvents and reagents were purchased from commercial suppliers and used without further purification. Analytical thin layer chromatography (TLC) was performed on Whatman Inc. 60 silica gel plates (0.25 mm thickness). Compounds were visualized under UV lamp or by developing with $KMnO_4/KOH$, ninhydrin, or Hanessian's solution. Flash chromatography was done using silica gel from Selectro Scientific (particle size 32–63). $^1H$ NMR and $^{13}C$ NMR spectra were recorded at 300 MHz and 75.5 MHz, respectively.

Compound Preparation

Tetrahydronaphthalene (tetralin) and benzocycloheptane, compounds of the previous formulae useful as potassium channel inhibitors in accordance with the present invention can be prepared in accordance with several sequential steps as illustrated with reference to the tetralin species in the preparations which follow.

Compound A

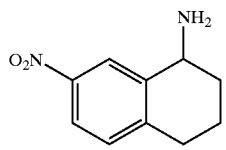

To 7-nitro-1-tetralone (10 g; 52.3 mmol) in methanol was added 40.8 g (529.0 mmol) of ammonium acetate followed by 4.36 g (69.4 mmol) of sodium cyanoborohydride. The reaction mixture was heated at 50° C. for 24 hours, cooled to room temperature and concentrated under reduced pressure. The residue was treated with 6N HCl (300 mL) and water (300 mL). The aqueous phase was washed with Et$_2$O ((diethylether) 400 mL), basified with KOH pellets to pH 12 and extracted with CH$_2$Cl$_2$ (3×200 mL). The organic phase was washed with water (200 mL) and dried over sodium sulfate. Compound A (7.75 g; 77%) was obtained as a brown solid and used in the next step without any additional purification or characterization.

Compound B

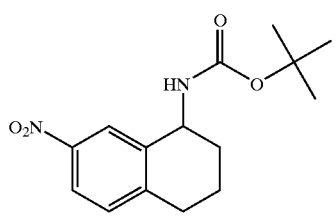

To compound A (7.30 g; 37.9 mmol) in acetonitrile (70 mL) was added N,N-diisopropylethylamine (7.5 mL; 39.2 mmol) followed by di-tert-butyl dicarbonate (10.8 g; 49.5 mmol). After stirring for 24 h (hours), the reaction mixture was diluted with ethyl acetate (200 mL), washed with 1N hydrochloric acid (70 mL), 1N sodium hydroxide (70 mL), water (70 mL), a saturated aqueous solution of sodium chloride (70 mL) and dried over sodium sulfate. Compound B (7.25 g; 65%) was obtained as a white solid.

Compound C, Compound (R)-C and Compound (S)-C

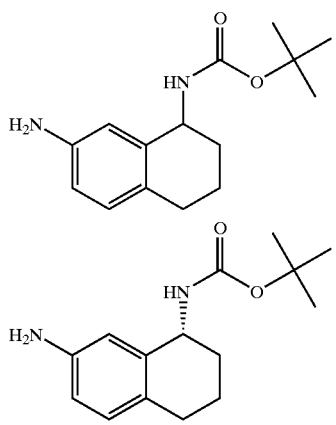

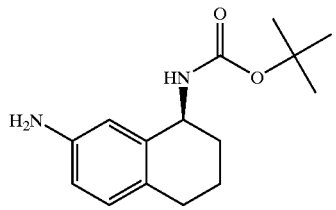

To compound B (3.62 g; 12.4 mmol) in tetrahydrofuran (THF) (55 mL) and methanol (17 mL) at 0° C. was added 1.87 g (49.5 mmol) of sodium borohydride followed by 0.13 g (1.0 mmol) of nickel (II) chloride. After 15 minutes, the ice bath was removed and the reaction was stirred at room temperature for 45 minutes at which time 1N sodium hydroxide (~50 mL) was added followed by ethyl acetate (100 mL). The organic layer was washed with water, a saturated aqueous solution of sodium chloride and dried over sodium sulfate. Compound C (3.05 g; 94%) was obtained as a white solid. Compound C can be resolved into single enantiomers using preparative chiral HPLC methods (Chiralpak AD column; 1 ml/min at room temperature; hexane/isopropanol/diethylamine 70/29.9/0.1; S-enantiomer retention time: 6.31 min, R-enantiomer retention time: 8.96 min).

Compound D

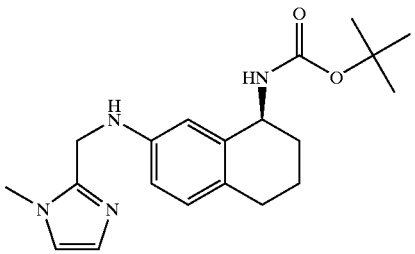

Compound C (1.00 g, 3.81 mmol) and 1-methylimidazole carboxaldehyde (525 mg, 4.76 mmol) were combined in methanol (20 mL). A large excess of sodium sulfate was added and the resulting suspension was heated to 45° C. with stirring for 4 hours. The reaction mixture was cooled to room temperature and sodium borohydride (433 mg, 11.4 mmol) was added. After 18 hours, the reaction was quenched with saturated aqueous solution of sodium bicarbonate and the methanol was removed by rotary evaporation. The residue was diluted with ethyl acetate, washed with water, and dried over sodium sulfate. After evaporation of the solvents, the crude product was purified by flash column chromatography using a solution of 5% methanol in ethyl acetate to give a white foam (1.24 g, 91%): $^1$H NMR (CD$_3$OD) δ 6.99 (s, 1H), 6.84 (d, J=3.8 Hz, 1H), 6.81 (s, 1H), 6.60 (s, 1H), 6.57 (d, J=6.4 Hz, 1H), 4.61 (m, 1H), 4.32 (s, 2H), 3.70 (s, 3H), 2.62 (m, 2H), 1.92 (m, 2H), 1.71 (m, 1H), 1.47 (s, 9H); LC/MS (EI) found (M+1) 357.2.

Compound O

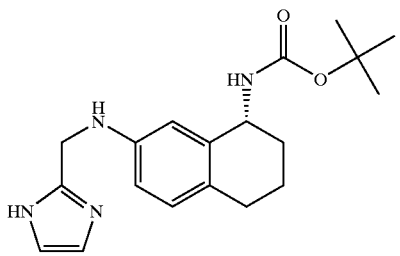

Compound C (500 mg, 1.91 mmol) and 2-imidazole carboxaldehyde (229 mg, 2.38 mmol) were combined in 10 mL of dry methanol. A large excess of sodium sulfate was added. The suspension was heated to 45° C. with stirring for 14 h (hours). It was then cooled to rt (room temperature). Sodium borohydride (238 mg, 6.29 mmol) was then added to the suspension and the reaction mixture was stirred at rt for 2 h. Water (<0.5 mL) was added to the reaction mixture to quench any unreacted sodium borohydride. More sodium sulfate was added to dry the excess water. After filtration of the dried solution using ethyl acetate and methanol to wash, the solvents were removed. The residue was then recrystallized from methanol to yield compound O as an off-white foam (512 mg, 78%): $^1$H NMR (CD$_3$OD) δ 6.94 (broad s, 2H), 6.81 (d, J=8.4 Hz, 1H), 6.55 (s, 1H), 6.47 (m, 1H), 4.56 (m, 1H), 4.32 (s, 2H), 2.62 (m, 2H), 1.89 (m, 2H), 170 (m, 2H), 1.46 (s, 9H); LC/MS (EI) found (M+1) 343.2.

Compound E

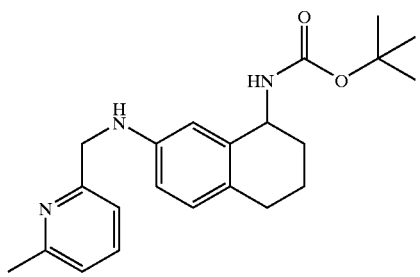

Compound C (1.30 g; 5.0 mmol) and 6-methyl-2-pyridine carboxaldehyde (0.60 g; 5.0 mmol) in methanol (20 mL) was stirred overnight, cooled to 0° C. then sodium borohydride (560 mg; 14.8 mmol) was added portionwise. After 2.5 hours, the reaction mixture was quenched with 1 N sodium hydroxide (20 mL), diluted with ethyl acetate (40 mL), washed with water, a saturated aqueous solution of sodium chloride and dried over sodium sulfate Purification by flash chromatography (3:2 hexanes:ethyl acetate) gave compound E (1.57 g; 86%) as a yellow syrup. $^1$H NMR (300 MHz, CDCl$_3$) δ 1.47 (9 H, s), 1.70–1.78 (4 H, m), 1.98–2.04 (1 H, m), 2.57 (3 H, s), 2.62–2.78 (2 H, m),4.39 (2 H, s), 4.76 (2 H, bs), 6.53 (1 H, dd, J=2.5, 8.5 Hz), 6.59 (1 H, d, J=2.5 Hz), 6.88 (1 H, d, J=8.4 Hz), 7.03 (1 H, d, J=7.7 Hz), 7.12 (1 H, 7.7 Hz), 7.52 (1 H, t, J=7.6 Hz); MS m/z (M+1) 368.2

Compound F

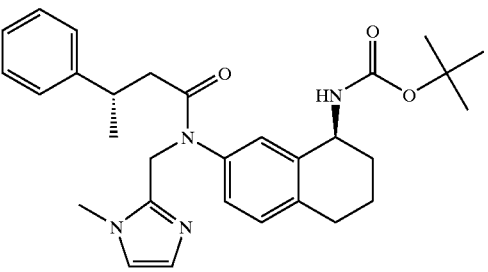

(S)-Phenylbutyric acid (86 mg, 0.53 mmol) and oxalyl chloride (51 μL, 0.59 mmol) were combined in dry methylene chloride (2 mL). Two drops of dimethyl formamide were added. After 1 hour, the methylene chloride was removed by rotary evaporation and the residue was dissolved in tetrahydrofuran (2 mL). Compound D (150 mg, 0.421 mmol) and triethylamine (0.13 mL, 0.93 mmol) were added. After 2.5 hours, the reaction mixture was diluted with ethyl acetate, washed with a saturated aqueous solution of sodium bicarbonate, and dried over sodium sulfate. Purification by flash column chromatography using a solution of 1% methanol in ethyl acetate gave compound F as a white foam (188 mg, 89%): $^1$H NMR (CD$_3$OD) δ 7.24 (m, 3H), 7.16 (m, 1H), 7.03 (m, 4H), 6.96 (s, 1H), 6.72 (s, 1H), 6.56 (broad s, 1H), 4.96 (d, J=15.0 Hz, 1H), 4.82 (d, J=15.0 Hz, 1H), 4.62 (m, 1H), 3.41 (s, 3H), 3.30 (m, 2H), 2.74 (m, 2H), 2.38 (m, 2H), 2.00–1.87 (m, 2 H), 1.75 (m, 2H), 1.50 (s, 9H), 1.18 (d, J=7.2 Hz, 3H); LC/MS (EI) found for (M+1) 503.3.

Compound P

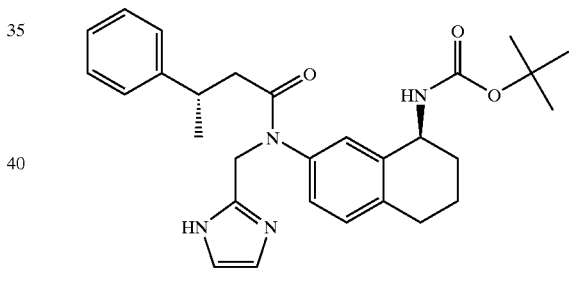

(S)-3-Phenylbutyric acid (216 mg, 1.31 mmol) and oxalyl chloride (140 μL, 1.7 mmol) were combined in 10 mL of dry methylene chloride. Two drops of DMF were added to catalyze the reaction. Bubbling was visible at this time. After 1 h, the methylene chloride was removed from the solution by rotary evaporation at rt. The residue was dissolved in 6 mL of THF. Compound O (300 mg, 0.876 mmol) dissolved in 3 mL of THF and triethylamine (0.27 mL, 2.0 mmol) were added and the solution was stirred for 5 h. A saturated aqueous solution of sodium bicarbonate was added to the reaction mixture and then it was extracted with ethyl acetate. The organic layers were combined and dried over sodium sulfate. After evaporation of the solvents, the resulting residue was dissolved in 9 mL of methanol and 3 mL of 4 M sodium methoxide in methanol. This solution was stirred for 18 h at rt. The methanol was removed and water was added. The mixture was then extracted with ethyl acetate and dried over sodium sulfate. After evaporation of the solvents, the resulting residue was purified by flash column chromatography using a solution of 1% methanol in ethyl acetate. This yielded compound P as a white foam (182 mg, 43%): $^1$H NMR (CD$_3$OD) δ 7.18 (m, 1H), 7.08 (m, 1H), 7.02

(m, 2H), 6.93 (m, 7H), 4.99 (s, 1H), 4.76 (d, J=10.3 Hz, 1H), 4.63 (m, 1H), 3.26 (m, 1H), 2.74 (m, 2H), 2.59 (m, 2H), 1.95 (m, 2H), 1.75 (m, 2H), 1.47 (s, 9H), 1.22 (d, J=7.5 Hz, 3H); LC/MS (EI) found (M+1) 489.3.

Compound Q

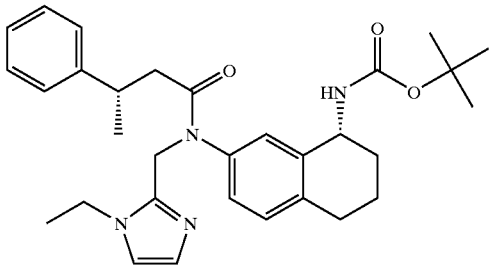

Compound P (70 mg, 0.14 mmol), potassium carbonate (99 mg, 0.72 mmol) and iodoethane (26 mg, 0.17 mmol) were combined in 1 mL of dry dimethyl formamide. (DMF) This mixture was stirred at rt for 64 h. Water was added and the mixture was extracted with ethyl acetate and dried over sodium sulfate. After filtration and evaporation, the residue was purified by flash column chromatography using 2% methanol in ethyl acetate to yield compound Q as an oil (56 mg, 76%): $^1$H NMR (CD$_3$OD) δ 7.22 (m, 3H), 7.16 (m, 1H), 7.05 (m, 4H), 6.91 (s, 1H), 6.73 (s, 1H), 6.55 (broad s, 1H), 4.89 (m, 2H), 4.62 (m, 1H), 3.81 (m, 2H), 3.29 (m,1H), 2.74 (m, 2H), 2.35 (m, 2H), 2.03–1.85 (m, 2H), 1.73 (m 2H), 1.49 (s, 9H), 1.18 (d, J=7.2 Hz, 3H); LC/MS (EI) found (M+1) 517.0.

Compound G

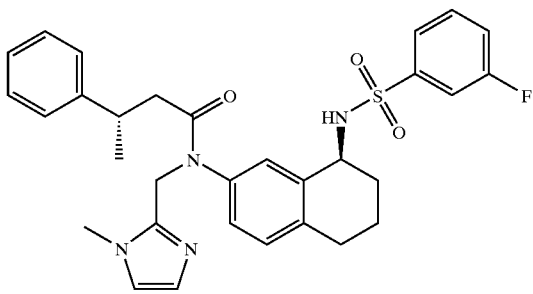

Compound F (28 mg, 0.050 mmol) was dissolved in a solution of 4M HCl in 1,4-dioxane (0.4 mL) and stirred for 1 hour at room temperature. The 1,4-dioxane was removed by rotary evaporation to give a yellow solid residue. The residue was treated with dry tetrahydrofuran (0.5 mL) followed by 3-fluorobenzenesulfonyl chloride (15 mg, 0.075 mmol) and triethylamine (16 μL, 0.11 mmol). This mixture was stirred at rt for 4 h. After 4 hours of stirring at room temperature, the reaction mixture was diluted with ethyl acetate, washed with a saturated aqueous solution of sodium bicarbonate, and dried over sodium sulfate. Purification by flash column chromatography using a solution of 1% methanol in ethyl acetate gave compound G (Compound (4)) as a white solid (19 mg, 68%): $^1$H NMR (CD$_3$OD) δ 7.76 (d, J=7.8 Hz, 1H), 7.68–7.57 (m, 2H), 7.40 (dt, J=2.4, 8.5 Hz, 1H), 7.20 (m, 4H), 7.01 (m, 4H), 6.69 (s, 1H), 6.43 (broad s, 1H), 4.34 (m, 1H), 3.44 (s, 3H), 3.34 (s, 2H), 3.23 (q, J=7.2 Hz, 1H), 2.70 (m, 2H), 2.28 (m, 2H), 1.85 (m, 1H), 1.71 (m, 3H), 1.16 (d, J=7.1 Hz, 3H). LC/MS (EI) found (M+1) 561.3.

Compound H

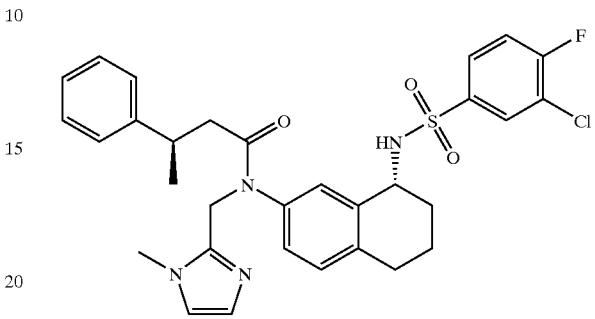

Compound H (Compound (23)) was prepared as described for compound G using (R)-3-phenylbutyric acid in place of (S)-3-phenylbutyric acid and 3-chloro-4-fluorobenzenesulfonyl chloride in place of 3-fluorobenzenesulfonyl chloride. $^1$H NMR (CD$_3$OD) δ 8.06 (dd, J=2.2, 6.8 Hz, 1H), 7.91 (m, 1H), 8.06 (t, J=8.7 Hz, 1H) 7.26–7.12 (m, 5H), 7.00 (m, 4H), 6.69 (s, 1H), 6.49 (broad s, 1H), 4.35 (m, 1H), 3.46 (s, 3H), 3.34 (s, 2H), 3.26 (m, 1H), 2.72 (m, 2H), 2.32 (m, 2H), 1.90–1.72 (m, 4H), 1.16 (d, J=6.9 Hz, 3H). LC/MS (EI) found (M+1) 595.4.

Compound I

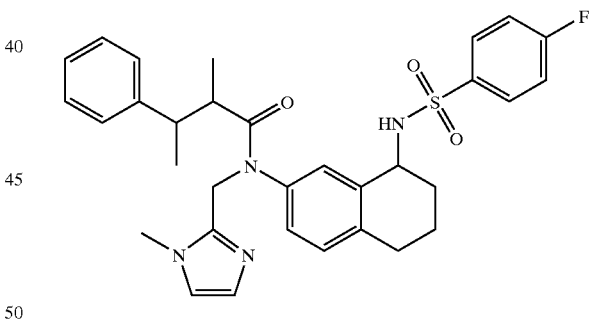

Compound I (Compound (229)) was prepared as described for compound G using 2-methyl-3-phenylbutyric acid in place of (S)-3-phenylbutyric acid and 4-fluorobenzenesulfonyl chloride in place of 3-fluorobenzenesulfonyl chlroride to give a mixture of three diastereomers. $^1$H NMR (acetone-d$_6$) δ 8.03 (dd, J=6.7, 13.7 Hz, 2H), 7.66 (s, 1H), 7.49 (s,1H), 7.36 (dd, J=8.5, 15.3 Hz, 2H), 7.20 (m, 5H), 7.02 (m, 3H), 5.44 (m, 1H), 5.24 (m, 1H), 4.47 (m, 1H), 4.13 (s, 3H), 2.90 (m, 1H), 2.71 (m, 2H), 2.51(m, 1H), 1.87–1.66 (m, 4H), 1.26 (d, J=6.8 Hz, 3H, diastereomer A), 1.21 (d, J=6.9 Hz, 3H, diastereomer B), 1.10 (d, J=7.0 Hz, 3H, diastereomer C), 0.89 (d, J=6.8 Hz, 3H, diastereomer A), 0.76 (d, J=6.6 Hz, 3H, diastereomer B), 0.66 (d, J=6.8 Hz, 3H, diastereomer C).

Compound R

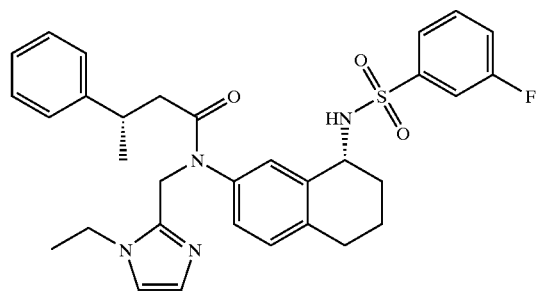

Compound Q (56 mg, 0.11 mmol) was dissolved in 1 mL of a 4M HCl in dioxane solution and stirred at rt for 1 h. The dioxane was then removed by rotary evaporation to give a yellow solid residue. To this residue was added 1 mL dry THF. Then triethylamine (48 µL, 0.34 mmol) was added and the mixture stirred 5 minutes. 3-Fluorobenzenesulfonyl chloride (40 mg, 0.21 mmol) in o.5 mL THF was added and the mixture was stirred at rt for 14 h. A saturated aqueous solution of sodium bicarbonate was added to the reaction mixture and then it was extracted with ethyl acetate. The organic layers were combined and dried over sodium sulfate. After evaporation of the solvents, the resulting residue was purified by flash column chromatography using a solution of 2% methanol in ethyl acetate. This yielded compound R (Compound (230)) as a white solid (44 mg, 70%): $^1$H NMR (CD$_3$OD) δ 7.76 (d, J=7.8 Hz, 1H), 7.68–7.57 (m, 2H), 7.39 (dt, J=2.1, 8.5 Hz, 1H), 7.21 (m, 2H), 7.15 (q, J=7.2 Hz, 1H), 7.02 (m, 4H), 6.71 (s, 1H), 6.44 (broad s, 1H), 4.88 (m, 1H), 4.67 (m, 1H), 4.35 (m, 1H), 3.84(m, 2H), 3.23 (q, J=7.2 Hz, 1H), 3.34 (s, 2H), 2.70 (m, 2H), 2.29 (m, 2H), 1.84 (m, 1H), 1.70 (m, 3H), 1.29 (t, J=7.0 Hz, 3H), 1.16 (d, J=7.2 Hz, 3H); LC/MS (EI) found (M+1) 574.9.

Compound S

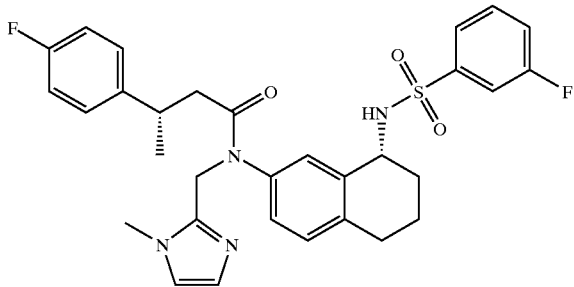

Compound S (Compound (231)) was prepared as described for compound G using (S)-3-(4-fluorophenyl) butyric acid in place of (S)-3-phenylbutyric acid. $^1$H NMR (CD$_3$OD) δ 7.76 (d, J=7.9 Hz, 1H), 7.68–7.57 (m, 2H), 7.40 (dt, J=2.1, 8.5 Hz, 1H), 7.05 (m, 6H), 6.70 (s, 1H), 6.51 (m, 2H), 4.36 (m, 1H), 3.47 (s, 3H), 3.30 (s, 2H), 3.24 (m, 1H), 2.70 (m, 2H), 2.29 (m, 2H), 1.84 (m, 1H), 1.70 (m, 3H), 1.15 (d, J=7.1 Hz, 3H). LC/MS (EI) found (M+1) 579.4.

Compound N

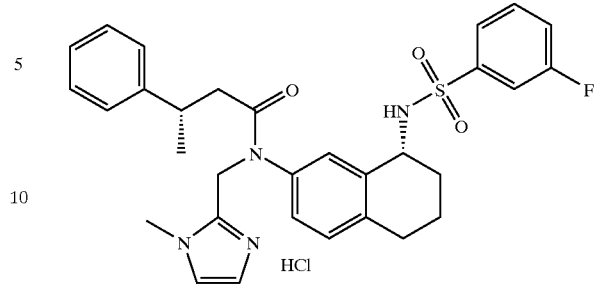

Compound G (103 mg, 0.184 mmol) was dissolved in 3 mL of dry THF. A 4 M HCl solution in dioxane (0.18 mL) was added. The reaction solution was stirred at rt for 36 h. The solvent were then removed and the resulting amorphous solid was dried further by vacuum for 10 h. The solid was dissolved in a 5:1 mixture of water:CH$_3$CN and filtered through a Millipore syringe filter. The resulting clear solution was lyophilized for 24 h yielding 108 mg (99%) of the product (Compound N (Compound (2))) as a salt.

Compound J

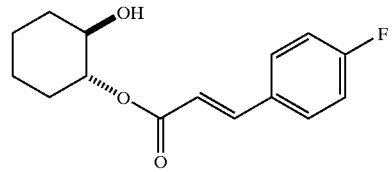

4-Fluorocinnamic acid (2.00 g, 12.0 mmol) was dissolved in dry CH$_2$Cl$_2$ (50 mL) and then cooled to 0° C. Oxalyl chloride (1.17 mL, 13.5 mmol) was added followed by three drops of dimethyl formamide. The ice bath was removed and the reaction mixture was allowed to stir at room temperature for 1.5 hours at which time the volatiles were removed to give an off white solid that was 4-fluorocinnamoyl chloride. This acid chloride was added as a dry methylene chloride solution (6 mL ) to another solution containing trans-1,2-diolcyclohexane (1.12 g, 9.63 mmol), pyridine (0.58 mL, 7.22 mmol), and 4-(N,N-dimethylamino)pyridine (118 mg, 0.963 mmol) in dry methylene chloride (40 mL). The reaction mixture was stirred at room temperature for 16 hours at which time the reation mixture was diluted with ethyl acetate, washed with water, and dried over sodium sulfate. Purification by flash column chromatography using 4:1 hexanes:ethyl acetate as the eluent yielded 2.03 g (80%) of compound J as a white amorphous solid: $^1$H NMR (CDCl$_3$) δ 7.66 (d, J=16.1 Hz, 1H), 7.51 (dd, J=5.3, 8.7 Hz, 2H), 7.07 (t, J=8.6 Hz, 2H), 6.38 (d, J=16.0 Hz, 1H), 4.71 (m, 1H), 3.54 (m, 1H), 2.10 (m, 2H), 1.73 (m, 2H), 1.34 (m, 4H).

Compound K

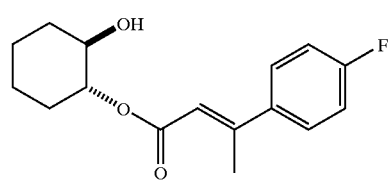

Copper(I)bromide-dimethylsulfide complex (2.06 g, 10.0 mmol) was suspended in 35 mL of dry ether under an inert atmosphere and cooled to −25° C. A 4M solution of methyllithium in ether (14.3 mL) was slowly added. The solution was initially bright yellow then cleared upon the addition of the entire methyllithium solution. The resulting solution was stirred 30 min more at −25° C. after the addition was complete. Compound J (529 mg, 2.00 mmol) dissolved in 6 mL of dry ether was then slowly added to the reaction mixture. The mixture again turned bright yellow. Stirring was continued for another 2 h. A saturated solution of $NH_4Cl$ was then added and the mixture was stirred vigorously at rt for 1 h until a dark blue color was seen in the aqueous layer. This was then separated. The aqueous layer was extracted with ether and the organic layers were combined and dried over sodium sulfate. Purification by flash column chromatography using 4:1 hexanes:ethyl acetate as the eluent gave 380 mg (68%) of compound K a white amorphous solid: $^1H$ NMR ($CDCl_3$) δ 7.19 (dd, J=5.4, 8.5 Hz, 2H), 6.98 (t, J=8.7 Hz, 2H), 4.50 (m, 1H), 3.46 (m, 1H), 3.27 (m, 1H), 2.61 (d, J=7.7 Hz, 2H), 1.99 (m, 2H), 1.86 (m, 2H), 1.67 (m, 4H), 1.29 (d, J=7.2 Hz, 3H).

Compound L (3-(4-Fluorophenyl)-butyric acid)

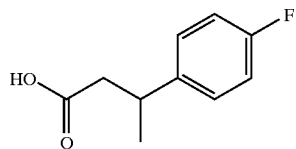

Compound K (1.15 g, 3.98 mmol) and KOH (335 mg, 5.97 mmol) were dissolved in absolute ethanol and heated to 70° C. until compound K could not be detected by thin layer chromatography (3.5 h). The solution was then cooled to rt and the ethanol removed. Water was added and washed twice with ethyl acetate. The aqueous layer was then acidified to a pH<2 with 6 N HCl aq solution. The aqueous layer was then extracted with ethyl acetate. The organic layer were combined and dried over sodium sulfate to yield 3-(4-fluorophenyl)-butyric acid as an off white amorphous solid in a quantitative amount: $^1H$ NMR ($CDCl_3$) δ 7.18 (dd, J=5.3, 8.6 Hz, 2 H), 6.98 (t, J=8.6 Hz, 2H), 3.26 (m, 1H), 2.06 (m, 2H), 1.30 (d, J=6.9 Hz, 3H).

Compound M

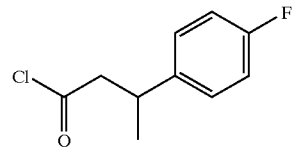

3-(4-Fluorophenyl)butyric acid (100 mg, 0.549 mmol) and oxalyl chloride (57 μL, 0.659 mmol) were dissolved in dry $CH_2Cl_2$. A catalytic amount (one drop) of DMF was added. The production of gases could be observed. The solution was stirred at rt for 1 h and then the volatiles were removed on a rotary evaporator. The resulting oily residue was dried further for 10 min by vacuum and then used without additional purification.

Compound T

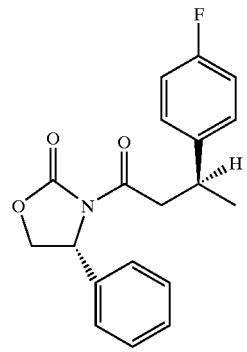

To a solution of solution of $CuBr.Me_2S$ (561 mg; 2.73 mmol) in THF (6.5 mL) and $Me_2S$ (dimethylsulfide) (3.25 mL) at −40° C. was added 5.46 mL (5.46 mmol) of 1.0 M 4-fluorophenyl magnesium bromide in THF. After 15 min, the appropriate oxazolidinone (see Hruby et al. *J. Org. Chem.* 1993, 58, 766–770) (420 mg; 1.82 mmol) in THF (3.25 mL) was added dropwise. After 1 h from −40° C. to −15° C., the reaction was quenched with sat. $NH_4Cl$. The reaction mixture was concentrated under reduced pressure, diluted with EtOAc (ethyl acetate) (20 mL), washed with 10% $NH_4OH$ (2×), $H_2O$, brine and dried over $Na_2SO_4$. Purification by flash chromatography (3:1; hexanes-EtOAc) gave a white solid which was recrystallized from EtOAc-hexane to give the pure oxazolidinone compound T (450 mg; 75%) as a white solid. $^1H$ NMR (300 MHz, $CDCl_3$) δ 1.24 (3 H, d, J=7.0 Hz), 2.98 (1 H, dd, J=7.3, 15.7 Hz), 3.31 (1 H, dq, J=7.1 Hz, 7.1 Hz), 3.49 (1 H, dd, J=7.3, 15.8 Hz), 4.21 (1 H, dd, J=4.0, 8.9 Hz), 4.65 (1 H, dd, J=8.9, 8.9 Hz), 5.39 (1 H, dd, J=3.9, 8.8 Hz), 6.91 (2 H, dd, J=6.6, 6.6 Hz), 7.04–7.16 (4 H, m), 7.26–7.38 (3 H, m).

Compound U

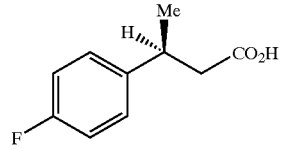

To the acyloxazolidinone compound T (430 mg; 1.31 mmol) in THF (5.9 mL) and $H_2O$ (1,5 mL) at −5° C. was added 0.59 mL of 30% $H_2O_2$ followed by 0.8 M LiOH (2.62 mL). After stirring at 0° C. for 2 h, 4 mL of 1.3 M $Na_2SO_3$ was added. The aqueous layer was washed with $CH_2Cl_2$ (3×5 mL), acidified to pH 1 with 6 N HCl and extracted with $CH_2Cl_2$ (2×10 mL). The combined organic phase was washed with $H_2O$ and dried over $Na_2SO_4$ to give the acid compound U (221 mg; 92%) as a colorless oil. $^1H$ NMR (300 MHz, $CDCl_3$) δ 1.30 (3 H, d, J=6.9 Hz), 2.56 (1 H, dd, J=7.8, 15.6 Hz), 2.63 (1 H, dd, J=7.2, 15.6 Hz), 3.26 (1 H, ddq, J=6.9, 7.2, 7.8), 6.98 (2 H, dd, J=8.7, 8.7 Hz), 7.17 (2 H, dd, J=5.5, 7.6 Hz).

Using the principles and techniques involved in the preparations of Compounds A through U (and methods available from the literature, such as WO 98/04521 and WO 99/37607), and appropriate starting materials, which will be well-understood by those skilled in the art, a variety of other compounds falling within the scope of the present invention can be synthesized. In this regard, compounds listed in the following Table 2 have been synthesized.

TABLE 2

| Example | Structure | mass spec m/z |
|---|---|---|
| 1 | 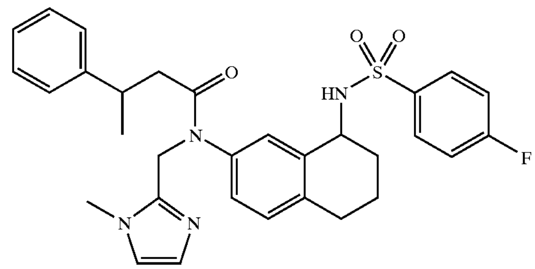 | 561.2 (M + H) |
| 2 | 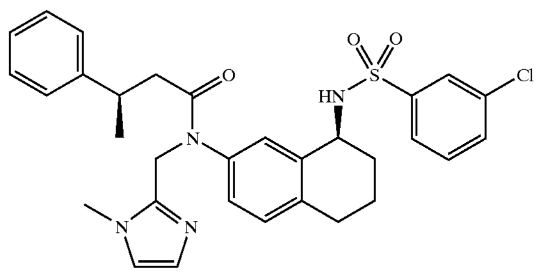 | 577.4 (M + H) |
| 3 | 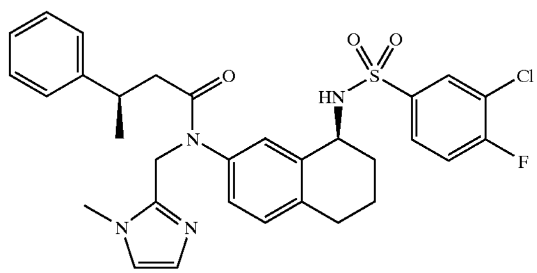 | 595.4 (M + H) |
| 4 | 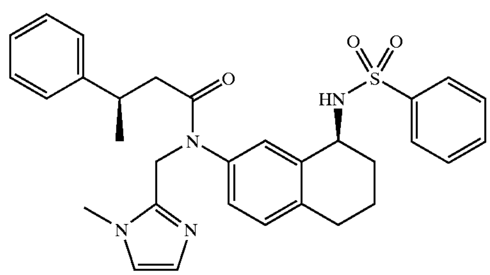 | 543.4 (M + H) |
| 5 | 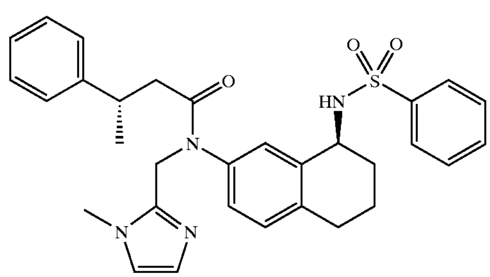 | 543.4 (M + H) |

TABLE 2-continued
| Example | Structure | mass spec m/z |
|---|---|---|
| 6 | 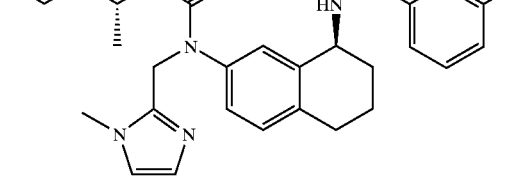 | 577.4 (M + H) |
| 7 | 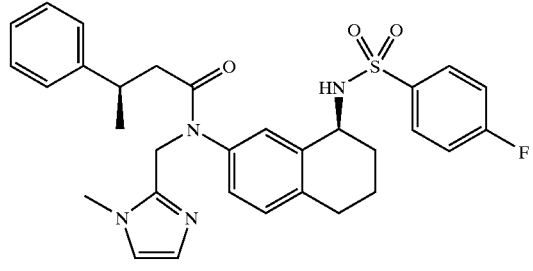 | 561.4 (M + H) |
| 8 | 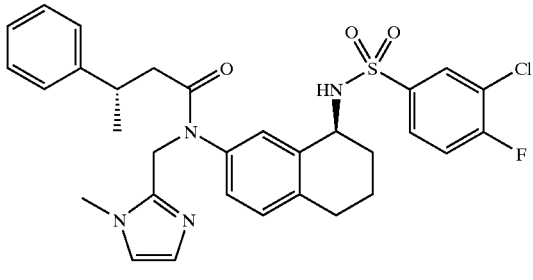 | 595.4 (M + H) |
| 9 | 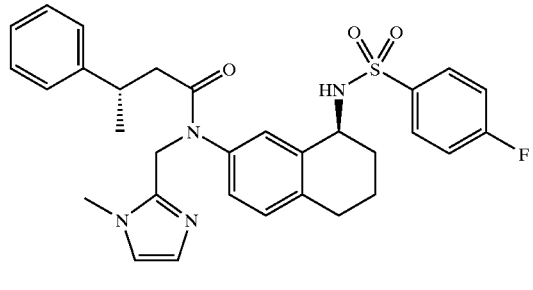 | 561.4 (M + H) |
| 10 | 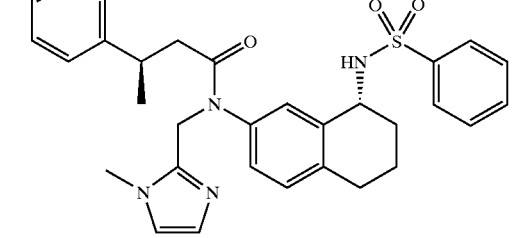 | 543.3 (M + H) |

TABLE 2-continued
| Example | Structure | mass spec m/z |
|---|---|---|
| 11 | 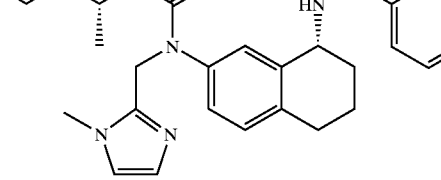 | 543.3 (M + H) |
| 12 | 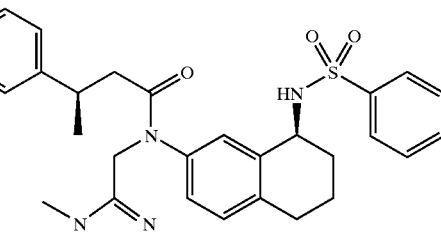 | 561.2 (M + H) |
| 13 | 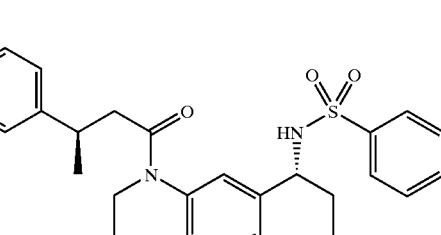 | 561.1 (M + H) |
| 14 | 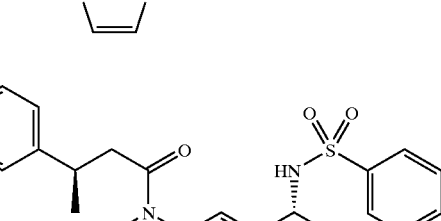 | 577.3 (M + H) |
| 15 | 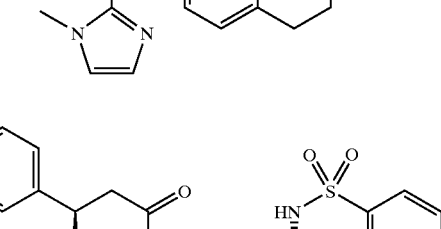 | 595.2 (M + H) |

TABLE 2-continued

| Example | Structure | mass spec m/z |
|---|---|---|
| 16 | 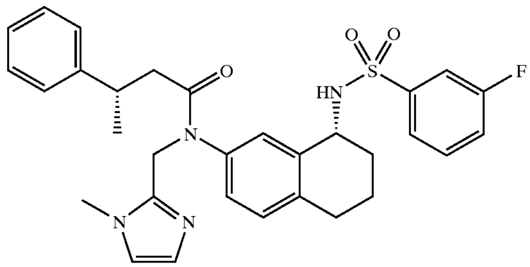 | 561.3 (M + H) |
| 17 | 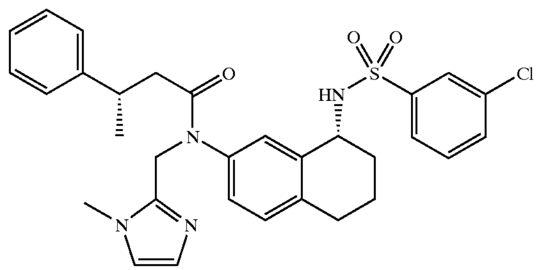 | 577.3 (M + H) |
| 18 | 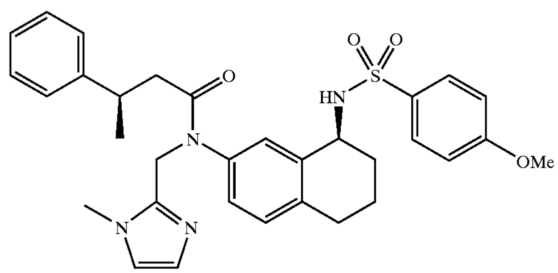 | 573.3 (M + H) |
| 19 | 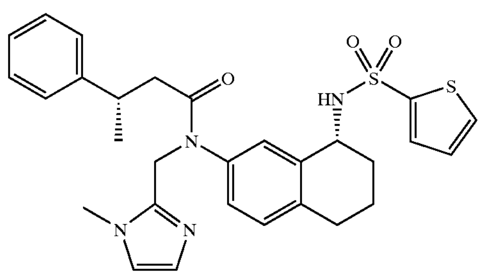 | 549.3 (M + H) |
| 20 | 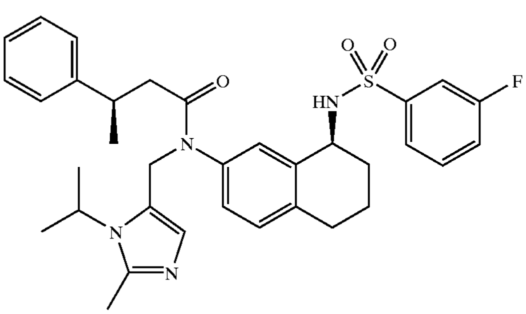 | 603.4 (M + H) |

TABLE 2-continued

| Example | Structure | mass spec m/z |
|---|---|---|
| 21 | 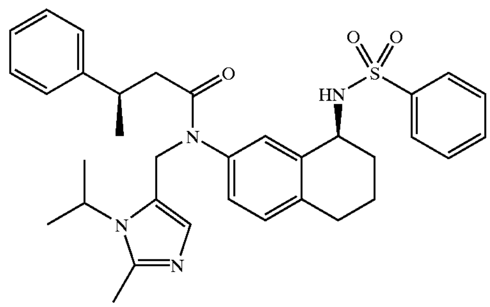 | 585.2 (M + H) |
| 22 | 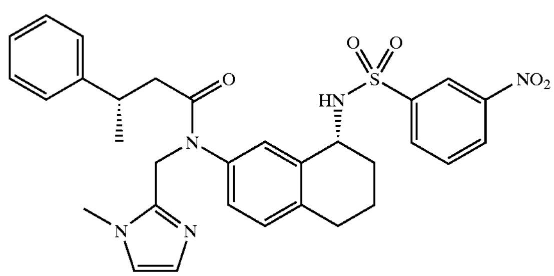 | 588.4 (M + H) |
| 23 | 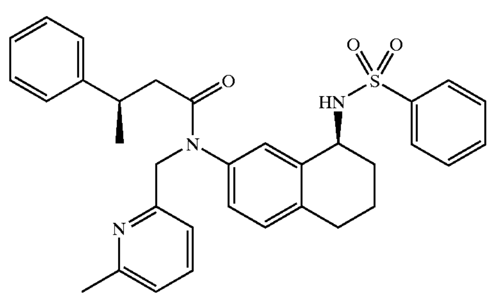 | 554.3 (M + H) |
| 24 | 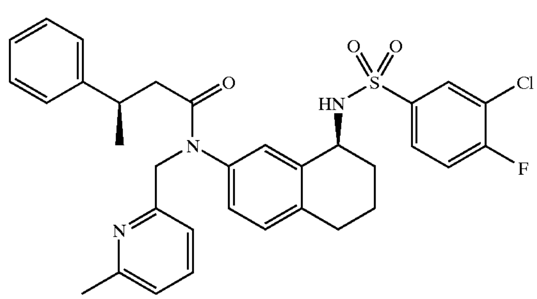 | 606.5 (M + H) |
| 25 | 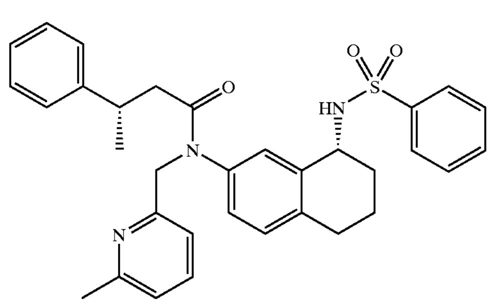 | 554.2 (M + H) |

TABLE 2-continued

| Example | Structure | mass spec m/z |
|---------|-----------|---------------|
| 26 | 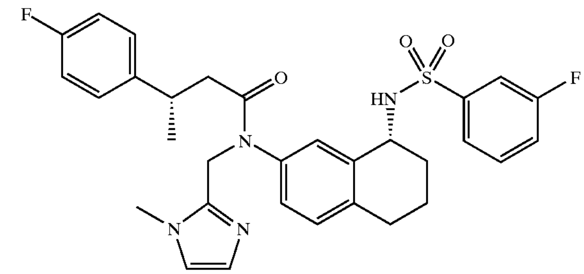 | 579.4 (M + H) |

EXAMPLES

BioAssays $^{86}$Rb Efflux Assays:

Cells stably transfected with cDNA for human Kv1.5 (in pcDNA3 vector) were grown as confluent monolayers in 96 well tissue culture plates in MEM alpha with 10% heat inactivated fetal bovine serum and 400 μg/ml G418. Cells were incubated overnight in growth media containing 1 μCi/ml $^{86}$Rb to permit intracellular uptake of the isotope. At the end of the incubation period, the $^{86}$Rb solution was aspirated and the cells washed three times with Earls Balanced Salt Solution (EBSS) which contained (in mM) 132 NaCl, 5.4 KCl, 1.8 CaCl$_2$, 0.8 MgCl$_2$ 10 HEPES and 5 glucose. The cells were then preincubated for 10 minutes at room temperature in 100 μl/well of EBSS or EBSS containing test compounds. At the end of this period the wells were aspirated and to each well was then added 100 μl of a modified EBSS solution containing 70 mM KCl (NaCl replaced by KCl) and the compound to be tested. The high KCl concentration was utilized to depolarize the cells to membrane potentials that would activate Kv1.5 channels. After a 1 minute incubation in 70 mM KCl EBSS plus test compound, the solution was removed and placed into the appropriate well of a 96 well counting plate for analysis. Finally 100 μl of 0.1% sodium dodecyl sulfate in EBSS was added to each well to lyse the cells. The lysate was taken for analysis to determine final cell content of $^{86}$Rb. Samples were counted in a Wallac Microbeta liquid scintillation counter by Cerenkov emission. Efflux can be expressed as a percentage of the initial cell content of $^{86}$Rb.

Electrophysiological Studies

Electrophysiological recordings of potassium currents in Chinese hamster ovary cells stably expressing the gene construct for the Kv1.5 potassium channel subunit were performed using the whole cell configuration of the patch clamp technique (Hamill et al., *Pflugers Archiv* 391:85, 1981). Cell lines expressing Kv1.5 were prepared using standard techniques known to those skilled in the art. Cells were plated on glass coverslips at a density of 2×10$^4$ cells/coverslip and used within 24–48 hours. Solutions used for electrophysiological recordings were as follows. Extracellular bathing solutions typically contain (in mM) 132 NaCl, 5.4 KCl, 1.8 CaCl$_2$, 0.8 MgCl$_2$, 10 HEPES, 5 glucose at pH 7.3. Electrode pipette solutions (intracellular solution) for measuring Kv1.5 typically contain (in mM) 100 KF, 40 KCl, 5 NaCl, 2 MgCl$_2$, 5 EGTA, 10 HEPES and 5 glucose at pH 7.4 with KOH, 295 mOsm and had a resistance of 1–2 MΩ. The coverslips were placed in a small chamber (volume ~200 μl) on the mechanical stage of an inverted microscope and perfused (approximately 2 ml/min) with extracellular recording solution. Drug was applied using a series of narrow-bore glass capillary tubes (inner diameter ~100 μm) positioned approximately 200 μm from the cell.

FIG. 4 shows representative hKv1.5 currents that were recorded using the whole-cell voltage clamp technique. h-Kv1.5 currents were elicited by depolarization to 10+mV from a holding potential of −0 mV once every 10 seconds. As soon as the current recording were stable, a compound representative of the present invention was superfused over the cell until steady-state block was observed. Using this technique, the effects of the compound on peak and steady-state current were determined at progressively increasing compound concentrations.

The testing results of selected compounds from Table 2 using this assay and the techniques described above are reported in Table 3 as the percent inhibition of Kv1.5 potassium channel currents at a single concentration of 0.1 μM.

TABLE 3

STEADY-STATE AND PEAK CURRENT INHIBITION OF SELECTED COMPOUNDS

| Example number (from Table 2) | Steady-state Current Inhibition at 0.1 μM (%) | Peak current inhibition at 0.1 μM (%) |
|---|---|---|
| 1 | 67 | 42 |
| 2 | 96 | 86 |
| 3 | 93 | 84 |
| 4 | 89 | 86 |
| 5 | 78 | 45 |
| 6 | 81 | 30 |
| 9 | 61 | 53 |
| 11 | 91 | 76 |
| 12 | 85 | 68 |
| 16 | 100 | 88 |
| 17 | 97 | 84 |
| 18 | 84 | 72 |
| 19 | 79 | 53 |
| 20 | 64 | 52 |
| 21 | 67 | 58 |
| 23 | 90 | 75 |
| 24 | 65 | 48 |
| 25 | 50 | 26 |
| 26 | 76 | 52 |

Action-Potential Clamp Experiments

"Action-potential" clamp experiments measure the Kv1.5 potency of compound with fast (characteristic of prior art compounds such as those described WO 99/37607) and slow (characteristic of the present invention) off-rate under physiological conditions. Single human atrial myocytes were isolated from right atrial appendages from patients undergoing coronary artery bypass surgery. Action potentials were recorded in the current clamp mode of the whole cell patch clam technique. A representative action potential waveform was saved to elicit Kv1.5 currents as the voltage command in whole-cell, voltage-clamp experiments with CHO cells stably expressing hKv1.5. Action potential waveforms were delivered at a frequency of 1 Hz at a temperature of 37° C. Representative results are presented in FIG. 5. As illustrated in FIG. 5, compounds with fast off-rates (i.e., compounds representative of the prior art) were relatively ineffective as Kv1.5 blockers under these conditions. In contrast, compounds with slow off-rates (i.e those exhibiting peak current inhibition, characteristic of the compounds of the present invention) were potent Kv1.5 blockers under physiological conditions.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention. Those skilled in the art will recognize variations in the processes as described above and will recognize appropriate modifications based on the above disclosure for making and using the compounds of the invention.

We claim:

1. A compound having the following formula:

wherein $R^1$, $R^2$ and $R^3$ are independently selected from the group consisting of aryl, heteroaryl and heterocyclo;

$R^4$ is selected from the group consisting of alkyl, hydroxy, alkoxy, carbocycloalkyl and amino;

$R^5$ and $R^6$ are independently selected from the group consisting of hydrogen and alkyl;

$R^7$ is selected from the group consisting of hydrogen, alkyl, hydroxy, alkoxy and amino;

$R^8$ is selected from the group consisting of hydrogen and alkyl;

$R^9$, $R^{10}$ and $R^{11}$ are independently selected from the group consisting of hydrogen, alkyl and halo;

G is selected from the group consisting of a direct bond and a lower alkylene;

A, B and D are independently selected from the group consisting of a substituted carbon atom, a nitrogen atom, and N-oxide, wherein at least one of A, B, and D is a substituted carbon atom, at most only one of A, B, and D is N-oxide and not all of A, B and D are substituted carbon atoms; and n is 1 or 2, or a pharmaceutically acceptable salt, ester, or amide thereof.

2. A compound having the following formula:

wherein $R^1$, $R^2$ and $R^3$ are independently selected from the group consisting of aryl, heteroaryl and heterocyclo;

$R^4$ is selected from the group consisting of alkyl, hydroxy, alkoxy, carbocycloalkyl and amino;

$R^5$ and $R^6$ are independently selected from the group consisting of hydrogen and alkyl;

$R^7$ is selected from the group consisting of hydrogen, alkyl, hydroxy, alkoxy and amino;

$R^8$ is selected from the group consisting of hydrogen and alkyl;

$R^9$ and $R^{10}$ are independently selected from the group consisting of hydrogen, alkyl and halo;

A, B and D are independently selected from the group consisting of a substituted carbon atom, a nitrogen atom, and N-oxide, wherein at least one of A, B, and D is a substituted carbon atom, at most only one of A, B, and D is N-oxide and not all of A, B and D are substituted carbon atoms:

n is 1 or 2; and p is 0, 1, 2, or 3;

or a pharmaceutically acceptable salt, ester, or amide thereof.

3. The compound of claim 1, or a pharmaceutically acceptable salt, ester, or amide thereof, wherein $R^9$, $R^{10}$ and $R^{11}$ are each hydrogen.

4. The compound of claim 2, or a pharmaceutically acceptable salt, ester, or amide thereof, wherein $R^9$ and $R^{10}$ and are each hydrogen.

5. The compound of claim 4 wherein $R^1$ is selected from the group consisting of aryl and heteroaryl;

$R^4$ is selected from the group consisting of alkyl and alkoxy;

$R^6$ is hydrogen; and $R^8$ is hydrogen, or a pharmaceutically acceptable salt, ester, or amide thereof.

6. The compound of claim 5, or a pharmaceutically acceptable salt, ester, or amide thereof, wherein p is 1.

7. The compound of claim 6, or a pharmaceutically acceptable salt, ester, or amide thereof, wherein $R^7$ is hydrogen.

8. A pharmaceutical composition comprising a compound of claim 1, 2, 3, 4, 5, 6, or 7, or a pharmaceutically acceptable salt, ester, or amide, thereof, and a pharmaceutically acceptable diluent or carrier.

9. A method for treating cardiac arrhythmias which comprises administering to a patient in need thereof, a pharmaceutically effective amount of a compound of claim 1, 2, 3, 4, 5, 6 or 7 or a pharmaceutically acceptable salt, ester, or amide, thereof.

* * * * *